US009131725B2

(12) United States Patent
Chen et al.

(10) Patent No.: US 9,131,725 B2
(45) Date of Patent: Sep. 15, 2015

(54) GENE AND VARIATIONS ASSOCIATE WITH BM1 PHENOTYPE, MOLECULAR MARKERS, AND THEIR USE

(75) Inventors: Wei Chen, Carmel, IN (US); Nathan J. VanOpdorp, Geneseo, IL (US); Siva P. Kumpatla, Carmel, IN (US); Peizhong Zheng, Carmel, IN (US); Peter D. Friedemann, Philo, IL (US); Thomas W. Greene, West Des Moines, IA (US); Dennis Fitzl, Davenport, IA (US)

(73) Assignee: Agrigenetics, Inc., Indianapolis, IN (US)

( * ) Notice: Subject to any disclaimer, the term of this patent is extended or adjusted under 35 U.S.C. 154(b) by 657 days.

(21) Appl. No.: 13/342,785

(22) Filed: Jan. 3, 2012

(65) Prior Publication Data

US 2012/0174255 A1 Jul. 5, 2012

Related U.S. Application Data

(60) Provisional application No. 61/429,390, filed on Jan. 3, 2011.

(51) Int. Cl.

| | |
|---|---|
| ***C12N 15/82*** | (2006.01) |
| ***A23L 1/31*** | (2006.01) |
| ***A23K 1/18*** | (2006.01) |
| ***C07K 14/415*** | (2006.01) |
| ***C10L 1/02*** | (2006.01) |
| ***C12N 9/04*** | (2006.01) |

(52) U.S. Cl.

CPC ................ *A23L 1/31* (2013.01); *A23K 1/1813* (2013.01); *C07K 14/415* (2013.01); *C10L 1/02* (2013.01); *C12N 9/0006* (2013.01); *C12N 15/8209* (2013.01); *C12N 15/8255* (2013.01); *C10G 2300/1014* (2013.01)

(58) Field of Classification Search

CPC .................. C10G 2300/1014; C12N 15/8209; C12N 9/0006; C12N 15/8255; C10L 1/02; C07K 14/415; A23L 1/31; A23K 1/1813

See application file for complete search history.

(56) References Cited

U.S. PATENT DOCUMENTS

| | | | | |
|---|---|---|---|---|
| 5,767,080 | A | 6/1998 | Beck et al. | |
| 5,824,842 | A | 10/1998 | MacKay et al. | |
| 6,552,249 | B1 | 4/2003 | Cahoon et al. | |
| 6,921,643 | B2 * | 7/2005 | Gill et al. | 435/6.12 |
| 7,396,921 | B2 | 7/2008 | Gill et al. | |
| 7,429,649 | B2 | 9/2008 | Spangenberg et al. | |
| 2006/0263860 | A1 | 11/2006 | Vermerris et al. | |
| 2008/0313774 | A1 | 12/2008 | Spangenberg et al. | |
| 2010/0203196 | A1 * | 8/2010 | Murigneux et al. | 426/54 |

OTHER PUBLICATIONS

Halpin et al 1998 The Plant Journal 14:545-553, provided by Applicant.*

GenBank: ACG45271.1, Dec. 10, 2008, 1 page.

Cao, Jun "Genetic dissection of the rf2a-mediated fertility restoration pathway in maize," 2007, 142 pages.

Guillaumie, Sabine et al., "Differential expression of phenylpropanoid and related getnes in borwn-midrib bm1, bm2, bm3 and bm4 young near-isogenic maize plants," Planta, 2007, pp. 235-250, vol. 226.

Halpin, Claire et al., "Brown-midrib maize (bm1)—a mutation affecting the cinnamyl alcohol dehydrogenase gene," The Plant Journal, 1998, pp. 545-553, vol. 14.

Marita, Jane M., et al., "Variations in the cell wall composition of maize brown midrib mutants," Journal of Agricultural and Food Chemistry, 2003, pp. 1313-1321, vol. 51.

Saballos Ana, et al., "A genomewide analysis of the cinnamyl alcohol dehydrogenase family in *Sorghum* [*Sorghum bicolor* (L.) moench] identifies SbCAD2 as the brown midrib6 gene," Genetics Society of America, 2009, pp. 783-795 (Feb. 2009).

Sattler, Scott E., et al., "A nonsense mutation in a cinnamyl alcohol dehydrogenase gene is responsible for the *Sorghum* brown midrib6 phenotype1[W][OA]," Plant Physiology, Jun. 2009, pp. 584-595, vol. 150.

Vermerris, Wilfred et al.., "Molecular breeding to enhance ethanol production form corn and *Sorghum* stover," Crop Sci, 2007, pp. S142-S153, vol. 47(S3).

Vignols, Florence et al., "The brown midrib3 (bm3) mutation in maize occurs in the gene encoding caffeic acid o-mehtyltransferace," The Plant Cell, Apr. 1995, pp. 407-416, vol. 7.

Alexandrov, N. N. et al., Insights into corn genes derived from large-scale cDNA sequencing. Plant Molecular Biology. Jan. 2009, vol. 69, Nos. 1-2, p. 179-194.

Gardiner, J. et al., Anchoring 9,371 maize expressed sequence tagged unigenes to the bacterial artificial chromosome contig map by two-dimensional overgo hybridization. Plant Physiology. Apr. 2004, vol. 134, No. 4, pp. 1317-1326.

International Search Report for International Application No. PCT/US2012/020062, dated Oct. 29, 2012.

Written Opinion for International Application No. PCT/US2012/020062, dated Oct. 29, 2012.

* cited by examiner

*Primary Examiner* — Brent T Page

(74) *Attorney, Agent, or Firm* — Eric J. Kraus; Traskbritt, P.C.

(57) ABSTRACT

This disclosure concerns specific naturally-occurring mutant maize cad2 genes, which altered genes contribute to the bm1 maize phenotype in particular maize lines. In some embodiments, compositions and methods are provided that utilize a nucleic acid molecule comprising a mutant cad2 gene, and/or markers linked to a mutant cad2gene.

3 Claims, 31 Drawing Sheets

FIG. 1.
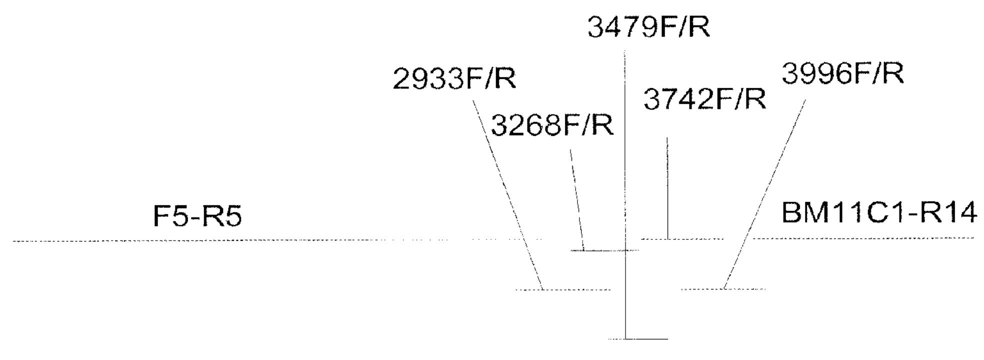
*515Dbm1 CAD2* (5.9 kb) and 6XN442 *CAD2* (5.9 kb)
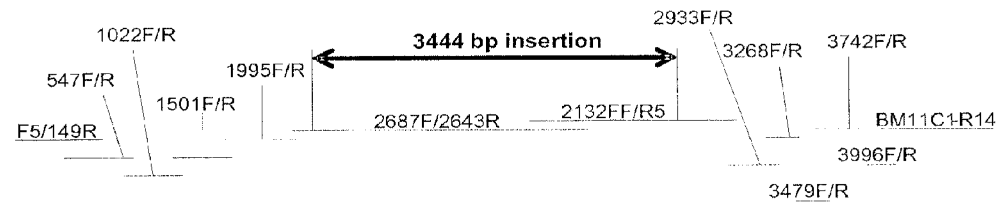
*DASbm1 CAD2* (9.3 kb)

FIG. 3a.

```
DASbm1 (SEQ ID NO:23)    (1) aatgcacgatgtcaactctcttgcctataattatg
515Dbm1 (SEQ ID NO:1)    (1) aatgcacgatgtcaactctcttgcctataattatg
6XN442 (SEQ ID NO:4)     (1) aatgcacgatgtcaactctcttgcctataattatg
B73 (SEQ ID NO:7)        (1) aatgcacgatgtcaactctcttgcctataattatg
                                                  *
(36)  ttcaaactctcgtcaataatagtagctagtactgttattgtaaagtatcgctaaaat
(36)  ttcaaactctcgtcaataatagtagctagtgctgttattgtaaagtatcgctaaaat
(36)  ttcaaactctcgtcaataatagtagctagtactgttattgtaaagtatcgctaaaat
(36)  ttcaaactctcgtcaataatagtagctagtactgttattgtaaagtatcgctaaaat

(93)  atgcatatatacttataacttatccatgttaaagaaaatcgaatatgctagcaaaga
(93)  atgcatatatacttataacttatccatgttaaagaaaatcgaatatgctagcaaaga
(93)  atgcatatatacttataacttatccatgttaaagaaaatcgaatatgctagcaaaga
(93)  atgcatatatacttataacttatccatgttaaagaaaatcgaatatgctagcaaaga

(150) catatgggcccgttgaggagagctacgttacatttgatttctaggagaaagcagagt
(150) catatgggcccgttgaggagagctacgttacatttgatttctaggagaaagcagagt
(150) catatgggcccgttgaggagagctacgttacatttgatttctaggagaaagcagagt
(150) catatgggcccgttgaggagagctacgttacatttgatttctaggagaaagcagagt

(207) gaagagctggtgaaaatcgattctctattatcttcactagaatataaatgaagcaca
(207) gaagagctggtgaaaatcgattctctattatcttcactagaatataaatgaagcaca
(207) gaagagctggtgaaaatcgattctctattatcttcactagaatataaatgaagcaca
(207) gaagagctggtgaaaatcgattctctattatcttcactagaatataaatgaagcaca
                                *
(264) tttttagctccagctcttagcgcaaatagagaaactctcctaattgtagcatgaatg
(264) tttttagctccagctcttagtgcaaatagagaaactctcctaattgtagcatgaatg
(264) tttttagctccagctcttagtgcaaatagagaaactctcctaattgtagcatgaatg
(264) tttttagctccagctcttagcgcaaatagagaaactctcctaattgtagcatgaatg

(321) agatgacattataaaagcctttgatgagattttcttccgagaagctgaagctcctca
(321) agatgacattataaaagcctttgatgagattttcttccgagaagctgaagctcctca
(321) agatgacattataaaagcctttgatgagattttcttccgagaagctgaagctcctca
(321) agatgacattataaaagcctttgatgagattttcttccgagaagctgaagctcctca
                                                  *
(378) gatagcccaatgatatgtatgtaagtgtatttttttt-aaaaaaagcgggcaaatga
(378) gatagcccaatgatatgtatgtaagtgtatttttttttaaaaaaagcgggcaaatga
(378) gatagcccaatgatatgtatgtaagtgtatttttttt-aaaaaaagcgggcaaatga
(378) gatagcccaatgatatgtatgtaagtgtatttttttt-aaaaaaagcgggcaaatga
                *
(434) aactaaatcatcctatcccctttaatatactgagatgccaattagttggttgccagc
(435) aactaaatcatcctatcccctttaatatactgagatgccaattagttggttgccagc
(434) aactaaatcgtcctatcccctttaatatactgagatgccaattagttggttgccagc
(434) aactaaatcatcctatcccctttaatatactgagatgccaattagttggttgccagc
```

FIG. 3b.

```
(491)  cggagtatggtggatgggatcctcctattggttaaattatgaatgaattgtttggtt
(492)  cggagtatggtggatgggatcctcctattggttaaattatgaatgaattgtttggtt
(491)  cggagtatggtggatgggatcctcctattggttaaattatgaatgaattgtttggtt
(491)  cggagtatggtggatgggatcctcctattggttaaattatgaatgaattgtttggtt

(548)  gcccggtccaatctttcttatgtctgtttcgtttagatcgtgtacaccacttcttat
(549)  gcccggtccaatctttcttatgtctgtttcgtttagatcgtgtacaccacttcttat
(548)  gcccggtccaatctttcttatgtctgtttcgtttagatcgtgtacaccacttcttat
(548)  gcccggtccaatctttcttatgtctgtttcgtttagatcgtgtacaccacttcttat

(605)  tgtttaaatggccaatttaatcggggcctaaacgacatatgtgcctcaatttaccat
(606)  tgtttaaatggccaatttaatcggggcctaaacgacatatgtgcctcaatttaccat
(605)  tgtttaaatggccaatttaatcggggcctaaacgacatatgtgcctcaatttaccat
(605)  tgtttaaatggccaatttaatcggggcctaaacgacatatgtgcctcaatttaccat

(662)  accaatgatgccgcttacgtgaatagttgaataccgatactactactaccgcacgcg
(663)  accaatgatgccgcttacgtgaatagttgaataccgatactactactaccgcacgcg
(662)  accaatgatgccgcttacgtgaatagttgaataccgatactactactaccgcacgcg
(662)  accaatgatgccgcttacgtgaatagttgaataccgatactactactaccgcacgcg
                        *                        *
(719)  tcatggtttaaccttttaacagttggattgaaacatcagcgaccactcggcacttgg
(720)  tcatggtttaacctttcaacagttggattgaaacatcagcggccactcggcacttgg
(719)  tcatggtttaaccttttaacagttggattgaaacatcagcgaccactcggcacttgg
(719)  tcatggtttaaccttttaacagttggattgaaacatcagcgaccactcggcacttgg

(776)  gtgacaatttgtcacacacctcgtagtcgagtggaaatgcacttacccaatttctca
(777)  gtgacaatttgtcacacacctcgtagtcgagtggaaatgcacttacccaatttctca
(776)  gtgacaatttgtcacacacctcgtagtcgagtggaaatgcacttacccaatttctca
(776)  gtgacaatttgtcacacacctcgtagtcgagtggaaatgcacttacccaatttctca

(833)  acccataagactatttccagcatctcgattaatccccatatttaaaatcaactttca
(834)  acccataagactatttccagcatctcgattaatccccatatttaaaatcaactttca
(833)  acccataagactatttccagcatctcgattaatccccatatttaaaatcaactttca
(833)  acccataagactatttccagcatctcgattaatccccatatttaaaatcaactttca

(890)  tagtttatattgtgaagtgttttatgtgacgacattagtggatttatggacacggtc
(891)  tagtttatattgtgaagtgttttatgtgacgacattagtggatttatggacacggtc
(890)  tagtttatattgtgaagtgttttatgtgacgacattagtggatttatggacacggtc
(890)  tagtttatattgtgaagtgttttatgtgacgacattagtggatttatggacacggtc

(947)  taaggacccgtgacttgtatttttcttcattgacctagctagctagctagctagcat
(948)  taaggacccgtgacttgtatttttcttcattgacctagctagctagctagctagcat
(947)  taaggacccgtgacttgtatttttcttcattgacctagctagctagctagctagcat
(947)  taaggacccgtgacttgtatttttcttcattgacctagctagctagctagctagcat
```

FIG. 3c.

```
(1004) cgtgaagccacgcccatgcgtttggtatcgtccgagttgtgtacaatttccagccag
(1005) cgtgaagccacgcccatgcgtttggtatcgtccgagttgtgtacaatttccagccag
(1004) cgtgaagccacgcccatgcgtttggtatcgtccgagttgtgtacaatttccagccag
(1004) cgtgaagccacgcccatgcgtttggtatcgtccgagttgtgtacaatttccagccag

(1061) tggaatcacagttattggatcattttggtacgtataacgtattctttttgtatttcc
(1062) tggaatcacagttattggatcattttggtacgtataacgtattctttttgtatttcc
(1061) tggaatcacagttattggatcattttggtacgtataacgtattctttttgtatttcc
(1061) tggaatcacagttattggatcattttggtacgtataacgtattctttttgtatttcc

(1118) tgtctaaagacattaatttcagagaagccgggtctattttagaagggcttggcttct
(1119) tgtctaaagacattaatttcagagaagccgggtctattttagaagggcttggcttct
(1118) tgtctaaagacattaatttcagagaagccgggtctattttagaagggcttggcttct
(1118) tgtctaaagacattaatttcagagaagccgggtctattttagaagggcttggcttct

(1175) tcccgtttggtagacctcctcgaaagacgaaagtcttacttcctctggtttcctatt
(1176) tcccgtttggtagacctcctcgaaagacgaaagtcttacttcctctggtttcctatt
(1175) tcccgtttggtagacctcctcgaaagacgaaagtcttacttcctctggtttcctatt
(1175) tcccgtttggtagacctcctcgaaagacgaaagtcttacttcctctggtttcctatt

(1232) agttatcgttttgaataaagttcgagtcaaacttataaaattttgactacaaataac
(1233) agttatcgttttgaataaagttcgagtcaaacttataaaattttgactacaaataac
(1232) agttatcgttttgaataaagttcgagtcaaacttataaaattttgactacaaataac
(1232) agttatcgttttgaataaagttcgagtcaaacttataaaattttgactacaaataac
                                                            *
(1289) tattttgttatttagttttggaacctaatatttatatgcaccaatttgttataaaac
(1290) tattttgttatttagttttggaacctaatatttatatgcaccaatttgttataaaaa
(1289) tattttgttatttagttttggaacctaatatttatatgcaccaatttgttataaaaa
(1289) tattttgttatttagttttggaacctaatatttatatgcaccaatttgttataaaac

(1346) gtacttttataaaagtataaatgtattaagagttcatttgtattttaacaaaaaata
(1347) gtacttttataaaagtataaatgtattaagagttcatttgtattttaacaaaaAata
(1346) gtacttttataaaagtataaatgtattaagagttcatttgtattttaacaaaaaata
(1346) gtacttttataaaagtataaatgtattaagagttcatttgtattttaacaaaaaata
            *
(1403) ttggtcaaagttatattttggagaccgtgtcgttgtcctaaacgacaactaatagga
(1404) ttggttaaagttatattttggagaccgtgtcgttgtcctaaacgacaactaatagga
(1403) ttggtcaaagttatattttggagaccgtgtcgttgtcctaaacgacaactaatagga
(1403) ttggtcaaagttatattttggagaccgtgtcgttgtcctaaacgacaactaatagga

(1460) aaccggagggagtactgattttctcctgcagcgggcacagaagatcatgctggaaag
(1461) aaccggagggagtactgattttctcctgcagcgggcacagaagatcatgctggaaag
(1460) aaccggagggagtactgattttctcctgcagcgggcacagaagatcatgctggaaag
(1460) aaccggagggagtactgattttctcctgcagcgggcacagaagatcatgctggaaag
```

FIG. 3d.

```
(1517) gtagtaggtacaggtagcctggagcggaggagttgccactttgcacagtgccgatcg
(1518) gtagtaggtacaggtagcctggagcggaggagttgccactttgcacagtgccgatcg
(1517) gtagtaggtacaggtagcctggagcggaggagttgccactttgcacagtgccgatcg
(1517) gtagtaggtacaggtagcctggagcggaggagttgccactttgcacagtgccgatcg
                         *                                ***
(1574) agctcgcagccactatatagcacgcaccctgctcaagcatcttttccttacccagaa
(1575) agctcgcagccactatatagcacgcaccctgctcaagcatcttttccttacccagaa
(1574) agctcgcagcccctatatagcacgcaccctgctcaagcatcttttccttaccctata
(1574) agctcgcagccactatatagcacgcaccctgctcaagcatcttttccttacccagaa
       *********  ******
(1631) agatcgcactacccggcgctcgcgcggctttctttcccaactccgacgaaggctagc
(1632) agatcgcactacccggcgctcgcgcggctttctttcccaactccgacgaaggctagc
(1631) ---------ta------gctcgcgcggctttctttcccaactccgacgaaggctagc
(1631) agatcgcactacccggcgctcgcgcggctttctttcccaactccgacgaaggctagc

(1688) tacaccacctgGTGCGGGCTCGTCTCCATCGCCCGCCACCCGCTCCGTCGTCGTCGT
(1689) tacaccacctgGTGCGGGCTCGTCTCCATCGCCCGCCACCCGCTCCGTCGTCGTCGT
(1673) tacaccacctgGTGCGGGCTCGTCTCCATCGCCCGCCACCCGCTCCGTCGTCGTCGT
(1688) tacaccacctgGTGCGGGCTCGTCTCCATCGCCCGCCACCCGCTCCGTCGTCGTCGT

(1745) CCCCGCCGCGCCGATCCCGAATCGAATGGGGAGCCTGGCGTCCGAGAGGAAGGTGGT
(1746) CCCCGCCGCGCCGATCCCGAATCGAATGGGGAGCCTGGCGTCCGAGAGGAAGGTGGT
(1730) CCCCGCCGCGCCGATCCCGAATCGAATGGGGAGCCTGGCGTCCGAGAGGAAGGTGGT
(1745) CCCCGCCGCGCCGATCCCGAATCGAATGGGGAGCCTGGCGTCCGAGAGGAAGGTGGT

(1802) CGGGTGGGCCGCCAGGGACGCCACCGGACACCTCTCCCCCTACTCCTACACCCTCAG
(1803) CGGGTGGGCCGCCAGGGACGCCACCGGACACCTCTCCCCCTACTCCTACACCCTCAG
(1787) CGGGTGGGCCGCCAGGGACGCCACCGGACACCTCTCCCCCTACTCCTACACCCTCAG
(1802) CGGGTGGGCCGCCAGGGACGCCACCGGACACCTCTCCCCCTACTCCTACACCCTCAG

(1859) gtactacgccgcgccggcgccctcgtgtttgtcctctcctccagtccctcccgtctg
(1860) gtactacgccgcgccggcgccctcgtgtttgtcctctcctccagtccctcccgtctg
(1844) gtactacgccgcgccggcgccctcgtgtttgtcctctcctccagtccctcccgtctg
(1859) gtactacgccgcgccggcgccctcgtgtttgtcctctcctccagtccctcccgtctg

(1916) tatatgtccgactgtctccgcccttttgcaaacacgcaaatggatggatccaggagg
(1917) tatatgtccgactgtctccgcccttttgcaaacacgcaaatggatggatccaggagg
(1901) tatatgtccgactgtctccgcccttttgcaaacacgcaaatggatggatccaggagg
(1916) tatatgtccgactgtctccgcccttttgcaaacacgcaaatggatggatccaggagg

(1973) acgagagacggttagtttctgcacgcgcctcctccagtagttctccgagttctcggg
(1974) acgagagacggttagtttctgcacgcgcctcctccagtagttctccgagttctcggg
(1958) acgagagacggttagtttctgcacgcgcctcctccagtagttctccgagttctcggg
(1973) acgagagacggttagtttctgcacgcgcctcctccagtagttctccgagttctcggg
```

FIG. 3e.

```
(2030) aagaacagaaaatttgattgatgtttttttgatgaaaaataaaaagggacttgggg
(2031) aagaacagaaaatttgattgatgtttttttgatgaaaaataaaaagggacttgggg
(2015) aagaacagaaaatttgattgatgtttttttgatgaaaaataaaaagggacttgggg
(2030) aagaacagaaaatttgattgatgtttttttgatgaaaaataaaaagggacttgggg

(2087) catattttcgatcaacttgcaacggaagatgactaggagtacgtacgtagcgtagcg
(2088) catattttcgatcaacttgcaacggaagatgactaggagtacgtacgtagcgtagcg
(2072) catattttcgatcaacttgcaacggaagatgactaggagtacgtacgtagcgtagcg
(2087) catattttcgatcaacttgcaacggaagatgactaggagtacgtacgtagcgtagcg

(2144) gcggcgggttttaatttggggagcactctgttagtctgttgcatatatgggagtac
(2145) gcggcgggttttaatttggggagcactctgttagtctgttgcatatatgggagtac
(2129) gcggcgggttttaatttggggagcactctgttagtctgttgcatatatgggagtac
(2144) gcggcgggttttaatttggggagcactctgttagtctgttgcatatatgggagtac
                                                         *
(2201) ctgattcgttgcagttattattatctatacgcgtacgatatgttttaggggtgttt
(2202) ctgattcgttgcagttattattatctatacgcgtacgatatgttttaggggtgttt
(2186) ctgattcgttgcagttattattatctatacgcgtacgatatgttttagggg-tgttt
(2201) ctgattcgttgcagttattattatctatacgcgtacgatatgttttaggggtgttt
                 *
(2258) ggttgctcctgctaaagtttagtccgggtcacatcaagcgttttacttttaaatagg
(2259) ggttgctcctgttaaagtttagtccgggtcacatcaagcgttttacttttaaatagg
(2242) ggttgctcctgctaaagtttagtccgggtcacatcaagcgttttacttttaaatagg
(2258) ggttgctcctgctaaagtttagtccgggtcacatcaagcgttttacttttaaatagg

(2315) agtatgaaatatagacccaaccaactagactagattcgtctcgtcttttaatcttcg
(2316) agtatgaaatatagacccaaccaactagactagattcgtctcgtcttttaatcttcg
(2299) agtatgaaatatagacccaaccaactagactagattcgtctcgtcttttaatcttcg
(2315) agtatgaaatatagacccaaccaactagactagattcgtctcgtcttttaatcttcg

(2372) gctgacaaattagttttataatccgactacatttaatacccggaacagaggttcaaa
(2373) gctgacaaattagttttataatccgactacatttaatacccggaacagaggttcaaa
(2356) gctgacaaattagttttataatccgactacatttaatacccggaacagaggttcaaa
(2372) gctgacaaattagttttataatccgactacatttaatacccggaacagaggttcaaa

(2429) cattcgatgggacagagactaaattttagcagggtgtaaccaaacaccccccttagtc
(2430) cattcgatgggacagagactaaattttagcagggtgtaaccaaacaccccccttagtc
(2413) cattcgatgggacagagactaaattttagcagggtgtaaccaaacaccccccttagtc
(2429) cattcgatgggacagagactaaattttagcagggtgtaaccaaacaccccccttagtc

(2486) cacaacaagagcattatgcgctgtgttgcatcatgcatatatgatacgtcttcaact
(2487) cacaacaagagcattatgcgctgtgttgcatcatgcatatatgatacgtcttcaact
(2470) cacaacaagagcattatgcgctgtgttgcatcatgcatatatgatacgtcttcaact
(2486) cacaacaagagcattatgcgctgtgttgcatcatgcatatatgatacgtcttcaact
```

FIG. 3f.

```
(2543) tcttgcggtccaactctagatagtgcacatgcatatgccaaatacggatactggaca
(2544) tcttgcggtccaactctagatagtgcacatgcatatgccaaatacggatactggaca
(2527) tcttgcggtccaactctagatagtgcacatgcatatgccaaatacggatactggaca
(2543) tcttgcggtccaactctagatagtgcacatgcatatgccaaatacggatactggaca

(2600) agatagcacacaagcagagcaggttgggcgagcgtacactgcacgtatgcttctctt
(2601) agatagcacacaagcagagcaggttgggcgagcgtacactgcacgtatgcttctctt
(2584) agatagcacacaagcagagcaggttgggcgagcgtacactgcacgtatgcttctctt
(2600) agatagcacacaagcagagcaggttgggcgagcgtacactgcacgtatgcttctctt

(2657) ctacatggcattttgtttcgaacattaatatatgggtactgctcctgcacagcactg
(2658) ctacatggcattttgtttcgaacattaatatatgggtactgctcctgcacagcactg
(2641) ctacatggcattttgtttcgaacattaatatatgggtactgctcctgcacagcactg
(2657) ctacatggcattttgtttcgaacattaatatatgggtactgctcctgcacagcactg

(2714) cacgtgcttgacgtctcgtacagacccagcagcgtgtgaacttgtaggtaagatacg
(2715) cacgtgcttgacgtctcgtacagacccagcagcgtgtgaacttgtaggtaagatacg
(2698) cacgtgcttgacgtctcgtacagacccagcagcgtgtgaacttgtaggtaagatacg
(2714) cacgtgcttgacgtctcgtacagacccagcagcgtgtgaacttgtaggtaagatacg

(2771) taactactgatatctaggcctgggaatgggccatataaactcatgggcagaaagggg
(2772) taactactgatatct------------------------------------------
(2755) taactactgatatct------------------------------------------
(2771) taactactgatatct------------------------------------------

(2828) ctccaaacttgtgggctaacaaatttgagtttttttgggctttccactgattagggc
(2787) ---------------------------------------------------------
(2770) ---------------------------------------------------------
(2786) ---------------------------------------------------------

(2885) aggcggcgtcaggctgatcggggtggcgcgcggcgccggggagcgccccatcgtatt
(2787) ---------------------------------------------------------
(2770) ---------------------------------------------------------
(2786) ---------------------------------------------------------

(2942) cgtgcctctcaaggtcacaccgcctcgcgctcgtctcctctccttgtcgcttcgatt
(2787) ---------------------------------------------------------
(2770) ---------------------------------------------------------
(2786) ---------------------------------------------------------

(2999) cgttcccctcccgctcccgctcgccctcgccatgaatgatgtcgcctgaatctggtt
(2787) ---------------------------------------------------------
(2770) ---------------------------------------------------------
(2786) ---------------------------------------------------------
```

FIG. 3g.

```
(3056) ctgggggtttcggtagctactacttggccggcttgccgcctcttcttctttgcgttg
(2787) ---------------------------------------------------------
(2770) ---------------------------------------------------------
(2786) ---------------------------------------------------------

(3113) ctgctctgccattttcctattgtagtagcggcgccatgcgagaacgagatgagccaa
(2787) ---------------------------------------------------------
(2770) ---------------------------------------------------------
(2786) ---------------------------------------------------------

(3170) ctgcagaggttggcttggcttctgccattttcttctttgctgcagaggttcgcggac
(2787) ---------------------------------------------------------
(2770) ---------------------------------------------------------
(2786) ---------------------------------------------------------

(3227) gcaggtcggaccactgccgcgcccttcctcttcctgccggccgccgcactcccgcca
(2787) ---------------------------------------------------------
(2770) ---------------------------------------------------------
(2786) ---------------------------------------------------------

(3284) gcgccgtactacttactacctgcatactgtattctgtagtagtatgaaaaggtaaag
(2787) ---------------------------------------------------------
(2770) ---------------------------------------------------------
(2786) ---------------------------------------------------------

(3341) gcggcgtactgctatagtatctctgcagaatgttcggaggaggagtacaccaactga
(2787) ---------------------------------------------------------
(2770) ---------------------------------------------------------
(2786) ---------------------------------------------------------

(3398) aagaggtttaggaaagttgcaccgtggatctagaattctagatgcattagtgtagcc
(2787) ---------------------------------------------------------
(2770) ---------------------------------------------------------
(2786) ---------------------------------------------------------

(3455) tacagtagccctgtacacacataaaggcatttttcttataaaattgtctcgcaaaat
(2787) ---------------------------------------------------------
(2770) ---------------------------------------------------------
(2786) ---------------------------------------------------------

(3512) gggatttttttgtgctaattatagggtgctttagcgccacctgggatttttttgtgc
(2787) ---------------------------------------------------------
(2770) ---------------------------------------------------------
(2786) ---------------------------------------------------------
```

FIG. 3h.

```
(3569) taattatatgcagcttccatagaccaccacaggcattcccgcatgcagttcgctctg
(2787) ---------------------------------------------------------
(2770) ---------------------------------------------------------
(2786) ---------------------------------------------------------

(3626) aatgcctcctttcattctattactatccctgaacgacgacccatctcagggaaatag
(2787) ---------------------------------------------------------
(2770) ---------------------------------------------------------
(2786) ---------------------------------------------------------

(3683) ccattaaatgatagcagccttttttaaagtatggcttggtttgcgatgttattatgg
(2787) ---------------------------------------------------------
(2770) ---------------------------------------------------------
(2786) ---------------------------------------------------------

(3740) ttcgaaaagttgctctattttagtctcatttattttataaattgcagtactaaactg
(2787) ---------------------------------------------------------
(2770) ---------------------------------------------------------
(2786) ---------------------------------------------------------

(3797) ttttagtctatagttccttttttagatgactaaagggattaaacaaaaaagacaccc
(2787) ---------------------------------------------------------
(2770) ---------------------------------------------------------
(2786) ---------------------------------------------------------

(3854) gtaaattaatcagtcgttaaacagtgctagtactatgcatttcatcgcgtaaattaa
(2787) ---------------------------------------------------------
(2770) ---------------------------------------------------------
(2786) ---------------------------------------------------------

(3911) tcaattgaatggtttcaattggtgattttgcagcctaggccatggagggggtatcat
(2787) ---------------------------------------------------------
(2770) ---------------------------------------------------------
(2786) ---------------------------------------------------------

(3968) cagctccagaaatggacgaggctatctcaactgaccaatcaagcagatcaacaaaaa
(2787) ---------------------------------------------------------
(2770) ---------------------------------------------------------
(2786) ---------------------------------------------------------

(4025) gaagggctaaagtgtgggatcatgttgattcagagctaatagatgggaaagagaagg
(2787) ---------------------------------------------------------
(2770) ---------------------------------------------------------
(2786) ---------------------------------------------------------
```

FIG. 3i.

```
(4082) cggtttgcaaatactgtaaggcccacttatcttctgctgcgggtaaaggtacaactc
(2787) ---------------------------------------------------------
(2770) ---------------------------------------------------------
(2786) ---------------------------------------------------------

(4139) atctaaataggcatatttctgtgtattgccatgcaattccaccagaagagagacaaa
(2787) ---------------------------------------------------------
(2770) ---------------------------------------------------------
(2786) ---------------------------------------------------------

(4196) ggttcttagcgacccaaaaaacaaagcctgatgttgctcatgttttcgacccagtag
(2787) ---------------------------------------------------------
(2770) ---------------------------------------------------------
(2786) ---------------------------------------------------------

(4253) tctttcgtggtctaatagccaagtacttccttagcgcagagatttcattttgaaagt
(2787) ---------------------------------------------------------
(2770) ---------------------------------------------------------
(2786) ---------------------------------------------------------

(4310) gtgaagatccatcctggaaagaaatgataagttattgtcaaccatcttttcgattag
(2787) ---------------------------------------------------------
(2770) ---------------------------------------------------------
(2786) ---------------------------------------------------------

(4367) tcggtcgacagactgtccgttcagattgtatgttgttgtatgaagaggagaagttgc
(2787) ---------------------------------------------------------
(2770) ---------------------------------------------------------
(2786) ---------------------------------------------------------

(4424) agttaattgagcagtttacaaagttgaaatctcatgttagtttgactgctgatcttt
(2787) ---------------------------------------------------------
(2770) ---------------------------------------------------------
(2786) ---------------------------------------------------------

(4481) ggtcctctaaccaaaaccttggatatcttggtgtaacagcacatttcattagtgaag
(2787) ---------------------------------------------------------
(2770) ---------------------------------------------------------
(2786) ---------------------------------------------------------

(4538) attttgagttgcacaaaaagattattgcattcaagaagatttccttcccacatacat
(2787) ---------------------------------------------------------
(2770) ---------------------------------------------------------
(2786) ---------------------------------------------------------
```

FIG. 3j.

```
(4595) cttatgctgtgcaagatggtattacctcttgtttgctagagtggggattggttggtg
(2787) ---------------------------------------------------------
(2770) ---------------------------------------------------------
(2786) ---------------------------------------------------------

(4652) atttgtttaccctgactttggataatgctagtgtaaacaatagagcaatgaaagata
(2787) ---------------------------------------------------------
(2770) ---------------------------------------------------------
(2786) ---------------------------------------------------------

(4709) tgcgagatgctttgggcagccagatgtttttcagtggtgaacacctccatgtgaggt
(2787) ---------------------------------------------------------
(2770) ---------------------------------------------------------
(2786) ---------------------------------------------------------

(4766) gttcttctcatgtgctcaacatcatggttcaagctggactaaaggtcgttccaatg
(2787) ---------------------------------------------------------
(2770) ---------------------------------------------------------
(2786) ---------------------------------------------------------

(4823) cagaatatcattagcattatatagtttatcttttgtcttaatcaccaaagatgtttt
(2787) ---------------------------------------------------------
(2770) ---------------------------------------------------------
(2786) ---------------------------------------------------------

(4880) tcagaatatcattagcagccagatgtttttgtcttaatctcaacatcatttcttaa
(2787) ---------------------------------------------------------
(2770) ---------------------------------------------------------
(2786) ---------------------------------------------------------

(4937) tcaccaaagttttatcttttgtctgttcttctctaatatccatgcatctaaataagc
(2787) ---------------------------------------------------------
(2770) ---------------------------------------------------------
(2786) ---------------------------------------------------------

(4994) cctaatagtatctctcattctcttgttactattagtatttaaacttattactattag
(2787) ---------------------------------------------------------
(2770) ---------------------------------------------------------
(2786) ---------------------------------------------------------

(5051) tatttaagcgtgaataattatcattagcatttaagttacattttataaaccaaacga
(2787) ---------------------------------------------------------
(2770) ---------------------------------------------------------
(2786) ---------------------------------------------------------
```

FIG. 3k.

```
(5108) cacctaaagtgctccgtcatagttggctacttgccagccgattatttagcacgcaag
(2787) ---------------------------------------------------------
(2770) ---------------------------------------------------------
(2786) ---------------------------------------------------------

(5165) ccatgctcgatggatacaatagtatatgaccaatatagatgacctacgtacatgtgt
(2787) ---------------------------------------------------------
(2770) ---------------------------------------------------------
(2786) ---------------------------------------------------------

(5222) tctatgcttcagcaagcataatatgtttcttgccttcgcatcaactcaagtgtgtga
(2787) ---------------------------------------------------------
(2770) ---------------------------------------------------------
(2786) ---------------------------------------------------------

(5279) tgatatgttgctgtctagtactaactctgaatcaattaactctgaatttgtccaggc
(2787) ---------------------------------------------------------
(2770) ---------------------------------------------------------
(2786) ---------------------------------------------------------

(5336) taaggagttccttggtgcttccggtgacaagcgaaaggaagtcaattaactctgaat
(2787) ---------------------------------------------------------
(2770) ---------------------------------------------------------
(2786) ---------------------------------------------------------

(5393) cagtggttctgctgcaaggtaaattgcctgtatataattatccatgtcagaaccaac
(2787) ---------------------------------------------------------
(2770) ---------------------------------------------------------
(2786) ---------------------------------------------------------

(5450) tttatctaccaggattaatttttagtctcccaattttatgccccagttatattttat
(2787) ---------------------------------------------------------
(2770) ---------------------------------------------------------
(2786) ---------------------------------------------------------

(5507) cctagtgaagttttactgctctcatatacttagatgaactaaagttgatcattttgt
(2787) ---------------------------------------------------------
(2770) ---------------------------------------------------------
(2786) ---------------------------------------------------------

(5564) gctcggaacaactctgtataacagtctatatagtttaacagtctatatagtttgcat
(2787) ---------------------------------------------------------
(2770) ---------------------------------------------------------
(2786) ---------------------------------------------------------
```

FIG. 31.

```
(5621) gcaggttacacacaacattttattgaatggaaagaggacactcggtgaccacaagat
(2787) ---------------------------------------------------------
(2770) ---------------------------------------------------------
(2786) ---------------------------------------------------------

(5678) catcagatgatcatttgttgagctctggaactaaatcctctccgcaggtggtaacca
(2787) ---------------------------------------------------------
(2770) ---------------------------------------------------------
(2786) ---------------------------------------------------------

(5735) ggcgggttcccatccgagttccgaggtcactgtaatgctaaattgtcaagttcagtt
(2787) ---------------------------------------------------------
(2770) ---------------------------------------------------------
(2786) ---------------------------------------------------------

(5792) atctgaattcagtttgagttataattctcatcaagcatcaatgtcaccaactgtgta
(2787) ---------------------------------------------------------
(2770) ---------------------------------------------------------
(2786) ---------------------------------------------------------

(5849) gaaatactgaattttagcatggagcgtctttataaacattttagcatggagcagttt
(2787) ---------------------------------------------------------
(2770) ---------------------------------------------------------
(2786) ---------------------------------------------------------

(5906) ctcatcgatcatggctgtcaagttctatttctctacacagttgcactttgtggttgt
(2787) ---------------------------------------------------------
(2770) ---------------------------------------------------------
(2786) ---------------------------------------------------------

(5963) tttctatcatttgtttgtgagcccatggattttactaatttattagcttgtggtggt
(2787) ---------------------------------------------------------
(2770) ---------------------------------------------------------
(2786) ---------------------------------------------------------

(6020) gcttgcttgtatatgaaggcccttggattggcccgtggatttttaaaaggatcgagg
(2787) ---------------------------------------------------------
(2770) ---------------------------------------------------------
(2786) ---------------------------------------------------------

(6077) cggattaggatgtcggggcattaaaaaacggattgaattgagttgtatcaaatcaat
(2787) ---------------------------------------------------------
(2770) ---------------------------------------------------------
(2786) ---------------------------------------------------------
```

FIG. 3m.

```
(6134) ttggatttaagtagggctgggttcactttttaaacttataggattggagtggggttg
(2787) ---------------------------------------------------------
(2770) ---------------------------------------------------------
(2786) ---------------------------------------------------------

(6191) gggccggattgtgacccattatcaggcttactgatatctgcagctacctaccgcctg
(2787) ---------------------------------------gcagctacctaccgcctg
(2770) ---------------------------------------gcagctacctaccgcctg
(2786) ---------------------------------------gcagctacctaccgcctg

(6248) tcgcgatcaccatccatttgtactcgcagtaataataccgattacccttttattatt
(2805) tcgcgatcaccatccatttgtactcgcagtaataataccgattacccttttattatt
(2788) tcgcgatcaccatccatttgtactcgcagtaataataccgattacccttttattatt
(2804) tcgcgatcaccatccatttgtactcgcagtaataataccgattacccttttattatt

(6305) atttctcatgccatcgacgactactagcactatccaacgtacaactgtggcgcgatt
(2862) atttctcatgccatcgacgactactagcactatccaacgtacaactgtggcgcgatt
(2845) atttctcatgccatcgacgactactagcactatccaacgtacaactgtggcgcgatt
(2861) atttctcatgccatcgacgactactagcactatccaacgtacaactgtggcgcgatt
                                                        *
(6362) catatatgcataattctacatggtgctagtcttcggcaagaaaaaaaaactaacact
(2919) catatatgcataattctacatggtgctagtcttcggcaagaaaaaaaa-ctaacact
(2902) catatatgcataattctacatggtgctagtcttcggcaagaaaaaaaa-ctaacact
(2918) catatatgcataattctacatggtgctagtcttcggcaagaaaaaaaaactaacact

(6419) tgtctctttttcatatgggatgtgttgtggtggtgacaacagGAACACAGGCCCTGA
(2975) tgtctctttttcatatgggatgtgttgtggtggtgacaacagGAACACAGGCCCTGA
(2958) tgtctctttttcatatgggatgtgttgtggtggtgacaacagGAACACAGGCCCTGA
(2975) tgtctctttttcatatgggatgtgttgtggtggtgacaacagGAACACAGGCCCTGA

(6476) AGATGTGGTGGTGAAGGTGCTCTACTGCGGGATCTGCCACACGGACATCCACCAGGC
(3032) AGATGTGGTGGTGAAGGTGCTCTACTGCGGGATCTGCCACACGGACATCCACCAGGC
(3015) AGATGTGGTGGTGAAGGTGCTCTACTGCGGGATCTGCCACACGGACATCCACCAGGC
(3032) AGATGTGGTGGTGAAGGTGCTCTACTGCGGGATCTGCCACACGGACATCCACCAGGC

(6533) CAAGAACCACCTCGGGGCTTCAAAGTATCCTATGGTCCCTGGgtgagcacaaacggt
(3089) CAAGAACCACCTCGGGGCTTCAAAGTATCCTATGGTCCCTGGgtgagcacaaacggt
(3072) CAAGAACCACCTCGGGGCTTCAAAGTATCCTATGGTCCCTGGgtgagcacaaacggt
(3089) CAAGAACCACCTCGGGGCTTCAAAGTATCCTATGGTCCCTGGgtgagcacaaacggt

(6590) taacacacacacgcacccagcgatttttcaggacccttggggatccagtatatatat
(3146) taacacacacacgcacccagcgatttttcaggacccttggggatccagtatatatat
(3129) taacacacacacgcacccagcgatttttcaggacccttggggatccagtatatatat
(3146) taacacacacacgcacccagcgatttttcaggacccttggggatccagtatatatat
```

FIG. 3n.

```
          **
(6647) atatgctccgtgtacggtccagaatatacgtactgaatttccaagtgtcctattatt
(3203) atatgctccgtgtacggtccagaatatacgtactgaatttccaagtgtcctattatt
(3186) at--gctccgtgtacggtccagaatatacgtactgaatttccaagtgtcctattatt
(3203) atatgctccgtgtacggtccagaatatacgtactgaatttccaagtgtcctattatt

(6704) caatttgtctcaaaactataaaggatatatatagtgacatgcagtttcagcgttttc
(3260) caatttgtctcaaaactataaaggatatatatagtgacatgcagtttcagcgttttc
(3241) caatttgtctcaaaactataaaggatatatatagtgacatgcagtttcagcgttttc
(3260) caatttgtctcaaaactataaaggatatatatagtgacatgcagtttcagcgttttc

(6761) atgagaaaattacacatgcagacaaattcaggtataattatttgattcatgacgacc
(3317) atgagaaaattacacatgcagacaaattcaggtataattatttgattcatgacgacc
(3298) atgagaaaattacacatgcagacaaattcaggtataattatttgattcatgacgacc
(3317) atgagaaaattacacatgcagacaaattcaggtataattatttgattcatgacgacc

(6818) agcatatagattggtagatagagtgcacatttgtcaaccacaaacgttagcatccca
(3374) agcatatagattggtagatagagtgcacatttgtcaaccacaaacgttagcatccca
(3355) agcatatagattggtagatagagtgcacatttgtcaaccacaaacgttagcatccca
(3374) agcatatagattggtagatagagtgcacatttgtcaaccacaaacgttagcatccca

(6875) gtccggagctatcccctgggttacaggtggcaaatacacaccaaccacaataataag
(3431) gtccggagctatcccctgggttacaggtggcaaatacacaccaaccacaataataag
(3412) gtccggagctatcccctgggttacaggtggcaaatacacaccaaccacaataataag
(3431) gtccggagctatcccctgggttacaggtggcaaatacacaccaaccacaataataag

(6932) ctaatactcttacgtctgtagttggttgccaattactgatcagattacttgaatcac
(3488) ctaatactcttacgtctgtagttggttgccaattactgatcagattacttgaatcac
(3469) ctaatactcttacgtctgtagttggttgccaattactgatcagattacttgaatcac
(3488) ctaatactcttacgtctgtagttggttgccaattactgatcagattacttgaatcac

(6989) aagagcttgttgtgtctaatttgtacaggctatttatatcatgatagctaaagagct
(3545) aagagcttgttgtgtctaatttgtacaggctatttatatcatgatagctaaagagct
(3526) aagagcttgttgtgtctaatttgtacaggctatttatatcatgatagctaaagagct
(3545) aagagcttgttgtgtctaatttgtacaggctatttatatcatgatagctaaagagct

(7046) gctgaaatgagtagcaaggaaacctcaccggccgtcctatactttctctgacatga
(3602) gctgaaatgagtagcaaggaaacctcaccggccgtcctatactttctctgacatga
(3583) gctgaaatgagtagcaaggaaacctcaccggccgtcctatactttctctgacatga
(3602) gctgaaatgagtagcaaggaaacctcaccggccgtcctatactttctctgacatga

(7103) cgacaggacaaccactccaccaccgtgaactgatacaataacaataaagtcctttag
(3659) cgacaggacaaccactccaccaccgtgaactgatacaataacaataaagtcctttag
(3640) cgacaggacaaccactccaccaccgtgaactgatacaataacaataaagtcctttag
(3659) cgacaggacaaccactccaccaccgtgaactgatacaataacaataaagtcctttag
```

FIG. 3o.

```
         *
(7160)  tcccagtaaattagaataggctagaaactaaaatccaacagagagacgaaatcatgg
(3716)  tccaagtaaattagaataggctagaaactaaaatccaacagagagacgaaatcatgg
(3697)  tccaagtaaattagaataggctagaaactaaaatccaacagagagacgaaatcatgg
(3716)  tcccagtaaattagaataggctagaaactaaaatccaacagagagacgaaatcatgg
                     *                    * *
(7217)  ctttggtttgataataactgatacttttgcagGCACGAGGTGGTCGGCGAGGTGGTG
(3773)  ctttggtttggtaataactgatactgtcgcagGCACGAGGTGGTCGGCGAGGTGGTG
(3697)  ctttggtttggtaataactgatactgtcgcagGCACGAGGTGGTCGGCGAGGTGGTG
(3773)  ctttggtttgataataactgatacttttgcagGCACGAGGTGGTCGGCGAGGTGGTG

(7274)  GAGGTCGGGCCCGAGGTGGCCAAGTACGGCGTCGGCGACGTGGTAGGCGTCGGGGTG
(3830)  GAGGTCGGGCCCGAGGTGGCCAAGTACGGCGTCGGCGACGTGGTAGGCGTCGGGGTG
(3754)  GAGGTCGGGCCCGAGGTGGCCAAGTACGGCGTCGGCGACGTGGTAGGCGTCGGGGTG
(3830)  GAGGTCGGGCCCGAGGTGGCCAAGTACGGCGTCGGCGACGTGGTAGGCGTCGGGGTG

(7331)  ATCGTTGGGTGCTGCCGCGAGTGCAGCCCCTGCAAGGCCAACGTTGAGCAGTACTGC
(3887)  ATCGTTGGGTGCTGCCGCGAGTGCAGCCCCTGCAAGGCCAACGTTGAGCAGTACTCC
(3811)  ATCGTTGGGTGCTGCCGCGAGTGCAGCCCCTGCAAGGCCAACGTTGAGCAGTACTGC
(3887)  ATCGTTGGGTGCTGCCGCGAGTGCAGCCCCTGCAAGGCCAACGTTGAGCAGTACTGC
                                                     **
(7388)  AACAAGAAGATCTGGTCATACAACGACGTCTACACTGATGGACGGCCCAC--GCAGG
(3944)  AACAAGAAGATCTGGTCATACAACGACGTCTACACTGATGGACGGCCCACACGCAGG
(3868)  AACAAGAAGATCTGGTCATACAACGACGTCTACACTGATGGACGGCCCAC--CCAGG
(3944)  AACAAGAAGATCTGGTCATACAACGACGTCTACACTGATGGACGGCCCAC--GCAGG

(7445)  GTGGATTCGCCTCCACCATGGTCGTCGACCAGAAgtgagttcttgagactgaaaact
(4001)  GTGGATTCGCCTCCACCATGGTCGTCGACCAGAAgtgagttcttgagactgaaaact
(3923)  GTGGATTCGCCTCCACCATGGTCGTCGACCAGAAgtgagttcttgagactgaaaact
(3999)  GTGGATTCGCCTCCACCATGGTCGTCGACCAGAAgtgagttcttgagactgaaaact

(7500)  aatcttttcactggtttaattattttcagcgttatcttgcatgcagtgttgtagaga
(4058)  aatcttttcactggtttaattattttcagcgttatcttgcatgcagtgttgtagaga
(3980)  aatcttttcactggtttaattattttcagcgttatcttgcatgcagtgttgtagaga
(4057)  aatcttttcactggtttaattattttcagcgttatcttgcatgcagtgttgtagaga
                                    *
(7557)  taataatctctttttttattaaaaaaa-tgtttggtctgaaaaaagctagaaatata
(4115)  taataatctctttttttattaaaaaaa-tgtttggtctgaaaaaagctagaaatata
(4037)  taataatctctttttttattaaaaaaaatgtttggtctgaaaaaagctagaaatata
(4114)  taataatctctttttttattaaaaaaa-tgtttggtctgaaaaaagctagaaatata

(7614)  tagttgaacttcaattatatttcaacttttgcgagaagtggacgagataaggtccaa
(4171)  tagttgaacttcaattatatttcaacttttgcgagaagtggacgagataaggtccaa
(4094)  tagttgaacttcaattatatttcaacttttgcgagaagtggacgagataaggtccaa
(4170)  tagttgaacttcaattatatttcaacttttgcgagaagtggacgagataaggtccaa
```

FIG. 3p.

```
(7670) tccttctagaaaaggtgcaggaaagtatatatatatatatatatatatatatata
(4228) tccttctagaaaaggtgcaggaaagtatatatatatatatatatatatatatata
(4151) tccttctagaaaaggtgcaggaaagtatatatatatatatatatatatatatata
(4227) tccttctagaaaaggtgcaggaaagtatatatatatatatatatatatatatata
                                                           ***
(7727) tatatatatatatatatatatatatatatatatatatatatatatatatatgggg---
(4285) tatatatatatatatatatatatatatatatatatatatatatatatatatgggtat
(4208) tatatatatatatatatatatatatatatatatatatatatatatatatatgggg---
(4284) tatatatatatatatatatatatatatatatatatatatatatatatatatgggg---
       ***
(7784) ---gataaaatatgatcgagaaagtccatcatcatctagctgcaagtcgttgtatgg
(4342) ggggataaaatatgatcgagaaagtccatcatcatctagctgcaagtcgttgtatgg
(4205) ---gataaaatatgatcgagaaagtccatcatcatctagctgcaagtcgttgtatgg
(4338) ---gataaaatatgatcgagaaagtccatcatcatctagctgcaagtcgttgtatgg

(7838) atgtcttatggtgaccaggcaagagtgttgatgtggaaagtacggtatgatttggtg
(4399) atgtcttatggtgaccaggcaagagtgttgatgtggaaagtacggtatgatttggtg
(4259) atgtcttatggtgaccaggcaagagtgttgatgtggaaagtacggtatgatttggtg
(4392) atgtcttatggtgaccaggcaagagtgttgatgtggaaagtacggtatgatttggtg

(7892) tgctttacttgcttgactttgtgaggttgaaccaccaccacagaagccgaatcctca
(4456) tgctttacttgcttgactttgtgaggttgaaccaccaccacagaagccgaatcctca
(4316) tgctttacttgcttgactttgtgaggttgaaccaccaccacagaagccgaatcctca
(4449) tgctttacttgcttgactttgtgaggttgaaccaccaccacagaagccgaatcctca

(7949) cctactcttgattgaagattggccacccaaaccatcaccggttgttgggagaaatga
(4513) cctactcttgattgaagattggccacccaaaccatcaccggttgttgggagaaatga
(4373) cctactcttgattgaagattggccacccaaaccatcaccggttgttgggagaaatga
(4506) cctactcttgattgaagattggccacccaaaccatcaccggttgttgggagaaatga
                               *
(8006) ggataactttctccatcgttcgctccaaaacctgtctacactttagtgtactgtctt
(4570) ggataactttctccatcgttcgctccaaaacctgtctacactttagtgtactgtctt
(4430) ggataactttctccatcgtttgctccaaaacctgtctacactttagtgtactgtctt
(4563) ggataactttctccatcgttcgctccaaaacctgtctacactttagtgtactgtctt

(8063) tttcagtcagtgcgcaaaccacaccacctacctccaacaacattttgagatagcgat
(4627) tttcagtcagtgcgcaaaccacaccacctacctccaacaacattttgagatagcgat
(4487) tttcagtcagtgcgcaaaccacaccacctacctccaacaacattttgagatagcgat
(4620) tttcagtcagtgcgcaaaccacaccacctacctccaacaacattttgagatagcgat

(8120) ttctttttctttttttaaaggcactccgtgtgtgaattatgatagaacagtaactt
(4684) ttctttttctttttttaaaggcactccgtgtgtgaattatgatagaacagtaactt
(4544) ttctttttctttttttaaaggcactccgtgtgtgaattatgatagaacagtaactt
(4677) ttctttttctttttttaaaggcactccgtgtgtgaattatgatagaacagtaactt
```

FIG. 3q.

```
(8177) ttcaagcaatttctttgctgccagtcaattttggaagaaaaaaaaaggcaacctcg
(4741) ttcaagcaatttctttgctgccagtcaattttggaagaaaaaaaaaggcaacctcg
(4601) ttcaagcaatttctttgctgccagtcaattttggaagaaaaaaaaaggcaacctcg
(4734) ttcaagcaatttctttgctgccagtcaattttggaagaaaaaaaaaggcaacctcg

(8234) gtaacacgaatttaggttcctattttgttcttggtaaaaaaaaactaaatacctagt
(4798) gtaacacgaatttaggttcctattttgttcttggtaaaaaaaaactaaatacctagt
(4658) gtaacacgaatttaggttcctattttgttcttggtaaaaaaaaactaaatacctagt
(4791) gtaacacgaatttaggttcctattttgttcttggtaaaaaaaaactaaatacctagt

(8291) tccacgtaagttgatagttaatgcattttgtttcagGTTTGTGGTGAAGATCCCGGC
(4855) tccacgtaagttgatagttaatgcattttgtttcagGTTTGTGGTGAAGATCCCGGC
(4715) tccacgtaagttgatagttaatgcattttgtttcagGTTTGTGGTGAAGATCCCGGC
(4848) tccacgtaagttgatagttaatgcattttgtttcagGTTTGTGGTGAAGATCCCGGC

(8348) GGGTCTGGCTCCGGAGCAAGCGGCCCCGCTGCTGTGCGCTGGCGTGACGGTGTACAG
(4912) GGGTCTGGCTCCGGAGCAAGCGGCGCCGCTGCTGTGCGCTGGCGTGACGGTGTACAG
(4772) GGGTCTGGCTCCGGAGCAAGCGGCGCCGCTGCTGTGCGCTGGCGTGACGGTGTACAG
(4905) GGGTCTGGCTCCGGAGCAAGCGGCGCCGCTGCTGTGCGCTGGCGTGACGGTGTACAG

(8405) CCCGCTGAAGCACTTTGGGCTGACGACCCCGGGCCTCCGTGGCGGCATCCTGGGCCT
(4969) CCCGCTGAAGCACTTTGGGCTGACGACCCCGGGCCTCCGTGGCGGCATCCTGGGCCT
(4829) CCCGCTGAAGCACTTTGGGCTGACGACCCCGGGCCTCCGTGGCGGCATCCTGGGCCT
(4962) CCCGCTGAAGCACTTTGGGCTGACGACCCCGGGCCTCCGTGGCGGCATCCTGGGCCT

(8462) CGGCGGCGTGGGCCACATGGGCGTGAAGGTAGCCAAGGCCATGGGCCACCACGTGAC
(5026) CGGCGGCGTGGGCCACATGGGCGTGAAGGTAGCCAAGGCCATGGGCCACCACGTGAC
(4886) CGGCGGCGTGGGCCACATGGGCGTGAAGGTAGCCAAGGCCATGGGCCACCACGTGAC
(5019) CGGCGGCGTGGGCCACATGGGCGTGAAGGTAGCCAAGGCCATGGGCCACCACGTGAC

(8519) GGTGATCAGCTCGTCGTCCAAGAAGCGCGCGGAGGCAATGGACCACCTCGGCGCGGA
(5083) GGTGATCAGCTCGTCGTCCAAGAAGCGCGCGGAGGCAATGGACCACCTCGGCGCGGA
(4943) GGTGATCAGCTCGTCGTCCAAGAAGCGCGCGGAGGCAATGGACCACCTCGGCGCGGA
(5076) GGTGATCAGCTCGTCGTCCAAGAAGCGCGCGGAGGCAATGGACCACCTCGGCGCGGA

(8576) CGCGTACCTAGTGAGCTCGGACGCCGCGGCCATGGCGGCGGCCGCCGACTCGCTGGA
(5140) CGCGTACCTAGTGAGCTCGGACGCCGCGGCCATGGCGGCGGCCGCCGACTCGCTGGA
(5000) CGCGTACCTAGTGAGCTCGGACGCCGCGGCCATGGCGGCGGCCGCCGACTCGCTGGA
(5133) CGCGTACCTAGTGAGCTCGGACGCCGCGGCCATGGCGGCGGCCGCCGACTCGCTGGA

(8633) CTACATCATCGACACGGTGCCCGTGCACCACCCGCTGGAGCCGTACCTGGCGCTGCT
(5197) CTACATCATCGACACGGTGCCCGTGCACCACCCGCTGGAGCCGTACCTGGCGCTGCT
(5057) CTACATCATCGACACGGTGCCCGTGCACCACCCGCTGGAGCCGTACCTGGCGCTGCT
(5190) CTACATCATCGACACGGTGCCCGTGCACCACCCGCTGGAGCCGTACCTGGCGCTGCT
```

FIG. 3r.

```
(8690) GAAGCTGGACGGCAAGCTCGTGCTGCTGGGCGTCATCGGCGAGCCCCTGAGCTTCGT
(5254) GAAGCTGGACGGCAAGCTCGTGCTGCTGGGCGTCATCGGCGAGCCCCTGAGCTTCGT
(5114) GAAGCTGGACGGCAAGCTCGTGCTGCTGGCCGTCATCGGCGAGCCCCTGAGCTTCGT
(5247) GAAGCTGGACGGCAAGCTCGTGCTGCTGGGCGTCATCGGCGAGCCCCTGAGCTTCGT

(8747) GTCGCCCATGGTGATGCTGGGGCGGAAGGCCATCACGGGGAGCTTCATCGGCAGCAT
(5311) GTCGCCCATGGTGATGCTGGGGCGGAAGGCCATCACGGGGAGCTTCATCGGCAGCAT
(5171) GTCGCCCATGGTGATGCTGGGCGGAAGGCCATCACGGGGAGCTTCATCGGCAGCAT
(5304) GTCGCCCATGGTGATGCTGGGGCGGAAGGCCATCACGGGGAGCTTCATCGGCAGCAT
                                                *
(8804) CGACGAGACCGCTGAGGTGCTTCAGTTCTGCGTCGACAAGGGACTCACCTCCCAGAT
(5368) CGACGAGACCGCTGAGGTGCTTCAGTTCTGCGTCGACAAGGGGCTCACCTCCCAGAT
(5228) CGACGAGACCGCTGAGGTGCTTCAGTTCTGCGTCGACAAGGGGCTCACCTCCCAGAT
(5361) CGACGAGACCGCTGAGGTGCTTCAGTTCTGCGTCGACAAGGGACTCACCTCCCAGAT

(8861) CGAGGTGGTCAAGATGGGGTACGTGAACGAGGCGCTGGAGCGGCTGGAGCGCAACGA
(5425) CGAGGTGGTCAAGATGGGGTACGTGAACGAGGCGCTGGAGCGGCTGGAGCGCAACGA
(5285) CGAGGTGGTCAAGATGGGGTACGTGAACGAGGCGCTGGAGCGGCTGGAGCGCAACGA
(5418) CGAGGTGGTCAAGATGGGGTACGTGAACGAGGCGCTGGAGCGGCTGGAGCGCAACGA

(8918) CGTCCGCTACCGCTTCGTCCTCGACGTCGCCGGTAGCAACGTCGAGGCGGAGGCGGC
(5482) CGTCCGCTACCGCTTCGTCGTCGACGTCGCCGGTAGCAACGTCGAGGCGGAGGCGGC
(5342) CGTCCGCTACCGCTTCGTCGTCGACGTCGCCGGTAGCAACGTCGAGGCGGAGGCGGC
(5475) CGTCCGCTACCGCTTCGTCGTCGACGTCGCCGGTAGCAACGTCGAGGCGGAGGCGGC

(8975) GGCGGCGGATGCGGCCAGCAACTGATGGCACCGCGTCGTCGAGTCGAACCACGTCTG
(5539) GGCGGCGGATGCGGCCAGCAACTGATGGCACCGCGTCGTCGAGTCGAACCACGTCTG
(5399) GGCGGCGGATGCGGCCAGCAACTGATGGCACCGCGTCGTCGAGTCGAACCACGTCTG
(5532) GGCGGCGGATGCGGCCAGCAACTGATGGCACCGCGTCGTCGAGTCGAACCACGTCTG

(9032) TGCGCCGCGTGCAACGTTCGTTCGGGTCGAGTCTGCGTGCAACGTTCTGCTTCCTTT
(5596) TGCGCCGCGTGCAACGTTCGTTCGGGTCGAGTCTGCGTGCAACGTTCTGCTTCCTTT
(5456) TGCGCCGCGTGCAACGTTCGTTCGGGTCGAGTCTGCGTGCAACGTTCTGCTTCCTTT
(5589) TGCGCCGCGTGCAACGTTCGTTCGGGTCGAGTCTGCGTGCAACGTTCTGCTTCCTTT

(9089) ACTAGTTGTTGTCTTTCCGCCTTCTTGCCGTTCTGTTCTGGGCTTTGAGATGAGACG
(5653) ACTAGTTGTTGTCTTTCCGCCTTCTTGCCGTTCTGTTCTGGGCTTTGAGATGAGACG
(5513) ACTAGTTGTTGTCTTTCCGCCTTCTTGCCGTTCTGTTCTGGGCTTTGAGATGAGACG
(5646) ACTAGTTGTTGTCTTTCCGCCTTCTTGCCGTTCTGTTCTGGGCTTTGAGATGAGACG

(9146) ATGGATGGTCAGTTTTTAATGTCAGACTGAATAACTACGTATAGTACTGTAGTATTA
(5710) ATGGATGGTCAGTTTTTAATGTCAGACTGAATAACTACGTATAGTACTGTAGTATTA
(5570) ATGGATGGTCAGTTTTTAATGTCAGACTGAATAACTACGTATAGTACTGTAGTATTA
(5703) ATGGATGGTCAGTTTTTAATGTCAGACTGAATAACTACGTATAGTACTGTAGTATTA
```

FIG. 3s.

```
(9203) CTCGGAGTACGCCAGAATGTGGTGTGGTGTCAGTCTCACCAGCAATCTGGATTTGCC
(5767) CTCGGAGTACGCCAGAATGTGGTGTGGTGTCAGTCTCACCAGCAATCTGGATTTGCC
(5627) CTCGGAGTACGCCAGAATGTGGTGTGGTGTCAGTCTCACCAGCAATCTGGATTTGCC
(5760) CTCGGAGTACGCCAGAATGTGGTGTGGTGTCAGTCTCACCAGCAATCTGGATTTGCC

(9260) AAGTGTTTCTATTTTTTCTTCGGTTTGCCCGAGTGTTTGTGATTGTTAAGAACTACG
(5824) AAGTGTTTCTATTTTTTCTTCGGTTTGCCCGAGTGTTTGTGATTGTTAAGAACTACG
(5684) AAGTGTTTCTATTTTTTCTTCGGTTTGCCCGAGTGTTTGTGATTGTTAAGAACTACG
(5817) AAGTGTTTCTATTTTTTCTTCGGTTTGCCCGAGTGTTTGTGATTGTTAAGAACTACG

(9317) TTATTACGGATCGTCAAAtccgttcccttctgtctcgtctatag
(5881) TTATTACGGATCGTCAAAtccgttcccttctgtctcgtctatag
(5741) TTATTACGGATCGTCAAAtccgttcccttctgtctcgtctatag
(5874) TTATTACGGATCGTCAAAtccgttcccttctgtctcgtctatag
```

FIG. 4a.

```
DASbm1 cDNA (SEQ ID NO:24)     (1) GTGCGGGCTCGTCTCCATCGCCCGCCACCC
515Dbm1 cDNA (SEQ ID NO:2)     (1) GTGCGGGCTCGTCTCCATCGCCCGCCACCC
6XN442 cDNA (SEQ ID NO:5)      (1) GTGCGGGCTCGTCTCCATCGCCCGCCACCC
B73 cDNA (SEQ ID NO:8)         (1) GTGCGGGCTCGTCTCCATCGCCCGCCACCC

(31)    GCTCCGTCGTCGTCGTCCCCGCCGCGCCGATCCCGAATCGAATGGGGAGCCTGGCGT
(31)    GCTCCGTCGTCGTCGTCCCCGCCGCGCCGATCCCGAATCGAATGGGGAGCCTGGCGT
(31)    GCTCCGTCGTCGTCGTCCCCGCCGCGCCGATCCCGAATCGAATGGGGAGCCTGGCGT
(31)    GCTCCGTCGTCGTCGTCCCCGCCGCGCCGATCCCGAATCGAATGGGGAGCCTGGCGT

(88)    CCGAGAGGAAGGTGGTCGGGTGGGCCGCCAGGGACGCCACCGGACACCTCTCCCCCT
(88)    CCGAGAGGAAGGTGGTCGGGTGGGCCGCCAGGGACGCCACCGGACACCTCTCCCCCT
(88)    CCGAGAGGAAGGTGGTCGGGTGGGCCGCCAGGGACGCCACCGGACACCTCTCCCCCT
(88)    CCGAGAGGAAGGTGGTCGGGTGGGCCGCCAGGGACGCCACCGGACACCTCTCCCCCT

(145)   ACTCCTACACCCTCAGCCTAGGCCATGGAGGGGGTATCATCAGCTCCAGAAATGGAC
(145)   ACTCCTACACCCTC-------------------------------------------
(145)   ACTCCTACACCCTC-------------------------------------------
(145)   ACTCCTACACCCTC-------------------------------------------

(202)   GAGGCTATCTCAACTGACCAATCAAGCAGATCAACAAAAAGAAGGGCTAAAGTGTGG
(159)   ---------------------------------------------------------
(159)   ---------------------------------------------------------
(159)   ---------------------------------------------------------

(259)   GATCATGTTGATTCAGAGCTAATAGATGGGAAAGACAAGGCGGTTTGCAAATACTGT
(159)   ---------------------------------------------------------
(159)   ---------------------------------------------------------
(159)   ---------------------------------------------------------

(316)   AAGGCCCACTTATCTTCTGCTGCGGGTAAAGGCTAAGGAGTTCCTTGGTGCTTCCGG
(159)   ---------------------------------------------------------
(159)   ---------------------------------------------------------
(159)   ---------------------------------------------------------

(373)   TGACAAGCGAAAGGAAGTCAATTAACTCTGAATCAGTGGTTCTGCTGCAAGGTTGCA
(159)   ---------------------------------------------------------
(159)   ---------------------------------------------------------
(159)   ---------------------------------------------------------

(430)   TGCAGGTTACACACAACATTTTATTGAATGGAAAGAGGACACTCGGTGACCACAAGA
(159)   ---------------------------------------------------------
(159)   ---------------------------------------------------------
(159)   ---------------------------------------------------------
```

FIG. 4b.

```
(487)  TCATCAGATGATCATTTGTTGAGCTCTGGAACTAAATCCTCTCCGCAGGTGGTAACC
(159)  ---------------------------------------------------------
(159)  ---------------------------------------------------------
(159)  ---------------------------------------------------------

(544)  AGGCGGGTTCCCATCCGAGTTCCGAGGAACACAGGCCCTGAAGATGTGGTGGTGAAG
(159)  ------------------------AGGAACACAGGCCCTGAAGATGTGGTGGTGAAG
(159)  ------------------------AGGAACACAGGCCCTGAAGATGTGGTGGTGAAG
(159)  ------------------------AGGAACACAGGCCCTGAAGATGTGGTGGTGAAG

(601)  GTGCTCTACTGCGGGATCTGCCACACGGACATCCACCAGGCCAAGAACCACCTCGGG
(192)  GTGCTCTACTGCGGGATCTGCCACACGGACATCCACCAGGCCAAGAACCACCTCGGG
(192)  GTGCTCTACTGCGGGATCTGCCACACGGACATCCACCAGGCCAAGAACCACCTCGGG
(192)  GTGCTCTACTGCGGGATCTGCCACACGGACATCCACCAGGCCAAGAACCACCTCGGG

(658)  GCTTCAAAGTATCCTATGGTCCCTGGGCACGAGGTGGTCGGCGAGGTGGTGGAGGTC
(249)  GCTTCAAAGTATCCTATGGTCCCTGGGCACGAGGTGGTCGGCGAGGTGGTGGAGGTC
(249)  GCTTCAAAGTATCCTATGGTCCCTGGGCACGAGGTGGTCGGCGAGGTGGTGGAGGTC
(249)  GCTTCAAAGTATCCTATGGTCCCTGGGCACGAGGTGGTCGGCGAGGTGGTGGAGGTC

(715)  GGGCCCGAGGTGGCCAAGTACGGCGTCGGCGACGTGGTAGGCGTCGGGGTGATCGTT
(306)  GGGCCCGAGGTGGCCAAGTACGGCGTCGGCGACGTGGTAGGCGTCGGGGTGATCGTT
(306)  GGGCCCGAGGTGGCCAAGTACGGCGTCGGCGACGTGGTAGGCGTCGGGGTGATCGTT
(306)  GGGCCCGAGGTGGCCAAGTACGGCGTCGGCGACGTGGTAGGCGTCGGGGTGATCGTT

(772)  GGGTGCTGCCGCGAGTGCAGCCCCTGCAAGGCCAACGTTGAGCAGTACTGCAACAAG
(363)  GGGTGCTGCCGCGAGTGCAGCCCCTGCAAGGCCAACGTTGAGCAGTACTGCAACAAG
(363)  GGGTGCTGCCGCGAGTGCAGCCCCTGCAAGGCCAACGTTGAGCAGTACTGCAACAAG
(363)  GGGTGCTGCCGCGAGTGCAGCCCCTGCAAGGCCAACGTTGAGCAGTACTGCAACAAG
                                                   **
(829)  AAGATCTGGTCATACAACGACGTCTACACTGATGGACGGCCCAC--GCAGGGTGGAT
(420)  AAGATCTGGTCATACAACGACGTCTACACTGATGGACGGCCCACACGCAGGGTGGAT
(420)  AAGATCTGGTCATACAACGACGTCTACACTGATGGACGGCCCAC--GCAGGGTGGAT
(420)  AAGATCTGGTCATACAACGACGTCTACACTGATGGACGGCCCAC--GCAGGGTGGAT

(884)  TCGCCTCCACCATGGTCGTCGACCAGAAGTTTGTGGTGAAGATCCCGGCGGGTCTGG
(477)  TCGCCTCCACCATGGTCGTCGACCAGAAGTTTGTGGTGAAGATCCCGGCGGGTCTGG
(475)  TCGCCTCCACCATGGTCGTCGACCAGAAGTTTGTGGTGAAGATCCCGGCGGGTCTGG
(475)  TCGCCTCCACCATGGTCGTCGACCAGAAGTTTGTGGTGAAGATCCCGGCGGGTCTGG

(941)  CTCCGGAGCAAGCGGCGCCGCTGCTGTGCGCTGGCGTGACGGTGTACAGCCCGCTGA
(534)  CTCCGGAGCAAGCGGCGCCGCTGCTGTGCGCTGGCGTGACGGTGTACAGCCCGCTGA
(532)  CTCCGGAGCAAGCGGCGCCGCTGCTGTGCGCTGGCGTGACGGTGTACAGCCCGCTGA
(532)  CTCCGGAGCAAGCGGCGCCGCTGCTGTGCGCTGGCGTGACGGTGTACAGCCCGCTGA
```

FIG. 4c.

```
(998)   AGCACTTTGGGCTGACGACCCCGGGCCTCCGTGGCGGCATCCTGGGCCTCGGCGGCG
(591)   AGCACTTTGGGCTGACGACCCCGGGCCTCCGTGGCGGCATCCTGGGCCTCGGCGGCG
(589)   AGCACTTTGGGCTGACGACCCCGGGCCTCCGTGGCGGCATCCTGGGCCTCGGCGGCG
(589)   AGCACTTTGGGCTGACGACCCCGGGCCTCCGTGGCGGCATCCTGGGCCTCGGCGGCG

(1055)  TGGGCCACATGGGCGTGAAGGTAGCCAAGGCCATGGGCCACCACGTGACGGTGATCA
(648)   TGGGCCACATGGGCGTGAAGGTAGCCAAGGCCATGGGCCACCACGTGACGGTGATCA
(646)   TGGGCCACATGGGCGTGAAGGTAGCCAAGGCCATGGGCCACCACGTGACGGTGATCA
(646)   TGGGCCACATGGGCGTGAAGGTAGCCAAGGCCATGGGCCACCACGTGACGGTGATCA

(1112)  GCTCGTCGTCCAAGAAGCGCCCGGAGGCAATGGACCACCTCGGCGCGGACGCGTACC
(705)   GCTCGTCGTCCAAGAAGCGCGCGGAGGCAATGGACCACCTCGGCGCGGACGCGTACC
(703)   GCTCGTCGTCCAAGAAGCGCGCGGAGGCAATGGACCACCTCGGCGCGGACGCGTACC
(703)   GCTCGTCGTCCAAGAAGCGCGCGGAGGCAATGGACCACCTCGGCGCGGACGCGTACC

(1169)  TAGTGAGCTCGGACGCCGCGGCCATGGCGGCGGCCGCCGACTCGCTGGACTACATCA
(762)   TAGTGAGCTCGGACGCCGCGGCCATGCCGGCGGCCGCCGACTCGCTGGACTACATCA
(760)   TAGTGAGCTCGGACGCCGCGGCCATGGCGGCGGCCGCCGACTCGCTGGACTACATCA
(760)   TAGTGAGCTCGGACGCCGCGGCCATGGCGGCGGCCGCCGACTCGCTGGACTACATCA

(1226)  TCGACACGGTGCCCGTGCACCACCCGCTGGAGCCGTACCTGGCGCTGCTGAAGCTGG
(819)   TCGACACGGTGCCCGTGCACCACCCGCTGGAGCCGTACCTGGCGCTGCTGAAGCTGG
(817)   TCGACACGGTGCCCGTGCACCACCCGCTGGAGCCGTACCTGGCGCTGCTGAAGCTGG
(817)   TCGACACGGTGCCCGTGCACCACCCGCTGGAGCCGTACCTGGCGCTGCTGAAGCTGG

(1283)  ACGGCAAGCTCGTGCTGCTGGGCGTCATCGGCCAGCCCCTGAGCTTCGTGTCGCCCA
(876)   ACGGCAAGCTCGTGCTGCTGGGCGTCATCGGCGAGCCCCTGAGCTTCGTGTCGCCCA
(874)   ACGGCAAGCTCGTGCTGCTGGGCGTCATCGGCCAGCCCCTGAGCTTCGTGTCGCCCA
(874)   ACGGCAAGCTCGTGCTGCTGGGCGTCATCGGCGAGCCCCTGAGCTTCGTGTCGCCCA

(1340)  TGGTGATGCTGGGGCGGAAGGCCATCACGGGGAGCTTCATCGGCAGCATCGACGAGA
(933)   TGGTGATGCTGGGGCGGAAGGCCATCACGGGGAGCTTCATCGGCAGCATCGACGAGA
(931)   TGGTGATGCTGGGGCGGAAGGCCATCACGGGGAGCTTCATCGGCAGCATCGACGAGA
(931)   TGGTGATGCTGGGGCGGAAGGCCATCACGGGGAGCTTCATCGGCAGCATCGACGAGA
                                                *
(1397)  CCGCTGAGGTGCTTCAGTTCTGCGTCGACAAGGGACTCACCTCCCAGATCGAGGTGG
(990)   CCGCTGAGGTGCTTCAGTTCTGCGTCGACAAGGGGCTCACCTCCCAGATCGAGGTGG
(988)   CCGCTGAGGTGCTTCAGTTCTGCGTCGACAAGGGGCTCACCTCCCAGATCGAGGTGG
(988)   CCGCTGAGGTGCTTCAGTTCTGCGTCGACAAGGGACTCACCTCCCAGATCGAGGTGG

(1454)  TCAAGATGGGGTACGTGAACGAGGCGCTGGAGCGGCTGGAGCGCAACGACGTCCGCT
(1047)  TCAAGATGGGGTACGTGAACGAGGCGCTGGAGCGGCTGGAGCGCAACGACGTCCGCT
(1045)  TCAAGATGGGGTACGTGAACGAGGCGCTGGAGCGGCTGGAGCGCAACGACGTCCGCT
(1045)  TCAAGATGGGGTACGTGAACGAGGCGCTGGAGCGGCTGGAGCGCAACGACGTCCGCT
```

FIG. 4d.

```
(1511) ACCGCTTCGTCGTCGACGTCGCCGGTAGCAACGTCGAGGCGGAGGCGGCGGCGGCGG
(1104) ACCGCTTCGTCGTCGACGTCGCCGGTAGCAACGTCGAGGCGGAGGCGGCGGCGGCGG
(1102) ACCGCTTCGTCGTCGACGTCGCCGGTAGCAACGTCGAGGCGGAGGCGGCGGCGGCGG
(1102) ACCGCTTCGTCGTCGACGTCGCCGGTAGCAACGTCGAGGCGGAGGCGGCGGCGGCGG

(1568) ATGCGGCCAGCAACTGATGGCACCGCGTCGTCGAGTCGAACCACGTCTGTGCGCCGC
(1161) ATGCGGCCAGCAACTGATGGCACCGCGTCGTCGAGTCGAACCACGTCTGTGCGCCGC
(1159) ATGCGGCCAGCAACTGATGGCACCGCGTCGTCGAGTCGAACCACGTCTGTGCGCCGC
(1159) ATGCGGCCAGCAACTGATGGCACCGCGTCGTCGAGTCGAACCACGTCTGTGCGCCGC

(1625) GTGCAACGTTCGTTCGGGTCGAGTCTGCGTGCAACGTTCTGCTTCCTTTACTAGTTG
(1218) GTGCAACGTTCGTTCGGGTCGAGTCTGCGTGCAACGTTCTGCTTCCTTTACTAGTTG
(1216) GTGCAACGTTCGTTCGGGTCGAGTCTGCGTGCAACGTTCTGCTTCCTTTACTAGTTG
(1216) GTGCAACGTTCGTTCGGGTCGAGTCTGCGTGCAACGTTCTGCTTCCTTTACTAGTTG

(1682) TTGTCTTTCCGCCTTCTTGCCGTTCTGTTCTGGGCTTTGAGATGAGACGATGGATGG
(1275) TTGTCTTTCCGCCTTCTTGCCGTTCTGTTCTGGGCTTTGAGATGAGACGATGGATGG
(1273) TTGTCTTTCCGCCTTCTTGCCGTTCTGTTCTGGGCTTTGAGATGAGACGATGGATGG
(1273) TTGTCTTTCCGCCTTCTTGCCGTTCTGTTCTGGGCTTTGAGATGAGACGATGGATGG

(1739) TCAGTTTTTAATGTCAGACTGAATAACTACGTATAGTACTGTAGTATTACTCGGAGT
(1332) TCAGTTTTTAATGTCAGACTGAATAACTACGTATAGTACTGTAGTATTACTCGGAGT
(1330) TCAGTTTTTAATGTCAGACTGAATAACTACGTATAGTACTGTAGTATTACTCGGAGT
(1330) TCAGTTTTTAATGTCAGACTGAATAACTACGTATAGTACTGTAGTATTACTCGGAGT

(1796) ACGCCAGAATGTGGTGTGGTGTCAGTCTCACCAGCAATCTGGATTTGCCAAGTGTTT
(1389) ACGCCAGAATGTGGTGTGGTGTCAGTCTCACCAGCAATCTGGATTTGCCAAGTGTTT
(1387) ACGCCAGAATGTGGTGTGGTGTCAGTCTCACCAGCAATCTGGATTTGCCAAGTGTTT
(1387) ACGCCAGAATGTGGTGTGGTGTCAGTCTCACCAGCAATCTGGATTTGCCAAGTGTTT

(1853) CTATTTTTTCTTCGGTTTGCCCGAGTGTTTGTGATTGTTAAGAACTACGTTATTACG
(1446) CTATTTTTTCTTCGGTTTGCCCGAGTGTTTGTGATTGTTAAGAACTACGTTATTACG
(1444) CTATTTTTTCTTCGGTTTGCCCGAGTGTTTGTGATTGTTAAGAACTACGTTATTACG
(1444) CTATTTTTTCTTCGGTTTGCCCGAGTGTTTGTGATTGTTAAGAACTACGTTATTACG

(1910) GATCGTCAAA
(1503) GATCGTCAAA
(1501) GATCGTCAAA
(1501) GATCGTCAAA
```

FIG. 5.

```
6XN442 CAD2 (SEQ ID NO:6)      (1) MGSLASERKVVGWAARDATGHLSPYSYTLR
515Dbm1 CAD2 (SEQ ID NO:3)     (1) MGSLASERKVVGWAARDATGHLSPYSYTLR
DASbm1 CAD2 (SEQ ID NO:25)     (1) MGSLASERKVVGWAARDATGHLSPYSYTLS

(31)  NTGPEDVVVKVLYCGICHTDIHQAKNHLGASKYPMVPGHEVVGEVVEVGPEVAKYGVG
(31)  NTGPEDVVVKVLYCGICHTDIHQAKNHLGASKYPMVPGHEVVGEVVEVGPEVAKYGVG
(31)  LGHGGGIISSRNGRGYLN----------------------------------------

(89)  DVVGVGVIVGCCRECSPCKANVEQYCNKKIWSYNDVYTDGRPTQGGFASTMVVDQKFV
(89)  DVVGVGVIVGCCRECSPCKANVEQYCNKKIWSYNDVYTDGRPTRRVDSPPPWSSTRSL
(48)  ----------------------------------------------------------

(148) VKIPAGLAPEQAAPLLCAGVTVYSPLKHFGLTTPGLRGGILGLGGVGHMGVKVAKAMG
(148) W---------------------------------------------------------
(48)  ----------------------------------------------------------

(206) HHVTVISSSSKKRAEAMDHLGADAYLVSSDAAAMAAAADSLDYIIDTVPVHHPLEPYL
(148) ----------------------------------------------------------
(48)  ----------------------------------------------------------

(264) ALLKLDGKLVLLGVIGEPLSFVSPMVMLGRKAITGSFIGSIDETAEVLQFCVDKGLTS
(148) ----------------------------------------------------------
(48)  ----------------------------------------------------------

(322) QIEVVKMGYVNEALERLERNDVRYRFVVDVAGSNVEAEAAAADAASN
(148) -----------------------------------------------
(48)  -----------------------------------------------
```

GENE AND VARIATIONS ASSOCIATE WITH BM1 PHENOTYPE, MOLECULAR MARKERS, AND THEIR USE

CROSS-REFERENCE TO RELATED APPLICATION

This application claims the benefit of U.S. Provisional Patent Application Ser. No. 61/429,390, filed Jan. 3, 2011, the disclosure of which is hereby incorporated herein in its entirety by this reference.

FIELD OF THE DISCLOSURE

The present disclosure relates to a maize brown midrib (bmr) phenotype. In particular embodiments, this disclosure concerns particular altered cinnamyl alcohol dehydrogenase 2 (cad2) genes in maize, which altered genes contribute to the bm1 phenotype in some maize varieties, nucleic acid molecules comprising an altered cad2 gene, and/or protein products resulting from the translation of such nucleic acid molecules.

BACKGROUND

Lignins are universal components in plants that form cross-links with carbohydrates, such as hemicelluloses in the cell wall. Lignin and cellulose are the two predominant components of the plant cell wall. The plant cell wall provides a natural barrier against the extracellular environment. Many studies have demonstrated that one of the responses of plants to biotic stresses (e.g., pathogenic infection) or abiotic stresses (e.g., drought, mechanical stress, etc.) consists of reinforcement of the plant cell wall, in particular by increasing the lignin content in the plant cell wall. Many agronomical or industrial applications concern desired plant products (e.g., products used in paper production, silage production, and the production of energy, for example, in the form of biofuels), the yields of which are directly linked to the content and/or composition of lignin in the plant cell wall.

Lignin polymers limit the digestibility of the fiber in the corn plant. Lignin polymers lower fiber digestion in ruminants, and the degree of lignifications may be inversely proportional to forage crop digestibility. Cherney et al. (1991) Adv. Agron. 46:157-98. Modulation of lignin content and composition may be desirable to increase the digestibility of forage. Lignin content modulation may also be desirable, e.g., to reinforce plant walls, and thereby improve resistance to stresses; or conversely to weaken the plant wall in order to facilitate the extraction of cellulose or other chemical compounds. Baucher et al. (1998) Plant Mol. Biol. 39:437-47.

It is, however, difficult to know how to modify the lignin biosynthesis pathway, and to predict what the consequences of modifications will be. This is at least in part because the lignin biosynthesis pathway is a complex pathway involving a large number of enzymatic reactions. See, e.g., Dixon et al. (2001) Phytochemistry 57(7):1069-84. Possible mechanisms by which the pathway may be altered physiologically, for example, to compensate for a change introduced by a modification in the pathway, are not known.

Lignin is an insoluble polymer of 3 monomers of alcohols or monolignols: p-coumaryl alcohol (H subunits), coniferyl alcohol (G subunits), and sinapyl alcohol (S subunits), that are derived from the phenylpropanoid pathway. Neish (1968) Constitution and Biosynthesis of Lignin, eds. New York, Springer Verlag 1-43. Each type of subunit can form a variety of bonds with others, and thereby constitute lignin. Other bonds may also be established with other parietal compounds (e.g., polysaccharides and proteins) so as to form a complex three-dimensional network.

Steps in the complex lignin production pathway include hydroxylation, O-methylation of aromatic rings, and conversion of a carboxyl side chain to an alcohol function. The current hypothesis for the monolignol biosynthesis pathway includes successive hydroxylation and O-methylation reactions at various levels of oxidation of the side chains in a metabolic network, thereby resulting in the formation of S and G subunits. The enzymes of the network include caffeic acid 3-O-methyltransferase (COMT); hydroxyxinamate coenzyme A ligases (4CL); cytochrome P450-dependent ferulate 5-hydroxylases (F5Hs); and several isoforms of cinnamoyl CoA reductase (CCR) and of cinnamyl alcohol dehydrogenase (CAD).

For several years, attempts have been made to modify the lignin content and composition of plants by over-expressing or under-expressing one or more genes of the lignin biosynthesis pathway. Anterola and Lewis (2002) Phytochemistry 61:221-94. Though various strategies have been imagined, the over-expression or under-expression of one or more enzymes in the lignin biosynthesis pathway does not always give reliable and predictable results.

Another strategy consists of using, in selection schemes, mutants of a targeted gene in the lignin biosynthesis pathway. Plants containing a brown midrib (bmr) mutation exhibit altered lignin composition and digestibility. In corn, at least four independent brown midrib mutations have been identified. Kuc et al. (1968) Phytochemistry 7:1435-6. These mutations, termed “bm1, bm2, bm3, and bm4,” all exhibit decreased lignin content when compared to control corn. Brown midrib corn plants are characterized by a brown pigmentation in the leaf midrib at the V4 to V6 stage and a light brown coloration of the pith after tasselling. One characterized bmr mutation is an insertion mutation in the COMT enzyme (bm3).

Mature bm1 maize plants have a lignin content that is reduced by 10-20%, a slight decrease in ferulic acid esters, and a substantially reduced content (~40%) of p-coumaric esters and ferulic acid esters. Provan et al. (1997) J. Agric. Food 73:133-42; Barriére et al. (2004) Comptes Rendus Biologie 327:847-60. The frequency of p-hydroxyphenyl, guaiacyl, and syringyl thioacidolysis monomers is similar in bm1 and wild-type plants, showing that the bm1 mutation does not specifically affect a single type of lignin subunit. Guillaumie et al. (2007) Planta 226(1):235-50. Lignins of bm1 plants do appear to be substantially enriched in carbon-carbon inter-subunit linkages (Halpin et al. (1998) Plant J. 14(5):545-53; Barriére et al. (2004), supra), and bm1 lignins have substantial incorporation of coniferaldehyde and, to a lesser extent, of sinapaldehyde. Kim et al. (2002) J. Biol. Chem. 277:47412-9.

Agriculturally important uses of corn (maize) include silage. Silage is fermented, high-moisture fodder that can be fed to ruminants. It is fermented and stored in a process called ensilage or silaging, and is usually made from corn or other grass crops, including sorghum or other cereals, using the entire green plant. Bulk silage is commonly fed to dairy cattle, while baled silage tends to be used for beef cattle, sheep, and horses. Since silage goes through a fermentation process, energy is used by fermentative bacteria to produce volatile fatty acids, such as acetate, propionate, lactate, and butyrate, which preserve the forage. The result is that the silage is lower in energy than the original forage, since the fermentative bacteria use some of the carbohydrates to produce the volatile fatty acids. Corn silage is a popular forage for ruminant animals because it is high in energy and digestibility and is easily adapted to mechanization from the stand-crop to time of feeding. Corn silage generally is slightly brown to dark green in color, and has a light, pleasant smell.

The reduced lignin in brown midrib corn (bmr corn) results in silage with fiber that is more digestible than normal corn and exhibits an improved rate of biofuel conversion. Feeding bmr corn silage to lactating dairy cows has been shown to increase dry matter intake (DMI) and milk yield. Grant et al. (1995) J. Dairy Sci. 78:1970-80; Oba and Allen (2000) J. Dairy Sci. 83:1333-41; Oba and Allen (1999) J. Dairy Sci. 82:135-42. However, bmr corn silage reduced average daily gain and feed efficiency (G:F) in beef cows, compared to corn silage from a conventional corn variety. Tjardes et al. (2000) J. Anim. Sci. 78:2957-65. Brown midrib hybrid corn lines are also frequently found to be low yielding. Brown midrib hybrid corn has also typically been associated with forage lodging and lack of standability.

BRIEF SUMMARY OF THE DISCLOSURE

Described herein are nucleic acid molecules comprising a mutant cad2 gene that contributes to the bm1 phenotype in corn (maize). Also described are molecular markers that are linked to or that reside within a mutant maize cad2 gene. Surprisingly, the complicated pathway of lignin biosynthesis is apparently altered in the presence of a mutant cad2 gene, such that plants containing a mutant cad2 gene have lignin levels that are lower than those found in wild-type plants. The characterization of mutant cad2 genes and identification of markers linked to mutant cad2 genes may greatly facilitate the development and deployment of reduced lignin phenotypes in plant germplasms. In some embodiments, markers that are linked to or that reside within a mutant maize cad2 gene, or a mutant maize cad2 gene sequence itself, may be used to introduce a mutant maize cad2 gene into other organisms, for example, plants, yeast, and prokaryotes.

In particular embodiments, a mutant cad2 gene according to the disclosure may comprise a nucleotide sequence encoding a truncated CAD2 protein. For example, a mutant cad2 gene comprising an insertion mutation in an exon (e.g., exon 3) or an intron (e.g., intron 1) of the cad2 gene may introduce a premature STOP codon that results in a shorter gene product. In some embodiments, a mutant cad2 gene according to the disclosure may comprise a naturally-occurring mutation in one or more maize lines. In some embodiments, a mutant cad2 gene is cloned from a known bmr corn variety; e.g., 515Dbm1. In other embodiments, a mutant cad2 gene is cloned from a previously unknown bmr corn variety; e.g., DASbm1. When expressed in a plant, a mutant cad2 gene according to the disclosure may result in a phenotype in the plant; for example, reduced levels of cad2 RNA in tissues of the plant, and/or reduced lignin content in tissues of the plant.

Also described herein are methods of using nucleic acid molecular markers that are linked to or that reside within a mutant maize cad2 gene according to the disclosure, for example and without limitation: to identify plants having a reduced lignin phenotype; to introduce a mutant maize cad2 gene to new plant genotypes (e.g., through marker-assisted breeding or genetic transformation); to differentiate between wild-type CAD2 genes and particular mutant cad2 genes according to the disclosure; and to produce plants and plant seeds from crosses of a first plant comprising nucleic acid molecular markers that are linked to or that reside within a mutant maize cad2 gene according to the disclosure and a second plant optionally carrying a mutant maize cad2 gene. In some embodiments, a mutant maize cad2 gene is engineered into plant species other than maize.

Further described are means for producing a genetically modified plant (e.g., maize) comprising a mutant maize cad2 gene, and means for identifying plants (e.g., maize) carrying a mutant maize cad2 gene. A means for producing a genetically modified plant comprising a mutant maize cad2 gene is a marker that is linked to or that resides within a mutant maize cad2 gene according to the disclosure. A means for identifying plants carrying a mutant maize cad2 gene is a probe that specifically hybridizes to a marker that is linked to or that resides within a mutant maize cad2 gene according to the disclosure.

Methods are disclosed for increasing the meat quantity of a silage-fed animal, for example by increasing the gain to feed ratio (G:F) for corn silage. In some embodiments, a method for increasing the meat quantity of a silage-fed animal may comprise providing plant material obtained from maize comprising a mutant maize cad2 gene according to the disclosure, using the plant material for the production of corn silage, and incorporation of the corn silage in a finishing ration for feeding to a ruminant. Thus, meat and meat products produced from an animal fed a finishing ration according to the disclosure or according to a method the disclosure are also provided.

The foregoing and other features will become more apparent from the following detailed description of several embodiments, which proceeds with reference to the accompanying figures.

BRIEF DESCRIPTION OF THE FIGURES

FIG. 1 includes a diagram showing the relative lengths and positions of seven overlapping 515Dbm1 cad2 PCR fragments. FIG. 1 also includes a diagram showing the relative lengths and positions of thirteen overlapping DASbm1 cad2 PCR fragments.

FIG. 3 includes an alignment of ZmCAD2 genomic sequences, using a B73 sequence from public accession AC230031. 15 SNPs and 8 insertion/deletions are identified, as well as a transposon insertion in DASbm1. An AC insertion is present only in the 515Dbm1 mutant in exon 3. Exons are shown in uppercase font. Introns and a promoter region are shown in lowercase font.

FIG. 4 includes an alignment of ZmCAD2 cDNA sequences. Shown is a DASbm1 ZmCAD2 cDNA sequence, wherein a partial sequence was amplified by primer pair CVF/CVR (underlined), and the remainder of the full-length sequence is predicted. Also shown are full-length predicted ZmCAD2 cDNA sequences from 515Dbm1 and wild-type 6XN442 (underlined). DASbm1 cDNA contains a 409 bp insertion.

FIG. 5 includes an alignment of predicted ZmCAD2 protein sequences, illustrating that CAD2 from 515Dbm1 only has 147 amino acids due to an AC insertion that creates a frame-shift and premature STOP codon. CAD2 from DASbm1 only has 48 amino acids, compared to 367 amino acids in CAD2 from 6XB442. Regions of identity are shown in bold font. The B73 CAD2 amino acid sequence is identical to that of 6XN422 CAD2, and is therefore not shown.

SEQUENCE LISTING

Figure 2:
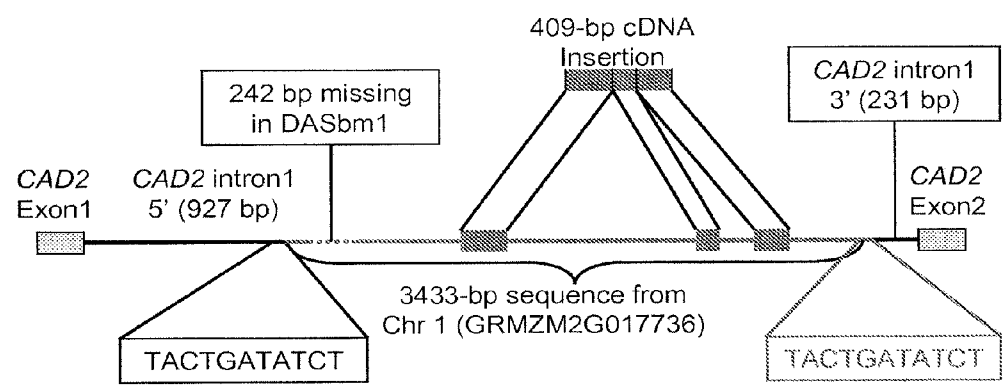
FIG. 2 includes a diagram showing the genomic structure of the insertion in DASbm1 cad2. Only the first two endogenous exons of cad2 are shown. A duplicated 11 bp sequence (TACTGATATCT) (SEQ ID NO: 42) in the DASbm1 transposon insertion from the first intron of CAD2 is also shown.

The nucleic acid sequences listed in the accompanying sequence listing are shown using standard letter abbreviations for nucleotide bases, as defined in 37 C.F.R. §1.822. Only one strand of each nucleic acid sequence is shown, but the complementary strand is understood to be included by any reference to the displayed strand. In the accompanying sequence listing:

SEQ ID NO:1 shows a 5924 bp genomic sequence of 515Dbm1 CAD2.

SEQ ID NO:2 shows a 1512 bp predicted cDNA sequence of 515Dbm1 CAD2.

SEQ ID NO:3 shows a 147 amino acid predicted truncated protein sequence of 515Dbm1 CAD2.

SEQ ID NO:4 shows a 5898 bp genomic sequence of 6XN442 CAD2.

SEQ ID NO:5 shows a 1510 bp predicted cDNA sequence of 6XN442 CAD2.

SEQ ID NO:6 shows a 367 amino acid predicted protein sequence of 6XN442 CAD2.

SEQ ID NO:7 shows a 5916 bp genomic sequence of B73 CAD2.

SEQ ID NO:8 shows a 1510 bp predicted cDNA sequence of B73 CAD2.

SEQ ID NOs:9-22 show forward and reverse primers used to amplify seven overlapping CAD2 fragments from both the 515Dbm1 mutant and wild-type 6XN442 corn.

SEQ ID NO:23 shows a 9417 bp genomic sequence of DASbm1 CAD2.

SEQ ID NO:24 shows a partial cDNA sequence of DASbm1 CAD2 amplified by primer pair CVF/CVR.

SEQ ID NO:25 shows a 48 amino acid predicted truncated protein sequence of 515Dbm1 CAD2.

SEQ ID NOs:26-35 show forward and reverse primers used to amplify partial CAD2 fragments from the DASbm1 mutant.

SEQ ID NOs:36 and 37 show a forward and a reverse primer used to amplify a partial CAD2 cDNA fragment.

SEQ ID NOs:38-40 show forward and reverse primers used to amplify partial CAD2 fragments from the DASbm1 mutant.

SEQ ID NO:41 shows a 3444 bp transposon insertion in DASbm1 CAD2.

SEQ ID NO:42 shows a duplicated 11 bp sequence in the DASbm1 transposon insertion from the first intron of CAD2: TACTGATATCT.

SEQ ID NOs:43-45 show primers used in a KASPar™ assay to differentiate the 515Dbm1 allele from other bm1 and the wild-type CAD2 alleles.

SEQ ID NOs:46 and 47 show template sequences to which primers anneal in a KASPar assay. SEQ ID NO:46 is a genomic sequence from 515Dbm1. SEQ ID NO:47 is a genomic sequence from 6XN442.

SEQ ID NO:48 shows a probe specific for mutant DASbm1.

SEQ ID NO:49 shows a probe specific for the wild-type CAD2 allele.

SEQ ID NOs:50-52 show primers used in a KASPar™ assay to differentiate the DASbm1 and wild-type CAD2 alleles.

SEQ ID NO:53 shows a probe specific for mutant 515Dbm1.

SEQ ID NO:54 shows a probe specific for the wild-type CAD2 allele.

SEQ ID NOs:55 and 56 show primers used in a KASPar™ assay to differentiate the 515Dbm1 and wild-type CAD2 alleles.

SEQ ID NOs:57-62 show primers and probes used for qRT-PCR of CAD2 and controls.

SEQ ID NO:63 shows a nucleotide sequence of the first exon of CAD2.

SEQ ID NO:64 shows a nucleotide sequence of the second exon of CAD2.

SEQ ID NO:65 shows a nucleotide sequence of the third exon of CAD2.

DETAILED DESCRIPTION

I. Overview of Several Embodiments

The bm1 mutant involves a previously undescribed mutation that co-localizes with the CAD locus. Halpin et al. (1998), supra; Guillaumie et al. (2007), supra. Described herein is the identification of specific mutations within the *Zea mays* CAD2 coding sequence that contribute to a bm1 phenotype. Some embodiments include a mutant cad2 gene cloned from a public bm1 corn line, 515Dbm1, that contains an AC insertion in the 3rd exon, which results in a truncated CAD2 protein. Some embodiments include a mutant cad2 gene cloned from a newly discovered bmr corn line, DASbm1, that contains a transposon insertion, which results in a distinct truncated CAD2 protein. DASbm1 plants have significantly lower cad2 RNA expression levels than wild-type plants, and also exhibit reduced lignin content. Development, validation, and application of high-throughput markers linked to each specific mutation are also described.

The molecular basis of the bm1 phenotype is not as well understood as, for example, bm3. Halpin et al. (1998), supra, showed that CAD activities, protein levels, and transcript abundance, were all significantly reduced in bm1 genotypes, and a CAD gene, later identified to be CAD2, was mapped closely linked to the bm1 locus. Because some CAD protein and mRNA could be detected in mutant plants, the authors proposed that bm1 was not a null mutation of CAD2, but instead affected its expression through regulatory elements.

Halpin et al. (1998), supra. Subsequent gene expression studies using microarrays showed that a large number of genes besides merely CAD2 were under-expressed in bm1 plants. Guillaumie et al. (2007), supra. This multitude of under-expressed genes included many lignin biosynthetic pathway genes and transcription factors, leading to further speculation that perhaps one of the transcription factors was the underlying gene for bm1.

More recently, nonsense mutations in the sorghum SbCAD2 gene have been shown to be the underlying mechanism for sorghum bmr mutant, bmr6, in some varieties. Saballos et al. (2009) Genetics 181:783-95; Sattler et al. (2009) Plant Physiology 150:584-95. The nonsense mutation contains a C to T substitution, which creates a premature STOP codon and results in a truncated SbCAD2 protein that lacks the NADPH-binding and C-terminal catalytic domains. Id.

In view of the foregoing, the accepted theory that the bm1 phenotype is attributable to a mutation in a transcription factor or gene regulatory element was challenged, and an investigation was conducted to determine whether a mutation in maize CAD2 could produce the bm1 phenotype. A close examination of the maize genetic/physical map in the region of the bm1 and CAD2 loci revealed that maize CAD2 is located very close to the centromere on chromosome 5. This proximity poses a significant challenge for high-resolution genetic mapping due to the known recombination suppression that surrounds centromere regions. Therefore, the success of traditional gene mapping approaches was at least unpredictable, if not entirely unlikely, and a PCR-based candidate gene cloning approach was designed to identify any specific mutations in ZmCAD2 that could be responsible for the bm1 phenotype in subject corn varieties.

Thus, in some embodiments, identification of specific cad2 mutants may be carried out using a PCR-based gene cloning approach. In some embodiments, *Zea mays* CAD2 may be cloned from both bm1 and wild-type germplasm to identify a specific mutation in cad2 from bm1 germplasm. In particular embodiments, an AC dinucleotide insertion mutation leading to a frame-shift is identified within bm1 germplasm. In further embodiments, a 3444 base pair transposon insertion in the first intron of CAD2 is identified within bm1 germplasm. A particular mutant cad2 gene leading to a bm1 phenotype in maize described herein comprises an AC dinucleotide insertion in the third exon of a cad2 gene cloned from bm1 variety, 515Dbm1.

A further mutant cad2 gene leading to a bm1 phenotype in maize described herein comprises a transposon insertion in the cad2 gene of a novel bm1 variety, DASbm1. The identified insertion is 3444 base pairs in length, and it is spliced into three exons (409 base pairs) that form a chimeric mRNA with CAD2. The chimeric mRNA causes a frame-shift and a premature STOP codon in the coding region that results in a truncated CAD2 protein of only 48 amino acids. This truncated protein lacks both the NADPH-binding and C-terminal catalytic domains, and is therefore most likely nonfunctional, even if it is produced in the cell.

DASbm1 plants, like 515Dbm1, have significantly reduced levels of cad2 RNA, and reduced total lignin contents. CAD2 was determined to be the underlying gene for the maize bm1 phenotype in these naturally-occurring mutants and provide a molecular basis for the observed bmr phenotype. Based on the transposon insertion in DASbm1 and the AC insertion in 515Dbm1, high-throughput KASPar and TaqMan assays for detecting these particular cad2 alleles and differentiating them from wild-type alleles have been determined and evaluated. The assays can be used for bm1 germplasm identification, for accelerating introgression of the bm1 trait, and for facilitating molecular breeding of plants having, e.g., improved silage digestibility and/or ethanol yield for biofuel. Mutated cad2 gene sequences can be used to introduce a bm1 phenotype into new maize genotypes or other crops, for example, sorghum and switch grass, using transgenic approaches. bm1 and other bmr phenotypes can also be used as visible selection markers for transgenes when combined with DAS' EXZACT Precision Technology.

High-throughput PCR markers that may be used, inter alia: to identify in an organism a cad2 mutation that contributes to a bm1 phenotype in corn; to introduce into an organism (e.g., a plant) a cad2 mutation that contributes to a bm1 phenotype in corn; and to facilitate marker-assisted breeding of bm1 corn. Thus, the development, validation and application of particular high-throughput PCR markers based on specific mutations in CAD2 (e.g., a frame-shift mutation, and a transposon insertion) are also described.

II. Abbreviations

4CL hydroxycinnamate coenzyme A ligases
ABC-transporter ATP-binding cassette transporter
AGO ARGONAUTE
APL ALTERED PHLOEM DEVELOPMENT
bmr/bm Brown midrib
bZIP basic region/leucine zipper motif
CAD cinnamyl alcohol dehydrogenase
CAD1 cinnamyl alcohol dehydrogenase 1
CAD2 cinnamyl alcohol dehydrogenase 2
CCR cinnamoyl-CoA reductase
COMT caffeic acid 3-O-methyltransferase
COV1 CONTINUOUS VASCULAR RING
DFR dihydro-flavonoid reductase
EgCAD1-type ZmCAD1 EgCAD1-type maize cinnamyl alcohol dehydrogenase 1
EST expressed sequence tag
F5H cytochrome P450-dependent ferulate 5-hydroxylases
FAM fluorophore 6-carboxyfluorescein
HCT hydroxycinnamoyl-CoA transferase 2
KLIMS KBioscience Laboratory Information Management System
LIM LIM homeodomain
MADS-box conserved MADS sequence motif (MCM1, AGAMOUS, DEFICIENS, SRF)
MP MONOPTEROUS
OMT O-methyl transferase
ORF open reading frame
PAL phenylalanine ammonia lyase
PCR polymerase chain reaction
RFU relative fluorescence units
SAD sinapyl alcohol dehydrogenase
SAMS3 S-adenosyl-methionine synthase 3
VIC® VIC® fluorophore (Applied Biosystems)

III. Terms

Backcrossing: Backcrossing methods may be used to introduce a nucleic acid sequence into plants. The backcrossing technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

Corn plant: As used herein, the term "corn plant" refers to a plant of the species, *Zea mays* (maize).

bmr/bm corn: As used herein, the term "bm corn" (or "bmr corn") refers to corn varieties that contain a brown midrib mutation. BM corn varieties typically exhibit a reddish brown pigmentation of the leaf midrib. BM corn is also typically characterized by lower lignin content, higher fiber digestibility, and higher dry matter intake. Non-limiting examples of BM corn varieties include bm1 corn varieties; e.g., 515Dbm1.

bm1 phenotype: As used herein, the term "bm1 phenotype" may refer to a profile of altered lignin content and/or composition that has been observed in bm1 corn. For example and without limitation, a bm1 phenotype may be characterized by one or more of the following characteristics: lignin content that is reduced by 10-20% when compared to the lignin content of a wild-type plant of the same species (Guillaumie et al. (2007), supra); a decrease in ferulic acid esters (Id.); reduced content of ferulic acid ethers (Id.); reduced content of p-coumaric esters (Marita et al. (2003) J. Agric. Food Chem. 51:1313-21); increased aldehyde levels (Id.); enrichment of lignins in carbon-carbon inter unit subunit linkages (Halpin et al. (1998), supra; Barriére et al. (2004), supra); and substantial incorporation of coniferaldehyde and/or sinapaldehyde into lignins (Kim et al. (2002), supra; and Barriére et al. (2004), supra).

Dry matter: As used herein, the term "dry matter" refers to any feedstuff, including forage.

KBiosciences Competitive Allele-Specific PCR SNP genotyping system (KASPar™): KASPar™ is a commercially available homogeneous fluorescent system for determining SNP genotypes (KBiosciences Ltd., Hoddesdon, UK). A KASPar™ assay comprises an SNP-specific "assay mix," which contains three unlabelled primers, and a "reaction mix," which contains all the other required components; for example, a universal fluorescent reporting system. In addition to these mixes, the user provides, inter alia, a FRET-capable plate reader, microtitre plate(s), and DNA samples that contain about 5 ng/μL DNA.

A typical KASPar™ assay comprises the steps of: allele-specific primer design (e.g., using PrimerPicker™, which is a free service available through the interne at the KBiosciences website); preparation of reaction mix including the allele-specific primers; admixing the reaction mix to DNA samples in a microtitre plate; thermocycling; reading the plate in a fluorescent plate reader; and plotting and scoring the fluorescent data. Data from each sample are plotted together on a 2-D graph, where the x- and y-axes correspond to FAM and VIC fluorescence values. Samples having the same SNP genotype cluster together on the plot (i.e., A/A; A/a; and a/a). More technical information about the KASPar system, including a guide of solutions to common problems, is obtainable from KBiosciences Ltd. (e.g., the *KASPar SNP Genotyping System Reagent Manual*).

Linked, tightly linked, and extremely tightly linked: As used herein, linkage between genes or markers may refer to the phenomenon in which genes or markers on a chromosome show a measurable probability of being passed on together to individuals in the next generation. The closer two genes or markers are to each other, the closer to (1) this probability becomes. Thus, the term "linked" may refer to one or more genes or markers that are passed together with a gene with a probability greater than 0.5 (which is expected from independent assortment where markers/genes are located on different chromosomes). When the presence of a gene contributes to a phenotype in an individual, markers that are linked to the gene may be said to be linked to the phenotype. Thus, the term "linked" may refer to a relationship between a marker and a gene, or between a marker and a phenotype.

Because the proximity of two genes or markers on a chromosome is directly related to the probability that the genes or markers will be passed together to individuals in the next generation, the term "linked" may also refer herein to one or more genes or markers that are located within about 2.0 Mb of one another on the same maize chromosome. Thus, two "linked" genes or markers may be separated by about 2.1 Mb; 2.00 Mb; about 1.95 Mb; about 1.90 Mb; about 1.85 Mb; about 1.80 Mb; about 1.75 Mb; about 1.70 Mb; about 1.65 Mb; about 1.60 Mb; about 1.55 Mb; about 1.50 Mb; about 1.45 Mb; about 1.40 Mb; about 1.35 Mb; about 1.30 Mb; about 1.25 Mb; about 1.20 Mb; about 1.15 Mb; about 1.10 Mb; about 1.05 Mb; about 1.00 Mb; about 0.95 Mb; about 0.90 Mb; about 0.85 Mb; about 0.80 Mb; about 0.75 Mb; about 0.70 Mb; about 0.65 Mb; about 0.60 Mb; about 0.55 Mb; about 0.50 Mb; about 0.45 Mb; about 0.40 Mb; about 0.35 Mb; about 0.30 Mb; about 0.25 Mb; about 0.20 Mb; about 0.15 Mb; about 0.10 Mb; about 0.05 Mb; about 0.025 Mb; and about 0.01 Mb. Particular examples of markers that may be "linked" to a bm1 phenotype in maize include nucleotide sequences on chromosome 5 of the maize genome.

As used herein, the term "tightly linked" may refer to one or more genes or markers that are located within about 0.5 Mb of one another on the same maize chromosome. Thus, two "tightly linked" genes or markers may be separated by about 0.6 Mb; about 0.55 Mb; 0.5 Mb; about 0.45 Mb; about 0.4 Mb; about 0.35 Mb; about 0.3 Mb; about 0.25 Mb; about 0.2 Mb; about 0.15 Mb; about 0.1 Mb; and about 0.05 Mb. Particular examples of markers that may be "tightly linked" to a bm1 phenotype in maize include nucleotide sequences near or within the CAD2 locus of the maize genome.

As used herein, the term "extremely tightly linked" may refer to one or more genes or markers that are located within about 100 kb of one another on the same maize chromosome. Thus, two "extremely tightly linked" genes or markers may be separated by about 125 kb; about 120 kb; about 115 kb; about 110 kb; about 105 kb; 100 kb; about 95 kb; about 90 kb; about 85 kb; about 80 kb; about 75 kb; about 70 kb; about 65 kb; about 60 kb; about 55 kb; about 50 kb; about 45 kb; about 40 kb; about 35 kb; about 30 kb; about 25 kb; about 20 kb; about 15 kb; about 10 kb; about 5 kb; and about 1 kb. Particular examples of markers that are "extremely tightly linked" to a bm1 phenotype in maize include nucleotide sequences within introns and exons of the CAD2 gene.

In view of the foregoing, it will be appreciated that markers linked to a particular gene or phenotype include those markers that are tightly linked, and those markers that are extremely tightly linked, to the gene or phenotype. Linked, tightly linked, and extremely tightly genetic markers of a bm1 phenotype may be useful in marker-assisted breeding programs to identify maize varieties having a reduced lignin content and improved digestibility, and to breed these traits into other maize varieties.

Locus: As used herein, the term "locus" refers to a position on the genome that corresponds to a measurable characteristic (e.g., a trait). An SNP locus is defined by a probe that hybridizes to DNA contained within the locus.

Marker: As used herein, a marker refers to a gene or nucleotide sequence that can be used to identify plants having a particular allele. A marker may be described as a variation at a given genomic locus. A genetic marker may be a short DNA sequence, such as a sequence surrounding a single base-pair change (single nucleotide polymorphism, or "SNP"), or a long one, for example, a minisatellite/simple sequence repeat ("SSR"). A "marker allele" refers to the version of the marker that is present in a particular individual.

The term marker as used herein may refer to a cloned segment of maize chromosomal DNA (for example, nucleotide sequences near or within the CAD2 locus of the maize genome), and may also or alternatively refer to a DNA molecule that is complementary to a cloned segment of maize chromosomal DNA (for example, DNA complementary to a nucleotide sequence near or within the CAD2 locus of the maize genome). Particular examples of bm1 markers in maize include without limitation nucleic acid sequences including nucleotide 66 of the CAD2 gene; nucleic acid sequences including nucleotide 284 of the CAD2 gene; nucleic acid sequences including nucleotide 415 of the CAD2 gene; nucleic acid sequences including nucleotide 443 of the CAD2 gene; nucleic acid sequences including nucleotide 735 of the CAD2 gene; nucleic acid sequences including nucleotide 760 of the CAD2 gene; nucleic acid sequences including nucleotide 1345 of the CAD2 gene; nucleic acid sequences including nucleotide 1408 of the CAD2 gene; nucleic acid sequences including nucleotide 1585 of the CAD2 gene; nucleic acid sequences including any of nucleotides 1627-1640 and/or 1642-1648 of the CAD2 gene; nucleic acid sequences including nucleotide 2252 of the CAD2 gene; nucleic acid sequences including nucleotide 2269 of the CAD2 gene; nucleic acid sequences including nucleotide 2786 of the CAD2 gene; nucleic acid sequences including nucleotide 2966 of the CAD2 gene; nucleic acid sequences including nucleotide 3205 of the CAD2 gene; nucleic acid sequences including nucleotide 3719 of the CAD2 gene; nucleic acid sequences including nucleotide 3783 of the CAD2 gene; nucleic acid sequences including nucleotide 3798 of the CAD2 gene; nucleic acid sequences including nucleotide 3800 of the CAD2 gene; nucleic acid sequences including nucleotide 3994 of the CAD2 gene; nucleic acid sequences including nucleotide 4141 of the CAD2 gene; nucleic acid sequences including nucleotide 4338 of the CAD2 gene; nucleic acid sequences including nucleotide 4583 of the CAD2 gene; and nucleic acid sequences including nucleotide 5403 of the CAD2 gene. The foregoing markers are identified by nucleotide position in wild-type maize variety, B73.

In some embodiments, the presence of a marker in a plant may be detected through the use of a nucleic acid probe. A probe may be a DNA molecule, or an RNA molecule. RNA probes can be synthesized by means known in the art, for example, using a DNA molecule template. A probe may contain all or a portion of the nucleotide sequence of the marker and additional, contiguous nucleotide sequence from the plant genome. This is referred to herein as a "contiguous probe." The additional, contiguous nucleotide sequence is referred to as "upstream" or "downstream" of the original marker, depending on whether the contiguous nucleotide sequence from the plant chromosome is on the 5' or the 3' side of the original marker, as conventionally understood. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome. All above-described markers may be used in some embodiments of the present invention.

An oligonucleotide probe sequence may be prepared synthetically or by cloning. Suitable cloning vectors are well-known to those of skill in the art. An oligonucleotide probe may be labeled or unlabeled. A wide variety of techniques exist for labeling nucleic acid molecules, including, for example and without limitation: radiolabeling by nick translation; random priming; tailing with terminal deoxytransferase; or the like, where the nucleotides employed are labeled, for example, with radioactive $^{32}P$. Other labels which may be used include, for example and without limitation: fluorophores (e.g., FAM and VIC); enzymes; enzyme substrates; enzyme cofactors; enzyme inhibitors; and the like. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may contain a nucleotide sequence that is not contiguous to that of the original marker; this probe is referred to herein as a "non-contiguous probe." The sequence of the non-contiguous probe is located sufficiently close to the sequence of the original marker on the genome so that the non-contiguous probe is genetically linked to the same gene or trait (e.g., bm1/reduced lignin content). For example, in some embodiments, a non-contiguous probe is located within 500 kb; 450 kb; 400 kb; 350 kb; 300 kb; 250 kb; 200 kb; 150 kb; 125 kb; 100 kb; 0.9 kb; 0.8 kb; 0.7 kb; 0.6 kb; 0.5 kb; 0.4 kb; 0.3 kb; 0.2 kb; or 0.1 kb of the original marker on the maize genome.

A probe may be an exact copy of a marker to be detected. A probe may also be a nucleic acid molecule comprising, or consisting of, a nucleotide sequence which is substantially identical to a cloned segment of the subject organism's (for example, maize) chromosomal DNA. As used herein, the term "substantially identical" may refer to nucleotide sequences that are more than 85% identical. For example, a substantially identical nucleotide sequence may be 85.5%; 86%; 87%; 88%; 89%; 90%; 91%; 92%; 93%; 94%; 95%; 96%; 97%; 98%; 99% or 99.5% identical to the reference sequence.

A probe may also be a nucleic acid molecule that is "specifically hybridizable" or "specifically complementary" to an exact copy of the marker to be detected ("DNA target"). "Specifically hybridizable" and "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, 2$^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985.

Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 60° C. in TaqMan® genotyping master mix (Applied Biosystems, Foster City, Calif., Catalog #4371355), diluted according to the manufacturer's instructions.

The following are representative, non-limiting hybridization conditions.

Very High Stringency (detects sequences that share at least 90% sequence identity): Hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency (detects sequences that share at least 50% sequence identity): Hybridization in 6×SSC buffer at room temperature to 55° C. for 16-20 hours; wash at least twice in 2×-3×SSC buffer at room temperature to 55° C. for 20-30 minutes each.

With respect to all probes discussed, supra, the probe may comprise additional nucleic acid sequences, for example, promoters; transcription signals; and/or vector sequences. Any of the probes discussed, supra, may be used to define additionally markers that are tightly-linked to a gene involved in a bmr phenotype (e.g., bm1), and markers thus identified may be equivalent to exemplary markers named in the present disclosure, and thus are within the scope of the invention.

Marker-assisted breeding: As used herein, the term "marker-assisted breeding" may refer to an approach to breeding directly for one or more complex traits (e.g., bm1/reduced lignin content). In current practice, plant breeders attempt to identify easily detectable traits, such as flower color, seed coat appearance, or isozyme variants that are linked to an agronomically desired trait. The plant breeders then follow the agronomic trait in the segregating, breeding populations by following the segregation of the easily detectable trait. However, there are very few of these linkage relationships available for use in plant breeding.

Marker-assisted breeding provides a time- and cost-efficient process for improvement of plant varieties. Several examples of the application of marker-assisted breeding involve the use of isozyme markers. See, e.g., Tanksley and Orton, eds. (1983) *Isozymes in Plant Breeding and Genetics*, Amsterdam: Elsevier. One example is an isozyme marker associated with a gene for resistance to a nematode pest in tomato. The resistance, controlled by a gene designated Mi, is located on chromosome 6 of tomato and is very tightly linked to Aps1, an acid phosphatase isozyme. Use of the Aps1 isozyme marker to indirectly select for the Mi gene provided the advantages that segregation in a population can be determined unequivocally with standard electrophoretic techniques; the isozyme marker can be scored in seedling tissue, obviating the need to maintain plants to maturity; and co-dominance of the isozyme marker alleles allows discrimination between homozygotes and heterozygotes. See Rick (1983) in Tanksley and Orton, supra.

Meat: As used herein, the term "meat" refers to animal tissue used, for example, as food. The term "meat" typically refers to skeletal muscle and associated fat, but may also refer to non-muscle organs, including lungs, livers, skin, brains, bone marrow, kidneys, testicles, intestines, etc.

Neutral detergent fiber: As used herein the term "neutral detergent fiber" (NDF) refers to a measure of slowly digested material across a wide range of feeds. NDF levels in forage increase as the plant matures. Average levels of NDF in grass silage may be approximately 55 percent DM (550 g/kg DM). The content of NDF in a total ration may be between 35-50% DM. Diets with less than 32 percent NDF may cause problems with acidosis. Diets that contain over 50 percent NDF may be restricted in their intake potential.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A nucleic acid molecule can include either or both naturally occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Sequence identity: The term "sequence identity" or "identity," as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Single-nucleotide polymorphism: As used herein, the term "single-nucleotide polymorphism" (SNP) may refer to a DNA sequence variation occurring when a single nucleotide in the genome (or other shared sequence) differs between members of a species or paired chromosomes in an individual. Within a population, SNPs can be assigned a minor allele frequency that is the lowest allele frequency at a locus that is observed in a particular population. This is simply the lesser of the two allele frequencies for single-nucleotide polymorphisms. Different populations are expected to exhibit at least slightly different allele frequencies. Particular populations may exhibit significantly different allele frequencies. In some examples, markers linked to a bm1 phenotype are SNP markers.

SNPs may fall within coding sequences of genes, non-coding regions of genes, or in the intergenic regions between genes. SNPs within a coding sequence may, but will not necessarily, change the amino acid sequence of the protein that is produced, due to degeneracy of the genetic code. An SNP in which both forms lead to the same polypeptide sequence is termed "synonymous" (sometimes called a silent mutation). If a different polypeptide sequence is produced, they are termed "non-synonymous." A non-synonymous change may either be missense or nonsense, where a missense change results in a different amino acid, and a nonsense change results in a premature stop codon. SNPs that are not in protein-coding regions may still have consequences for gene splicing, transcription factor binding, or the sequence of non-coding RNA. SNPs are usually biallelic and thus easily assayed in plants and animals. Sachidanandam (2001) Nature 409:928-33.

Silage: As used herein, the term "silage" refers to a certain type of storage forage. Generally, silage is made from plants (e.g., corn plants) in a process called ensilage. During this process, plants or plant parts undergo anaerobic fermentation caused by indigenous microorganisms (e.g., one or more strains of lactic acid bacteria, for example, *Lactobacillus* spec.) converting sugars to acids and exhausting any oxygen present in the crop material, which depletion of oxygen preserves the forage in conjunction with bacteria-generated volatile fatty acids, such as acetate, propionate, lactate, and butyrate. Silage is widely used for feeding milk- and meat-producing animals, such as dairy cattle and beef cattle.

The term "producing silage" describes the process of how to obtain silage suitable for feeding to a meat-producing animal. Generally, silage is produced from plants, for example, corn plants, by chopping the harvested plant biomass with a forage harvester.

Fiber source: As used herein, the term "fiber source" refers to a material obtained from a plant or microbial source, which material contains edible fibers. Practical, but not limiting examples of fiber sources include, the hulls of agricultural seed products such as from soy beans, or from grains such as rice, wheat, corn, barley; the stalks from such grains (straw); vegetable/plant-based soap stocks, corn stover, which typically includes the stalks, husks and leaves from a harvested corn plant; processed component fractions of agricultural products that are enriched in fiber, for example corn gluten feed; leaf material from any plant source, and distillers dried grains with or without solubles dried thereon. Thus, in particular examples, a fiber source may include, for example, mixtures of the following: alfalfa, barley products (e.g., straw), beet pulp, soy hulls, switch grass, corn fiber, soy fiber, cocoa hulls, corn cobs, corn husks, corn stove, wheat straw, wheat chaff, rice straw, flax hulls, soy meal, corn meal, wheat germ, corn germ, shrubs, and grasses. For the purpose of clarity in the present disclosure, distillers dried grains (with or without solubles) and distillers grains (with or without solubles) contain fiber, but are not considered "fiber sources." Distillers dried grains (with or without solubles) and distillers grains (with or without solubles) are considered "corn co-products," as set forth below.

Corn co-product: As used herein the term "corn co-product" refers to products that remain following the wet milling or dry milling of corn. Non-limiting examples of corn co-products include corn gluten, distillers grains, distillers grains plus solubles, distiller dried grains, distillers dried grains with solubles, condensed distillers solubles, bran cake, modified distillers grains, modified distillers grain plus solubles.

Supplement: As used herein, the term "supplement" refers to any ingredient included in a feed mix to enhance the nutritional value of the feed mix. Commonly used supplements include protein (e.g., soybean meal or urea), minerals (e.g., bone meal), energy (e.g., animal fat), and vitamins.

Trait or phenotype: The terms "trait" and "phenotype" are used interchangeably herein. For the purposes of the present disclosure, a trait of particular interest is bm1/reduced lignin content.

IV. Gene and Gene Variations Associated with bm1 Phenotype, and Uses Thereof

This disclosure provides novel mutant cad2 genes that contribute to a bm1 phenotype in maize. Plants (e.g., maize) that comprise a mutant cad2 gene described herein may have cell walls with lignin levels that are lower than those found in wild-type plants of the same variety. In some embodiments, a nucleic acid molecule comprising a mutant cad2 gene according to the disclosure may be introduced into an organism, for example, to assist in the development of reduced lignin phenotypes. In particular embodiments, the organism may be a plant (e.g., maize). However, a nucleic acid molecule comprising a mutant cad2 gene according to the disclosure may be introduced into an organism that is not a plant, for example, yeast, or prokaryotes. In some embodiments, a mutant cad2 gene according to the disclosure may be used to identify plants comprising a mutant cad2 gene, or plants likely to have a bm1 or other reduced lignin phenotype. For example, the sequence of a mutant cad2 gene according to the disclosure may be used to design probes that detect the presence of a mutant cad2 gene in a plant, or in a sample prepared from a plant. In particular examples, a nucleic acid probe that hybridizes to the nucleotide sequence of a mutant cad2 gene, but not a particular wild-type CAD2 gene, is provided.

In some embodiments, the invention also includes those nucleic acid molecules that comprise a sequence that is substantially identical to a mutant cad2 gene according to the disclosure, which sequence may or may not comprise an AC dinucleotide insertion and/or a transposon insertion as described herein. For example, in some embodiments, a nucleic acid molecule may comprise a sequence that is at least about 85% identical to a mutant cad2 gene according to the disclosure. Thus, a nucleic acid molecule may comprise a sequence that is substantially identical to a mutant cad2 gene according to the disclosure that is 86%; 87%; 88%; 89%; 90%; 91%; 92%; 93%; 94%; 95%; 96%; 97%; 98%; 99% or 99.5% identical to a mutant cad2 gene according to the disclosure. Such nucleic acid molecules that are substantially identical to a mutant cad2 gene according to the disclosure may be readily identified and isolated, for example, from any complete or partial genomes readily available to those of skill in the art for a variety of organisms.

Some embodiments also include functional variants of a mutant cad2 gene according to the disclosure. Functional variants of a mutant cad2 gene according to the disclosure may include, for example, a mutant cad2 gene according to the disclosure comprising one or more nucleotide substitutions, deletions, or insertions, wherein the functional variant contributes to a bm1 or other reduced lignin phenotype, as may be measured by routine techniques well-known to those of ordinary skill in the art. For example, a functional variant of a mutant cad2 gene according to the disclosure may comprise an AC dinucleotide insertion and/or a transposon insertion as described herein. The capability of a particular variant of a mutant cad2 gene according to the disclosure to reduce lignin content or contribute to a bm1 phenotype may be determined by routine introduction of the mutation or fragment into a plant, followed by routine observation of the plant for reduced lignin content or other characteristics of a bm1 phenotype. Functional variants of a mutant cad2 gene according to the disclosure may be created by site-directed mutagenesis, induced mutation, or they may occur as allelic variants (polymorphisms, e.g., SNPs).

In some embodiments, therefore, functional variants of a mutant cad2 gene according to the disclosure may comprise additional mutations of a CAD2 gene, fragments smaller than the sequence of a mutant cad2 gene according to the disclosure, and/or chimeric proteins that comprise a mutant cad2 gene according to the disclosure, which functional variants retain the properties of the mutant cad2 gene. Such mutations and fragments are therefore considered to be within the scope of the invention. One of ordinary skill in the art can readily determine whether an additional mutation or fragment of a mutant cad2 gene according to the disclosure retains the properties of the mutant cad2 gene.

In some embodiments, the ability to introduce into a plant, and detect in the plant, a mutant cad2 gene of the disclosure may facilitate marker-assisted breeding and selection of plants having a mutant cad2 gene, which plants may also be likely to have a bm1 or other reduced lignin phenotype. In particular examples, a mutant cad2 gene according to the disclosure may be introduced into a plant (e.g., by genetic transformation, or traditional breeding techniques such as crossing), and a plant comprising the mutant cad2 gene may then be selected by using a probe that detects the presence of the mutant cad2 gene in the plant. Plants into which a mutant cad2 gene of the disclosure have been introduced may be crossed with plants that may or may not also comprise a mutant cad2 gene, and progeny may be then be selected by using a probe that detects the presence of the mutant cad2 gene of the disclosure in the plant. Further crosses may be made to obtain a plant of a desired genotype.

When a nucleic acid sequence (e.g., a mutant cad2 gene according to the disclosure) is "introduced" into an organism, such as a plant, the technique or methodology used for the introduction of a nucleic acid molecule comprising the particular sequence is not essential to the invention, and may occur by any technique or methodology known to those of skill in the art. For example, a nucleic acid molecule may be introduced by direct transformation methods, such as *Agrobacterium*-mediated transformation of plant tissue; microprojectile bombardment; electroporation; etc. Alternatively, a nucleic acid molecule may be introduced by crossing a plant having the particular nucleotide sequence with another plant, such that progeny have the nucleotide sequence incorporated into their genome. Such breeding techniques are well-known to one skilled in the art. Marker-assisted breeding techniques, as disclosed herein, may greatly facilitate the incorporation of a mutant cad2 gene according to the disclosure through such crosses.

In embodiments wherein a mutant cad2 gene according to the disclosure is introduced to an organism, it may be desirable for the mutant cad2 gene to be introduced in such a manner that the mutant cad2 gene is operably linked to one or more regulatory sequences, for example, introduction via the use of a plasmid comprising the mutant cad2 gene according to the disclosure operably linked to the desired regulatory sequences. Regulatory sequences useful in the expression of heterologous nucleic acid sequences are well-known in the art, and include, for example and without limitation: Promoters (e.g., constitutive promoters; tissue-specific promoters; and developmental stage-specific promoters); termination sequences; enhancer sequences; subcellular targeting sequences; stabilizing or leader sequences; and introns.

A mutant cad2 gene according to the disclosure may be introduced into an organism with one or more marker genes operably linked to a regulatory element (a promoter, for example) that allows transformed cells containing the marker to be either recovered by negative selection (i.e., inhibiting growth of cells that do not contain the selectable marker gene) or by positive selection (i.e., screening for the product encoded by the genetic marker). Many selectable marker genes for transformation are well known in the transformation arts and include, for example, genes that code for enzymes that metabolically detoxify a selective chemical agent which may be an antibiotic or an herbicide, or genes that encode an altered target which may be insensitive to the inhibitor. A few positive selection methods are also known in the art. Examples of marker genes suitable for use in plant cells may include, for example, and without limitation: The neomycin phosphotransferase II (nptII) gene (Fraley et al. (1983) Proc. Natl. Acad. Sci. USA 80:4803); the hygromycin phosphotransferase gene (Vanden Elzen et al. (1985) Plant Mol. Biol. 5:299); gentamycin acetyl transferase, streptomycin phosphotransferase, aminoglycoside-3'-adenyl transferase, and the bleomycin resistance determinant (See, e.g., Hayford et al. (1988) Plant Physiol. 86:1216; Jones et al. (1987) Mol. Gen. Genet. 210:86); Svab et al. (1990) Plant Mol. Biol. 14:197; and Hille et al. (1986) Plant Mol. Biol. 7:171); selectable marker genes that confer resistance to herbicides, such as glyphosate, glufosinate or bromoxynil (See, e.g., Comai et al. (1985) Nature 317:741-744; Gordon-Kamm et al. (1990) Plant Cell 2:603-618; and Stalker et al. (1988) Science 242:419-423); mouse dihydrofolate reductase (Eichholtz et al. (1987) Somatic Cell Mol. Genet. 13:67); plant 5-enolpyruvylshikimate-3-phosphate synthase (Shah et al. (1986) Science 233:478); plant acetolactate synthase (Charest et al. (1990) Plant Cell Rep. 8:643).

Another class of marker genes suitable for plant transformation employs screening of presumptively transformed plant cells rather than direct genetic selection of transformed cells for resistance to a toxic substance, such as an antibiotic. These genes are particularly useful to quantify or visualize the spatial pattern of expression of a gene in specific tissues, and are frequently referred to as "reporter genes," because they can be fused to a gene or gene regulatory sequence for the investigation of gene expression. Commonly used genes for screening transformed cells include β-glucuronidase (GUS), β-galactosidase, luciferase and chloramphenicol acetyltransferase. See, e.g., Jefferson (1987) Plant Mol. Biol. Rep. 5:387; Teeri et al. (1989) EMBO J. 8:343; Koncz et al. (1987) Proc. Natl. Acad. Sci. U.S.A. 84:131; and DeBlock et al. (1984) EMBO J. 3:1681.

Recently, in vivo methods for visualizing GUS activity that do not require destruction of plant tissue have been made available. Molecular Probes publication 2908, Imagene Green™, p. 1-4, 1993; and Naleway et al. (1991) J. Cell Biol. 115:151a. Further, genes encoding Fluorescent Proteins (e.g., GFP, EGFP, EBFP, ECFP, and YFP) have been utilized as markers for gene expression in prokaryotic and eukaryotic cells. See Chalfie et al. (1994) Science 263:802. Fluorescent proteins and mutations of fluorescent proteins may be used as screenable markers.

In some embodiments, a mutant cad2 gene according to the disclosure and/or fragments or segments of a mutant cad2 gene according to the disclosure may be used to identify homologous mutant cad2 gene sequences from organisms other than maize (e.g., by sequence comparison). Sequences from organisms other than maize that are homologous to a mutant cad2 gene according to the disclosure may be identified and isolated according to well-known techniques, for example, based on their sequence homology to a mutant cad2 gene according to the disclosure.

Thus, in some embodiments, all or part of a coding sequence from a mutant cad2 gene according to the disclosure may be used as a probe which specifically hybridizes to other sequences present in a population of cloned genomic DNA fragments (i.e., a genomic library) from an organism according to routine techniques. Thus, in some embodiments, the invention includes those nucleotide sequences which specifically hybridize to a mutant cad2 gene according to the disclosure.

In further embodiments, sequences from organisms other than maize that are homologous to a mutant cad2 gene according to the disclosure may be identified and isolated by sequence comparison. For example, the complete or partial sequenced genome of an organism may be searched according to routine techniques with the sequence of a mutant cad2 gene according to the disclosure to identify genes within the genome of the organism that share a high degree of sequence identity with the mutant cad2 gene, and are therefore likely homologues of the mutant cad2 gene.

For example, all or part of a mutant cad2 gene according to the disclosure may be used as a "reference sequence." Generally, nucleic acid sequences (e.g., cloned or genomic DNA fragments of a genomic library) that are compared to the reference sequence comprise a "comparison window," which is a specific contiguous segment of the nucleic acid sequence. The comparison window may comprise additions or deletions (i.e., gaps) compared to the reference sequence (which does not comprise additions or deletions) for optimal alignment of the two sequences. The comparison window is typically at least 20 contiguous nucleotides in length, but may be 30, 40, 50, 100, or 200 nucleotides in length, or longer. To avoid a high similarity to the reference sequence due to inclusion of deletions in the polynucleotide sequence comparison window, a "gap penalty" may be introduced to be subtracted from the number of nucleotide matches.

Methods of aligning sequences for comparison are well-known in the art. The determination of percent sequence identity between any two sequences can be accomplished using available mathematical algorithms. Non-limiting examples of such mathematical algorithms are the algorithm of Myers and Miller (1988), CABIOS 4:11-7; the local alignment algorithm of Smith et al. (1981) Adv. Appl. Math. 2:482; the global alignment algorithm of Needleman and Wunsch (1970), J. Mol. Biol. 48:443-53; the search-for-local-alignment method of Pearson and Lipman (1988), Proc. Natl. Acad. Sci. USA 85:2444-8; the algorithm of Karlin and Altschul (1990), Proc. Natl. Acad. Sci. USA 87:2264, and Karlin and Altschul (1993) Proc. Natl. Acad. Sci. USA 90:5873-7.

One of ordinary skill in the art can implement these mathematical algorithms on a computer for comparison of sequences to determine sequence identity, or to search a database comprising a plurality of sequences (e.g., an organism genome database) according to shared sequence identity with a reference sequence. Such implementations include, but are not limited to, CLUSTAL in the PC/Gene program (Intelligenetics, Mountain View, Calif.); and the ALIGN program and GAP, BESTFIT, BLAST, FASTA, and TFASTA in the GCG Wisconsin Genetics Software Package, v. 10 (Accelrys Inc., San Diego, Calif.). Sequence alignments using these programs may be performed using their default parameters. Alternatively, it may be desirable to modify the default parameters in some searches (e.g., altering the value of a gap penalty). The selection of a particular computer implementation of mathematical algorithms for calculation of sequence identity and the selection of parameter values for use in a selected algorithm are within the discretion of one of skill in the art.

In some embodiments, a mutant cad2 gene according to the disclosure may be introduced into a plant comprising an additional desired gene (e.g., a mutant gene or minor allele) or phenotype by crossing. Alternatively, a mutant cad2 gene according to the disclosure may be introduced into a plant comprising an additional desired gene or phenotype, for example, by genetic transformation. In certain embodiments, a mutant cad2 gene according to the disclosure may be introduced into a plant comprising a mutation in one or more additional genes involved in lignin biosynthesis or metabolism. For example and without limitation, a mutant cad2 gene according to the disclosure may be introduced into a plant comprising a mutation in, e.g., a different CAD gene; COMT;

4CL; FSH; EgCAD1-type ZmCAD1; SAD; a chorismate mutase gene; PAL; HCT; OMT; a cytochrome P450 gene; SAMS3; CCR; DFR; a chalcone synthase gene; a laccase gene; a peroxidase gene; a ALDH gene (for example, one of six maize ALDH genes described in Skibbe et al. (2002) Plant Mol. Biol. 48:751-64); AGO; an MYB transcription factor gene (e.g., ZmMYB38; and maize APL); a LIM transcription factor gene; a maize bZIP factor gene; an MADS-box gene (e.g., ZmZAG5); an MP gene; an ABC transporter gene; a β-glucosidase gene; a glutathione S-transferase gene (e.g., ZmGST17); a nodulin MtN21-like gene; a PINOID orthologous gene; a histidine kinase (e.g., ZmHK1, ZmHK2, and ZmHK3); and/or a COV1 orthologous gene. In some embodiments, a mutant cad2 gene according to the disclosure may be introduced into a plant comprising one or more desirable trait(s) that are not involved in lignin biosynthesis or metabolism, in order to produce a plant with both a bm1 or other reduced lignin phenotype and the one or more desirable trait(s) that are not involved in lignin biosynthesis or metabolism.

It is expected that plants of these and other embodiments that contain multiple mutant genes in the lignin biosynthetic or metabolic pathways will exhibit useful novel phenotypes, for example, additional bmr phenotypes, and/or other lignin phenotypes. See, e.g., Marita et al. (2003), supra. For example, stacking the bm1 trait with the bm3 trait was observed to result in further increases in silage digestibility, and a very significant improvement in the yield of fermentable sugars in biomass hydrolysis without pre-treatment.

Some embodiments utilize means for producing a genetically modified plant comprising a mutant maize cad2 gene, and/or means for identifying plants carrying a mutant maize cad2 gene. In some examples, a means for producing a genetically modified plant comprising a mutant maize cad2 gene may be a marker that is located within a mutant maize cad2 gene according to the disclosure. In some examples, a means for identifying plants carrying a mutant maize cad2 gene may be a probe that specifically hybridizes to a marker that is located within a mutant maize cad2 gene according to the disclosure. Mutant cad2 genes according to the disclosure (with respect to a means for producing a genetically modified plant comprising a mutant maize cad2 gene, and a means for identifying plants carrying a mutant maize cad2 gene) are those mutant cad2 genes that contribute to a bm1 phenotype in either maize inbred line, 515Dbm1, or line, DASbm1. These mutant cad2 genes are characterized by either a frame shift mutation in the third exon of a CAD2 gene that results in a truncated CAD2 protein, or a 3444 base pair transposon insertion in the first intron of a CAD2 gene that results in a truncated CAD2 protein. Thus, in some embodiments, a mutant cad2 gene may comprise the first exon of the genomic ZmCAD2 gene sequence and/or the second exon of the genomic ZmCAD2 gene sequence, but may not comprise all or part of the third exon of the genomic ZmCAD2 gene sequence.

The mutant cad2 genes disclosed herein are different from previously described cad2 mutations that may be involved in bmr phenotypes. For example, a mutant cad2 gene according to the disclosure may have one or more of the following characteristics: a dinucleotide insertion in an exon of a ZmCAD2 gene (e.g., exon 3); a mutation resulting in a frame shift; a transposon insertion in an intron or exon of a ZmCAD2 gene that results in a truncated protein; a mutation resulting in a truncated ZmCAD2 enzyme; a mutation resulting in the inactivation (e.g., by removal) of the ZmCAD2 NADPH-binding and/or C-terminal catalytic domain(s); a mutation that contributes to a bm1 phenotype in inbred maize line 515Dbm1; and a mutation that contributes to a bm1 phenotype in inbred maize line DASbm1. In contrast, previously described naturally-occurring mutant cad2 genes are characterized by the insertion of a transposon in the last exon of the gene (exon 4) (U.S. Patent Application US 2010/0203196 A1); reduced expression of a full-length CAD protein (Halpin et al. (1998), supra); a point mutation leading to truncation of the *Sorghum bicolor* CAD2 enzyme (Saballos et al. (2009), supra; Sattler et al. (2009), supra); a point mutation in the cofactor binding site in *S. bicolor* CAD2 (Id.); disrupted secondary structure outside the active site in *S. bicolor* CAD2 (Id.); and a two-base pair adenosine insertion in a *Pinus taeda* L. CAD gene that results in a truncated enzyme (U.S. Pat. No. 6,921,643).

V. Molecular Markers Linked to Gene and Gene Variations Associated with a bm1 Phenotype, and Uses Thereof Molecular markers that are linked (e.g., tightly-linked) to a mutant cad2 gene according to the disclosure are provided. A molecular marker linked to a mutant cad2 gene according to the disclosure may be described in part, by its position in a particular region on maize chromosome 5. Molecular markers that are linked to a mutant cad2 gene according to the disclosure may include SNP markers that are within, or that reside near, the mutant cad2 gene. For example, in some embodiments, a G/A SNP located at nucleotide position 5410 in the cad2 gene from bm1 maize line, 515Dbm1, and at nucleotide position 8903 in bm1 maize line, DASbm1 (or a marker equivalent thereto), may be a molecular marker that is linked to a mutant cad2 gene according to the disclosure. In some embodiments, a G/A SNP located at nucleotide position 5410 in the cad2 gene from bm1 maize line, 515Dbm1, may be a molecular marker that is linked to a mutant cad2 gene according to the disclosure.

Additional markers may be identified, for example, by determining the frequency of recombination between the additional marker and a cad2 mutation according to the disclosure, or a molecular marker that is linked to a mutant cad2 gene according to the disclosure (e.g., the G/A SNP located at nucleotide position 5410 in bm1 maize line, 515Dbm1). Such determinations my utilize an improved method of orthogonal contrasts based on the method of Mather (1931), *The Measurement of Linkage in Heredity*, Methuen & Co., London, followed by a test of maximum likelihood to determine a recombination frequency. Allard (1956) Hilgardia 24:235-78. If the value of the recombination frequency is less than or equal to 0.10 (i.e., 10%) in the organism (e.g., maize), then the additional marker is considered to be linked to the mutant cad2 gene, and equivalent to the particular reference marker for the purposes of use in the presently disclosed methods.

Methods of using nucleic acid molecular markers that are linked to or that reside within a mutant cad2 gene according to the disclosure to identify plants with a bm1 or other reduced lignin phenotype may result in a cost savings for plant developers, because such methods may eliminate the need to cross plants comprising a mutant cad2 gene with other plant lines, and then phenotype the progenies of the cross.

A means for producing a genetically modified plant comprising a mutant maize cad2 gene is a marker that is linked to a mutant cad2 gene according to the disclosure. Thus, a means for producing a genetically modified plant comprising a mutant maize cad2 gene includes nucleic acid sequences from maize plants, the detection of any of which nucleic acid sequences provides at least a strong indication that the plant comprising the nucleic acid sequence comprises a mutant CAD2 gene according to the disclosure.

A means for identifying plants carrying a mutant maize cad2 gene is a probe that specifically hybridizes to a marker that is linked to or that resides within a mutant maize cad2 gene according to the disclosure. Specific hybridization of nucleic acids is a detectable signal, and a nucleic acid probe that specifically hybridizes to a marker that is linked to or that resides within a mutant maize cad2 gene according to the disclosure therefore presents a detectable signal when added to a sample obtained from a plant carrying a mutant cad2 gene according to the disclosure.

In some embodiments, linked markers flanking a mutant cad2 gene according to the disclosure in an organism's genome may be used to transfer segment(s) of donor parent DNA that unequivocally contain the mutant cad2 gene. In some embodiments, a method for using linked markers flanking a mutant cad2 gene according to the disclosure to transfer segment(s) of donor parent DNA that unequivocally contain the mutant cad2 gene may comprise analyzing the genomic DNA of two parent plants with probes that are specifically hybridizable to markers linked to the mutant cad2 gene; sexually crossing the two parental plant genotypes to obtain a progeny population, and analyzing those progeny for the presence of the markers linked to the mutant cad2 gene; backcrossing the progeny that contain the markers linked to the mutant cad2 gene to the recipient genotype to produce a first backcross population, and then continuing with a backcrossing program until a final progeny is obtained that comprises any desired trait(s) exhibited by the parent genotype and the mutant cad2 gene. In particular embodiments, individual progeny obtained in each crossing and backcrossing step are selected by linked marker analysis at each generation. In some embodiments, analysis of the genomic DNA of the two parent plants with probes that are specifically hybridizable to markers linked to the mutant cad2 gene reveals that one of the parent plants comprises fewer of the linked markers to which the probes specifically hybridize, or none of the linked markers to which the probes specifically hybridize.

In some embodiments, markers that are linked to or that reside within a mutant cad2 gene according to the disclosure, or the mutant cad2 gene sequence itself, may be used to introduce the mutant cad2 gene according to the disclosure into a maize plant by genetic transformation. In particular embodiments, the markers include without limitation the G/A SNP located at nucleotide position 5410 in bm1 maize line, 515Dbm1, and at nucleotide position 8903 in bm1 maize line, DASbm1, or a marker equivalent thereto. In some embodiments, a method for introducing a mutant cad2 gene according to the disclosure into a maize plant by genetic recombination may comprise analyzing the genomic DNA of a plant (e.g., a maize plant) with probes that are specifically hybridizable to markers linked to the mutant cad2 gene or the mutant cad2 gene itself to identify the mutant cad2 gene in the plant; isolating a segment of the genomic DNA of the plant comprising the mutant cad2 gene, for example, by extracting the genomic DNA and digesting the genomic DNA with one or more restriction endonuclease enzymes; optionally amplifying the isolated segment of DNA; introducing the isolated segment of DNA into a cell or tissue of a host maize plant; and analyzing the DNA of the host maize plant with probes that are specifically hybridizable to markers linked to the mutant cad2 gene or the mutant cad2 gene itself to identify the mutant cad3 gene in the host maize plant. In particular embodiments, the isolated segment of DNA may be introduced into the host maize plant such that it is stably integrated into the genome of the host maize plant.

In some embodiments, markers that are linked to or that reside within a mutant cad2 gene according to the disclosure, or the mutant cad2 gene sequence itself, may be used to introduce a mutant cad2 gene according to the disclosure into other organisms, for example, plants. In particular embodiments, the markers include without limitation the G/A SNP located at nucleotide position 5410 in bm1 maize line, 515Dbm1, and at nucleotide position 8903 in bm1 maize line, DASbm1, or a marker equivalent thereto. In some embodiments, a method for introducing the mutant cad2 gene according to the disclosure into an organism other than maize (e.g., soybean; alfalfa; wheat; rapeseed; rice; and sorghum) may comprise analyzing the genomic DNA of a plant other than a maize plant with probes that are specifically hybridizable to markers linked to the mutant CAD2 gene according to the disclosure or the mutant cad2 gene itself to identify the mutant cad2 gene in the plant; isolating a segment of the genomic DNA of the plant comprising the mutant cad2 gene, for example, by extracting the genomic DNA and digesting the genomic DNA with one or more restriction endonuclease enzymes; optionally amplifying the isolated segment of DNA; introducing the isolated segment of DNA into an organism other than maize; and analyzing the DNA of the organism other than maize with probes that are specifically hybridizable to markers linked to the mutant cad2 gene according to the disclosure or the mutant cad2 gene itself to identify the mutant cad2 gene in the organism. In particular embodiments, the isolated segment of DNA may be introduced into the organism such that it is stably integrated into the genome of the organism.

In some embodiments, markers that are linked to or that reside within a mutant cad2 gene according to the disclosure, or the mutant cad2 gene sequence itself, may be used to identify a plant with a bm1 or other reduced lignin phenotype. In particular embodiments, the plant is a maize plant. In some embodiments, nucleic acid molecules (e.g., genomic DNA or mRNA) may be extracted from a plant. The extracted nucleic acid molecules may then be contacted with one or more probes that are specifically hybridizable to markers linked to a mutant cad2 gene according to the disclosure or the mutant cad2 gene itself. Specific hybridization of the one or more probes to the extracted nucleic acid molecules is indicative of the presence of a bm1 or other reduced lignin phenotype in the plant.

Primer Design and Linkage Screening.

Oligonucleotide probes (e.g., primers) may be designed to specifically detect markers that are physically located in, near, or between cad2 that are linked to a bm1 mutation. In general, an oligonucleotide probe may be designed that specifically hybridizes to only one allele of a marker. In some embodiments, two oligonucleotide probes are designed to detect a bm1 marker, such that one specifically hybridizes to the bm1 allele to which the other probe does not specifically hybridize, and the other specifically hybridizes to the wild-type CAD2 allele (or different bm1 allele) to which the other probe does not specifically hybridize. As is understood by those of skill in the art, the length or composition of oligonucleotide probes for a particular marker may be varied according to established principles without rendering the probe non-specific for one allele of the marker.

In some embodiments, the oligonucleotide probes may be primers. In specific embodiments, primers may be designed to detect markers in a KASPar™ genotyping assay. In particular embodiments, primers may be designed to detect markers linked to the bm1 phenotype in maize using a KASPar™ genotyping assay. In these and further embodiments, the detection system may provide a high-throughput and convenient format for genotyping individuals in a mapping population, which may greatly facilitate the identification of individuals carrying a particular gene or trait, and may also greatly facilitate the implementation or execution of a marker-assisted selection program.

In specific embodiments, the oligonucleotide probes may be primers designed to detect markers in a TAQMAN® genotyping assay. This method utilizes specific primers to amplify a region of DNA containing a marker closely linked to a bm1 mutation and fluorescent labeled probes specific to the marker. The probe that specifically hybridizes to the bm1 allele may be labeled with a fluorescent dye such as FAM, while the probe that specifically hybridizes to the wild-type CAD2 allele (or different bm1 allele) may be labeled with a different fluorescent dye such, as VIC. The data is analyzed as the presence or absence of a fluorescent dye signal. The detection system may provide a high-throughput and convenient format, such as multiplexing for genotyping individuals in a mapping population, which may greatly facilitate the identification of individuals carrying a particular gene or trait, and may also greatly facilitate the implementation or execution of a marker-assisted selection program.

Thus, also described herein is a gene specific end-point TaqMan® PCR assay, generally useful for zygosity analysis of bm1 corn or putative bm1 corn. In particular embodiments, a gene specific end-point TaqMan® PCR assay may be used to analyze the zygosity of corn for a bm1 mutation.

Primers and probes for use in a gene specific end-point TaqMan® PCR assay may be designed based on a known mutation in the gene of interest. For example, primers and probes for a bm1-specific assay may be designed based on a 3444-bp insertion in the first intron of the cad2 gene. In biplex reactions, wherein oligonucleotides specific to the mutation (e.g., bm1) and the undisrupted wild-type gene (e.g., CAD2) are used in the same assay, the specific oligonucleotides will selectively amplify sequence from either or both of the mutated gene and/or the wild-type gene that is present in a genomic DNA sample.

In some embodiments, a bm1-specific assay amplifies a fragment that is unique to the 3444 bp of nucleotide sequence that was inserted into the wild-type genomic CAD2 gene. In some embodiments, a wild-type CAD2 gene-specific assay amplifies a fragment of the CAD2 gene that comprises the junction site where 3444 bp of nucleotide sequence was inserted into the wild-type CAD2 gene. In certain embodiments, a target-specific oligonucleotide probe hybridizes under high-stringency conditions to a target sequence in a genomic DNA sample between two PCR primers.

Target-specific oligonucleotides may be labeled, for example, with fluorescent dyes (e.g., FAM, VIC, and MGB-NFQ), which may allow rapid quantification of a target-specific fluorescent signal. PCR products may be measured after a pre-determined number of cycles, for example, when the reaction is in the early exponential phase. Negative control samples may comprise genomic DNA from any corn variety, for example, without a bm1 mutation. Positive control samples may comprise genomic DNA from a corn variety with a bmr mutation, such as a bm1 insertion mutation in the CAD2 gene. Control hemizygous samples may comprise either genomic DNA from a corn variety predetermined to be hemizygous for a bm1 mutation; or a hemizygous sample may comprise equal proportions of negative control DNA to DNA from a corn variety predetermined to be homozygous for a bm1 mutation.

DNA may be isolated (for example, extracted, and purified) from corn plant tissue by methods known to those of skill in the art. Commercial kits for DNA isolation are available, for example, from Qiagen, Inc. In some embodiments, leaf discs from a particular plant are punched and transferred into collection tubes. The puncher may be cleaned after each sampling with 70% alcohol, rinsing in water, and drying. DNA extraction buffers may be prepared according to the manufacturer's recommendations. DNA may then be isolated using the kit according to the manufacturer's instructions. Finally, the concentration of the isolated DNA may be determined using, for example, a Quant-iT™ PicoGreen® Quantification Kit (Invitrogen, Carlsbad, Calif.) and a spectrophotometer, or by any other suitable technique.

Once primers, probes, and genomic DNA sample(s) have been prepared or otherwise made available, a PCR reaction may be conducted to identify nucleic acid sequences of interest (e.g., sequences particular to a bmr mutation) in the genomic DNA sample(s). In particular embodiments, individual PCR reaction mixtures are prepared that contain all the reaction components, except the genomic DNA sample(s). For a biplex reaction comprising primers and gene-specific probes for bm1 mutant and wild-type CAD2 corn, the reaction mixture may comprise enzyme, reaction buffer, forward and reverse primers for the bm1 mutation, forward and reverse primers for the wild-type CAD2 gene, a gene-specific probe for the bm1 mutation, a gene-specific probe for the CAD2 gene, and water. In some PCR assay systems (e.g., TaqMan® PCR assays), enzyme and buffer may be present in a single kit component (e.g., TaqMan® genotyping master mix; Applied Biosystems, Foster City, Calif., Catalog #4371355).

Once the reaction mixture is otherwise prepared, genomic DNA sample(s) may be added, and the reaction commenced. It is not necessary to normalize the amounts of genomic DNA in a sample. However, the skilled artisan may attain best results by using genomic DNA samples with relatively equal concentrations.

In some embodiments, a PCR assay (e.g., a TagMan® PCR assay) can be set up with appropriate controls. For example, a reaction in a multi-well plate may be performed with control wells comprising: (1) negative control(s) with reagents but no DNA sample; (2) homozygous positive control(s) comprising bm1 corn genomic DNA; (3) and hemizygous positive control(s), as described above. DNA is then amplified by PCR under suitable cycle conditions. For example, in some embodiments using a GenAmp® PCR System 9700, there may be a single initial denaturation cycle at 95° C. for 15 minutes, followed by 30 cycles of denaturation (92° C. for 15 seconds) and annealing/extension (60° C. for 60 seconds). Those of skill in the art understand that PCR cycle conditions may be varied according to the practitioner's discretion, and comparable results obtained.

A PCR assay (e.g., an end-point TaqMan® PCR assay) may be used for genotype and/or zygosity analysis of bmr corn or putative bmr corn. In some embodiments, a gene-specific oligonucleotide probe may be labeled with a reporter (e.g., a fluorescent moiety). For assays using fluorometric detection, PCR reaction products may be analyzed in a spectrofluorometer (e.g., Tecan GENios™; Männedorf, Switzerland) using excitation and emission wavelength settings appropriate for the detection of the probe(s). For example, the fluorescent dye, FAM, may be measured with an excitation wavelength of 485 nm, and an emission wavelength of 535 nm. Alternatively, the fluorescent dye, VIC, may be measured with an excitation wavelength of 525 nm, and an emission wavelength of 560 nm.

Following the completion of the PCR reaction and probe detection, a table and distribution graph may be generated using, for example, any suitable computer graphics software. Results obtained with wild-type, hemizygous, and homozygous DNA of similar genotypic background may serve as negative and positive controls. In a segregating population, three clusters of data points may be obtained allowing the visual determination of a sample result as likely belonging to one of the segregated clusters. Alternatively, data analysis computer software may be used to calculate the probability that a sample result belongs to each segregated cluster, with the most probable cluster serving as the sample designation. When a visual determination is made, the boundary of each cluster may be arbitrary, for example, when three clusters of data points are clearly visible.

Raw fluorescence intensity data may also be analyzed directly from a plate reader using a suitable analysis package, such as KLIMS™ (KBioscience laboratory information management system). A graph with the relative fluorescence units (RFU) of a fluorescence signal generated by a specific probe for a mutant allele plotted on one axis, and the RFU of a fluorescence signal generated by a specific probe for the wild-type allele plotted on the other axis may be generated. Zygosity determinations may then be made based on the cluster separation in a graphical display of the data.

Samples that do not contain mutant genomic DNA (e.g., a bmr mutation) may only result in fluorescence readings of the wild-type PCR product. Samples containing hemizygous or homozygous mutant genomic DNA may result in RFU readings for the mutant-specific probe higher than that of a negative background control. If a sample yields no adequate results, the genomic DNA in the sample may not be of adequate quality and/or quantity, and a new DNA preparation and/or new PCR reaction should be performed. Preferably, a negative control sample containing no DNA sample shows very low detection of gene-specific probe(s). It is also preferable that known homozygous controls show only high detection of the mutant or wild-type DNA in the control, and that known hemizygous controls show both high detection of the mutant and wild-type DNA.

A "test run" of the PCR method and genotype and/or zygosity determination may be performed with all appropriate controls prior to screening of samples. Further optimization of the methods may be desirable for components that may differ among uses (e.g., method of genomic DNA preparation, Taq DNA polymerase, oligonucleotides, laboratory equipment, etc.). PCR and thermal cycling conditions may be established that amplify both mutant and/or wild-type sequences in a known genomic DNA template with acceptable levels of probe detection (e.g., acceptable RFU for fluorescently labeled oligonucleotide probes).

VI. Organisms Having Reduced CAD2 Activity and Uses Thereof

A. Organisms Having Reduced CAD2 Activity

Some embodiments of the present invention also provide an organism including a nucleic acid molecule comprising a mutant cad2 gene according to the disclosure, a nucleic acid sequence that is specifically hybridizable to a mutant cad2 gene according to the disclosure, or a functional variant of a mutant cad2 gene according to the disclosure. A suitable organism can be any suitable plant, yeast, or bacterium. By way of non-limiting example, a plant comprising the aforementioned sequences may be a plant of agronomic value, for example and without limitation: maize; soybean; alfalfa; wheat; rapeseed; rice; sorghum; beet; various vegetables including cucumber, tomato, peppers, etc.; various trees including apple, pear, peach, cherry, redwood, pine, oak, etc.; and various ornamental plants. In particular embodiments, the organism may be a plant that is used to produce silage.

Plant cells comprising a mutant cad2 gene according to the disclosure, a nucleic acid sequence that is specifically hybridizable to a mutant cad2 gene according to the disclosure, or a functional variant of a mutant cad2 gene according to the disclosure, may be cultured and kept as plant tissue culture cells, or certain plant hormones known in the art can be added to the culture media, thereby causing the plant tissue culture cells to differentiate and form a new plant variety, which new plant variety may exhibit a bm1 or other reduced lignin phenotype. Such plant culturing methods useful in these and other embodiments are routine and well-known in the art.

Some embodiments of the invention provide a virus (e.g., a bacteriophage, or plant virus) comprising a mutant cad2 gene according to the disclosure, a nucleic acid sequence that is specifically hybridizable to a mutant cad2 gene according to the disclosure, or a functional variant of a mutant cad2 gene according to the disclosure.

B. Silage Produced from Plants Having Reduced CAD2 Activity

Disclosed herein are methods for increasing the meat quantity of a silage-fed animal that use silage produced from plant varieties exhibiting reduced lignin content to improve daily gain and feed efficiency when compared to conventional corn silage in a finishing ration. Such silage can effectively replace grain corn in a beef finishing ration. In some embodiments, the method comprises providing silage produced from a plant variety comprising a mutant cad2 gene according to the disclosure, feeding the animal with the silage produced from the plant variety comprising a mutant cad2 gene according to the disclosure, and producing meat or meat products from the animal. In these and further embodiments, the silage-fed animal may be a ruminant. In particular embodiments, the silage-fed animal may be any silage-fed animal, for example, cattle, sheep, swine, horses, goats, bison, yaks, water buffalo, and deer.

In some embodiments, methods provided for increasing the meat quantity of a silage-fed animal further comprise an act selected from the group consisting of: placing the silage in a container configured for shipping, and associating indicia with the silage, wherein the indicia is capable of directing an end-user on how to administer the silage to the animal. Thus, kits comprising silage are provided, such that the kits allow an end-user to increase the meat quantity of a silage-fed animal.

Also disclosed are beef finishing rations, wherein the beef finishing ration comprises corn silage comprising a mutant cad2 gene according to the disclosure. Also disclosed are meat and meat products prepared from an animal that has been fed such silage.

Production of silage from plants (e.g., maize) having reduced CAD2 activity.

During ensilage, the cells of the plant are still alive and metabolically active, and ongoing metabolism by plant cells and microorganisms in the compressed silage forms carbon dioxide and heat by using air trapped in the ensiled plant material. Anaerobic metabolic conditions develop as the level of carbon dioxide in the silage increases. Desirable bacteria begin the fermentation process when plant respiration stops. If too much air is present, or if carbon dioxide escapes, an anaerobic condition may fail to develop. In this case, respiration may continue, and the respiring plant cells may use too much sugar and carbohydrates. This may waste nutrients needed by desirable bacteria to preserve the plant material as silage, and may yield an inferior silage. To avoid this undesirable effect, packing and covering of the silage immediately after filling may be important.

Once respiration by the plant cells ceases, acetic and lactic acids are produced by bacteria that feed on the available starches and simple sugars in the ensiled corn. To promote growth of desirable bacteria, the silage may contain a low amount of air, temperatures between 80° and 100° F., and starches and sugars for food. Fermentation may continue until the acidity of the silage is high enough to stop bacterial growth. In some examples, the desired degree of acidity is a pH of about 4.2. This degree of acidity may occur within 3 weeks after the silo is filled.

Seepage may occur if moisture in the forage is excessively high. Seepage involves the drainage of leachate (excess moisture from silage and pulp) out of the silage, which generally enters the environment as a serious pollutant. Through seepage, desirable components (e.g., nitrogenous compounds, such as protein; and minerals) of the silage may be lost. Seepage generally reaches its peak on about the fourth day after ensiling. Therefore to avoid, for example, the loss of desirable silage components from the silage, moisture content of forage going into the silo may be chosen to be sufficiently low to reduce or prevent seepage loss. However, silage that is too dry may not pack adequately, and may also exhibit a high loss of desirable components from the silage as a consequence of excessive fermentation and molding.

Plants may be ensiled at a dry matter content of about 30-40% to enable an optimal fermentation process, and to minimize losses during fermentation. To reach a dry matter content of about 30-40%, it may be desirable to let the plant material dry down in a field after mowing and before chopping with, for example, a forage harvester. When preparing silage, the grain may be harvested together with the rest of the plant. To increase the availability of nutrients in the silage for uptake in the intestinal tract of a silage-fed animal, it may be desirable to crush the grain during the chopping process.

Harvested plant material (e.g., maize plant material) may be transferred into a silo. Non-limiting examples of silos that may be useful for silage preparation include: a bunker silo, a silage heap, a concrete stave silo, or a tower silo. The plant material is compacted in the silo to remove air from the plant material, and enable anaerobic fermentation. It may be desirable to seal the silo with a plastic silage film, depending on the type of silo used. Use of a plastic cover on a trench silo, a bunker silo, or a large-diameter tower silo, may materially cut feed losses. Typically, the cover is applied immediately after the last load of plant material is packed in the silo, and the plastic covers are weighted to hold them firmly on the surface of the silage. Alternatively, the plant material may be prepared for fermentation during ensiling by baling the plant material, and wrapping the bales in silage film for sealing. On trench or bunker silos, it may be desirable to mound or crown the forage. This may facilitate drainage of rain water off the silo.

Additives may optionally be added to the plant material to improve fermentation. Examples of plant material additives that may be desirable in particular applications include microbial additives, such as *Lactobacillus* spp. and other inoculants; acids such as propionic acid, acetic acid or formic acid; or sugars. As will be readily understood by those of skill in the art, other methods for producing silage other than those specifically recited herein may also be used.

One advantage of silage production is that the process may have no influence on the composition, the amount, or availability of nutritive substances contained within the plant material used for producing the silage. On the contrary, purposes of the process itself are generally to both keep the quality of the plant material as it was prior to using such material for producing silage, and to preserve the positive properties of the plant material for an extended period of time. In this way, the plant material can be used as forage long after the plant material has been harvested.

Corn may be harvested for silage after the ear is well-dented, but before the leaves dry to the point that they turn brown. At this stage of growth, the ear may have accumulated most of its potential feeding value, but there may also have been little loss from the leaves and stalks. Thus, the quantity and quality of corn silage may be at its peak when the plant material is harvested during this stage. Ears usually will be well-dented when the ears are between 32-35% moisture. As time elapses after the ear has become well-dented, the feeding value of the plant material may decrease while field losses may increase. Corn harvested for silage at the milk stage (grain head releases a white liquid when opened) or dough stage (grain head begins to turn a doughy consistency) may yield less feed nutrients per acre than if it was harvested later. Plant material from corn may also ferment improperly in a silo if it is harvested too soon.

Maturity usually refers to the time when the ear has accumulated nearly all of its dry matter production potential. Temperatures during growth may influence the maturity rate of the grain, particularly during the autumn. For example, the ear's full dry matter potential may not be achieved if there are excessively cool temperatures and/or cloudy weather. Corn silage that is cut late and has brown and dead leaves and stalks may make adequate silage, but total production per acre may be sharply reduced. Significant field losses have been found when silage is made late into the fall or early winter. Also, a reduction in the amount of dry matter stored in the silo may be found with respect to silage that is cut late.

Corn that has been damaged, for example, by drought, high temperatures, blight, frost, or hail, may be salvaged for silage. However, the quality of such salvaged silage may not be as high as silage produced from undamaged corn that has reached the dent stage. The feeding value of the silage may depend upon both the state of the corn's development, and how the corn is handled after it has been damaged. Common observations of silage from immature corn include: higher moisture; fermentation in a different manner than mature corn; sour odor; and increased laxative effect. Corn that has experience from frost typically has a low carotene content. It will dry out quickly and lose leaves. Thus, it may be desirable to add water to corn that has frosted and become too dry. It may also be desirable to add water to drought corn.

It may be desirable for immature corn that has been damaged by extremely high temperatures to not be ensiled immediately. Immature, heat-damaged corn may never produce ears, but some additional stalk growth may result from delaying harvest. Additional stalk growth will result in additional feed. If corn is harvested for silage too soon after the plants have been extensively damaged by heat, the stalk may have too much moisture to produce a high-quality silage. Corn harvested too soon after extensive heat damage that has too much moisture may also lose nutrients through seepage.

Possible problems with silage made from salvaged corn include its lack of energy content due to reduced grain formation, and improper fermentation resulting from excessive dryness of the damaged plant. As is known by those of skill in the art, these problems may be corrected, at least in part, by supplementation with an additional energy source, and addition of moisture, respectively.

Corn silage may be cut into particles that are ½" to ¾" in length. Particles of this size may pack more firmly, and may additionally be more palatable to silage-fed animals. Very finely cut silage that is shorter than ½" in length may be made with a recutter. Use of very finely cut silage increases the amount of dry matter that can be stored, e.g., in a silo. However, very finely cut silage may be less palatable to an animal that is to be fed the silage.

If silage is too dry, it may be desirable to add water, for example, to establish airtight conditions. Generally, four gallons of water may be added per ton of silage for each 1 percent desired rise in moisture content. It is understood that more or less water may be required, and measurements may be taken during the ensiling process to ensure that enough, but not too much, water is added. The water may be added as the silo is being filled. If the water is added after the silo is filled, it may seep down the silo walls, and therefore not permeate the silage mass. This seepage may cause leaching of silage nutrients, and may break the air seal and lead to improper fermentation.

High-quality silage may be made without the addition of any additives or preservatives. However, additives may be added to silage to increase one or more characteristics of the silage. For example, molasses and grain may be added to corn forage at the time of ensiling.

With large-capacity silos and high-speed filling methods, distribution and packing of silage in silos should be monitored. Improper distribution and packing may cause excessive seepage, poor fermentation, and/or losses in storage capacity. Half the capacity of a cylindrical silo is in the silo's outermost edge. For example, for a cylindrical silo that is 14' in diameter, half its capacity is in the outermost 2' of its diameter. If material in this outside area is packed too loosely, the capacity of the silo may be significantly reduced. Thus, tower silos may be equipped with a distributor that facilitates proper silage distribution and packing.

A loss of nutrients occurs in all silage during the ensiling process, due to the presence of living microorganisms that carry out the fermentation process. The amount of nutritional value lost during the ensiling process depends upon, inter alia, the exclusion air during filling, and the prevention of carbon dioxide loss. Carbon dioxide is necessary to arrest respiration of the ensiled plant cells; and to prevent seepage loss, undesirable fermentation, and/or spoilage due to exposure of the plant material surface. Therefore, good ensiling practices generally lead to higher quality silage with a maximal nutrient content.

Silage from plants (e.g., maize) having reduced CAD2 activity in a finishing ration.

Silage from plants having reduced CAD2 activity have a reduced lignin content when compared to wild-type plants of the same variety, and may be chopped into longer particles than normal silage, whether it is processed or not. NDF digestibility of bm1 silage may be higher than with normal silage. The composition of freshly made silage is not necessarily reflective of the composition of feed that the silage-fed animal will eat. Therefore, fermented samples may be analyzed after a period of time in the silo. For example, samples may be analyzed after at least two weeks, or at least two months, in the silo.

Once silage from plants having reduced CAD2 activity has been prepared, and the silage has been determined to be ready to be fed to an animal, the silage may be included in a finishing ration to be fed to an animal that will be used for meat, or meat product, production. In some examples, the finishing ration comprising silage may not comprise grain corn, for example, dry rolled corn, or ground corn. Typical finishing rations comprise at least about 11% protein, about 60 MCal of Net Energy, about 0.5% Calcium, about 0.35% Phosphorous, and about 0.6% Potassium. In some examples, it is an advantage that a finishing ration exhibits a higher feed efficiency (G:F). In particular examples, a finishing ration that does not comprise grain corn may result in average daily gains in an animal fed the finishing ration that are comparable to the average daily gain that would result from a normal finishing rations that uses grain corn as an energy source.

In some examples, a finishing ration is produced using silage from plants (e.g., maize) comprising a mutant cad2 gene according to the disclosure, wherein the finishing ration comprises between about 15% and about 30% silage. Thus, a finishing ration may comprise, for example, 13%, 14%, 15%, 16%, 17%, 18%, 19%, 20%, 21%, 22%, 23%, 24%, 25%, 26%, 27%, 28%, 29%, 30%, 31%, 32%, or 33% silage. In particular examples, a finishing ration is produced using bm1 corn silage. In some examples, a finishing ration comprising at least one fiber source is produced. Thus, a finishing ration may comprise, for example, one, two, three, four, or more than four fiber sources. In some examples, a finishing ration comprising at least one corn co-product is produced. Thus, a finishing ration may comprise, for example, one, two, three, four, or more than four corn co-products. In some examples, a finishing ration comprising less than 60% dry matter is produced. In further examples, a finishing ration comprises less than 55% dry matter. In some specific examples, a finishing ration comprises less than 50% dry matter. Thus, a finishing ration may comprise, for example, 59%, 58%, 57%, 56%, 55%, 54%, 53%, 52%, 51%, 50%, 49%, 48%, 47%, 46%, 45%, 44%, 43%, 42%, 41%, or 40% dry matter.

C. Stacking of a Mutant cad2 Gene with One or More Additional Trait(s)

In some embodiments, a mutant cad2 gene according to the disclosure may be introduced into a plant comprising one or more desirable trait(s), in order to produce a plant with both a bm1 or other reduced lignin phenotype, and the one or more desirable trait(s). The process of introducing a mutant cad2 gene according to the disclosure into a plant comprising one or more desirable traits (either by introduction into an existing plant line, or by introducing the mutant cad2 gene into the plant at the same time as an additional nucleic acid molecule that provides a desirable trait) is referred to herein as "stacking." In some examples, by stacking a mutant cad2 gene with one or more desirable traits, a bm1 or other reduced lignin phenotype may be combined with the one or more desirable traits. For example, stacking of the bm1 trait with the bm3 trait may result in further increases in silage digestibility, and a very significant improvement in the yield of fermentable sugars in biomass hydrolysis without pre-treatment.

Examples of traits that may be desirable for combination with a bm1 or other reduced lignin phenotype include, without limitation: cytoplasmic male sterility; plant disease resistance genes (See, e.g., Jones et al. (1994) Science 266:789 (tomato Cf-9 gene for resistance to *Cladosporium fulvum*); Martin et al. (1993) Science 262:1432 (tomato Pto gene for resistance to *Pseudomonas syringae*); and Mindrinos et al. (1994) Cell 78:1089 (RSP2 gene for resistance to *Pseudomonas syringae*)); a gene conferring resistance to a pest; a *Bacillus thuringiensis* protein, a derivative thereof, or a synthetic polypeptide modeled thereon (See, e.g., Geiser et al. (1986) Gene 48:109 (Bt δ-endotoxin gene; DNA molecules encoding δ-endotoxin genes can be purchased from American Type Culture Collection (Manassas, Va.), for example, under ATCC Accession Nos. 40098; 67136; 31995; and 31998)); a lectin (See, for example, Van Damme et al. (1994) Plant Molec. Biol. 24:25 (*Clivia miniata* mannose-binding lectin genes)); a vitamin-binding protein, e.g., avidin (See International PCT Publication US93/06487 (use of avidin and avidin homologues as larvicides against insect pests)); an enzyme inhibitor; a protease or proteinase inhibitor (See, e.g., Abe et al. (1987) J. Biol. Chem. 262:16793 (rice cysteine proteinase inhibitor); Huub et al. (1993) Plant Molec. Biol. 21:985 (tobacco proteinase inhibitor I; and U.S. Pat. No. 5,494,813); an amylase inhibitor (See Sumitani et al. (1993) Biosci. Biotech. Biochem. 57:1243 (*Streptomyces nitrosporeus* alpha-amylase inhibitor)); an insect-specific hormone or pheromone, e.g., an ecdysteroid or juvenile hormone, a variant thereof, a mimetic based thereon, or an antagonist or agonist thereof (See, e.g., Hammock et al. (1990) Nature 344:458 (inactivator of juvenile hormone)); an insect-specific peptide or neuropeptide that disrupts the physiology of the affected pest (See, e.g., Regan (1994) J. Biol. Chem. 269:9 (insect diuretic hormone receptor); Pratt et al. (1989) Biochem. Biophys. Res. Comm. 163:1243 (allostatin from *Diploptera puntata*); U.S. Pat. No. 5,266,317 (insect-specific, paralytic neurotoxins)); an insect-specific venom produced in nature by a snake, a wasp, or any other organism (See, e.g., Pang et al. (1992) Gene 116:165 (a scorpion insectotoxic peptide)); an enzyme responsible for a hyperaccumulation of a monoterpene, a sesquiterpene, a steroid, hydroxamic acid, a phenylpropanoid derivative or another non-protein molecule with insecticidal activity; an enzyme involved in the modification, including the post-translational modification, of a biologically active molecule, e.g., a glycolytic enzyme; a proteolytic enzyme; a lipolytic enzyme; a nuclease; a cyclase; a transaminase; an esterase; a hydrolase; a phosphatase; a kinase; a phosphorylase; a polymerase; an elastase; a chitinase; or a glucanase, whether natural or synthetic (See International PCT Publication WO 93/02197 (a callase gene); DNA molecules which contain chitinase-encoding sequences (for example, from the ATCC, under Accession Nos. 39637 and 67152); Kramer et al. (1993) Insect Biochem. Molec. Biol. 23:691 (tobacco hornworm chitinase); and Kawalleck et al. (1993) Plant Molec. Biol. 21:673 (parsley ubi4-2 polyubiquitin gene); a molecule that stimulates signal transduction (See, e.g., Botella et al. (1994) Plant Molec. Biol. 24:757 (calmodulin); and Griess et al. (1994) Plant Physiol. 104:1467 (maize calmodulin); a hydrophobic moment peptide (See, e.g., International PCT Publication WO 95/16776 (peptide derivatives of Tachyplesin which inhibit fungal plant pathogens); and International PCT Publication WO 95/18855 (synthetic antimicrobial peptides that confer disease resistance)); a membrane permease, a channel former, or a channel blocker (See, e.g., Jaynes et al. (1993) Plant Sci 89:43 (a cecropin-β lytic peptide analog to render transgenic plants resistant to *Pseudomonas solanacearum*); a viral-invasive protein or a complex toxin derived therefrom (See, e.g., Beachy et al. (1990) Ann. rev. Phytopathol. 28:451 (coat protein-mediated resistance against alfalfa mosaic virus, cucumber mosaic virus, tobacco streak virus, potato virus X, potato virus Y, tobacco etch virus, tobacco rattle virus and tobacco mosaic virus)); an insect-specific antibody or an immunotoxin derived therefrom (See, e.g., Taylor et al., Abstract #497, Seventh Int'l Symposium on Molecular Plant-Microbe Interactions (Edinburgh, Scotland) (1994) (enzymatic inactivation via production of single-chain antibody fragments); a virus-specific antibody (See, e.g., Tavladoraki et al. (1993) Nature 366:469 (recombinant antibody genes for protection from virus attack)); a developmental-arrestive protein produced in nature by a pathogen or a parasite (See, e.g., Lamb et al. (1992) Bio/Technology 10:1436 (fungal endo α-1,4-D-polygalacturonases facilitate fungal colonization and plant nutrient release by solubilizing plant cell wall homo-α-1,4-D-galacturonase; Toubart et al. (1992) Plant J. 2:367 (endopolygalacturonase-inhibiting protein)); and a developmental-arrestive protein produced in nature by a plant (See, e.g., Logemann et al. (1992) Bio/Technology 10:305 (barley ribosome-inactivating gene providing increased resistance to fungal disease)).

Further examples of traits that may be desirable for combination with a bm1 or other reduced lignin phenotype include, without limitation, genes that confer resistance to a herbicide (Lee et al. (1988) EMBO J. 7:1241 (mutant ALS enzyme); Mild et al. (1990) Theor. Appl. Genet. 80:449 (mutant AHAS enzyme); U.S. Pat. Nos. 4,940,835 and 6,248,876 (mutant 5-enolpyruvylshikimate-3-phosphate synthase (EPSPs) genes providing glyphosate resistance); U.S. Pat. No. 4,769,061 and ATCC accession number 39256 (aroA genes); glyphosate acetyl transferase genes (glyphosate resistance); other phosphono compounds from *Streptomyces* species, including *Streptomyces hygroscopicus* and *Streptomyces viridichromogenes*) such as those described in European application No. 0 242 246 and DeGreef et al. (1989) Bio/Technology 7:61 (glufosinate phosphinothricin acetyl transferase (PAT) genes providing glyphosate resistance); pyridinoxy or phenoxy proprionic acids and cyclohexones (glyphosate resistance); European patent application No. 0 333 033 and U.S. Pat. No. 4,975,374 (glutamine synthetase genes providing resistance to herbicides such as L-phosphinothricin); Marshall et al. (1992) Theor. Appl. Genet. 83:435 (Acc1-S1, Acc1-S2, and Acc1-S3 genes providing resistance to phenoxy proprionic acids and cyclohexones, such as sethoxydim and haloxyfop); WO 2005012515 (GAT genes providing glyphosate resistance); WO 2005107437 (Genes conferring resistance to 2,4-D, fop and pyridyloxy auxin herbicides); and an herbicide that inhibits photosynthesis, such as a triazine (psbA and gs+ genes) or a benzonitrile (nitrilase gene) (See, e.g., Przibila et al. (1991) Plant Cell 3:169 (mutant psbA genes); nucleotide sequences for nitrilase genes are disclosed in U.S. Pat. No. 4,810,648, and DNA molecules containing these genes are available under ATCC Accession Nos. 53435, 67441, and 67442; and Hayes et al. (1992) Biochem. J. 285:173 (glutathione S-transferase)).

Further examples of traits that may be desirable for combination with a bm1 or other reduced lignin phenotype include, without limitation, genes that confer or contribute to a value-added trait, for example, modified fatty acid metabolism (See, e.g., Knultzon et al. (1992) Proc. Natl. Acad. Sci. U.S.A. 89:2624 (an antisense gene of stearyl-ACP desaturase to increase stearic acid content of the plant)); decreased phytate content (See, e.g., Van Hartingsveldt et al. (1993) Gene 127:87 (an *Aspergillus niger* phytase gene enhances breakdown of phytate, adding more free phosphate to the transformed plant); and Raboy et al. (1990) Maydica 35:383 (cloning and reintroduction of DNA associated with an allele responsible for maize mutants having low levels of phytic acid)); and modified carbohydrate composition effected, for example, by transforming plants with a gene coding for an enzyme that alters the branching pattern of starch (See, e.g., Shiroza et al. (1988) J. Bacteol. 170:810 (*Streptococcus* mutant fructosyltransferase gene); Steinmetz et al. (1985) Mol. Gen. Genet. 20:220 (levansucrase gene); Pen et al. (1992) Bio/Technology 10:292 (α-amylase); Elliot et al. (1993) Plant Molec. Biol. 21:515 (tomato invertase genes); Sogaard et al. (1993) J. Biol. Chem. 268:22480 (barley α-amylase gene); and Fisher et al. (1993) Plant Physiol. 102:1045 (maize endosperm starch branching enzyme II)).

D. Other Uses of a Plant Having Reduced CAD2 Activity

Many agronomical or industrial applications besides the production of silage concern desired plant products, the yields of which are directly linked to the content and/or composition of lignin in the plant cell wall. Examples of such products and applications include without limitation: products used in paper production, and the production of energy, for example, in the form of biofuels. Plants comprising a mutant cad2 gene according to the disclosure may have a bm1 or other reduced lignin phenotype. As will be appreciated by those of skill in the art, plant products derived from such plants may be expected to have distinguishing characteristics from a wild-type plant of the same variety, which distinguishing characteristics may be desirable. Thus, any use of a plant comprising a mutant cad2 gene according to the disclosure that takes advantage of an expected bm1 or other reduced lignin phenotype in the plant is within the scope of the disclosure.

The following examples are provided to illustrate certain particular features and/or embodiments. The examples should not be construed to limit the disclosure to the particular features or embodiments exemplified.

EXAMPLES

Example 1

Cloning and Sequencing of CAD2 Genes from Two Bm1 Lines

Corn leaf samples from inbred lines 515Dbm1 (bm1 mutant), 6XN442 (wild-type), and DASbm1 were used. DASbm1 is a novel, naturally-occurring bmr mutant discovered in a CV5123/GR8207 genetic background. The original $F_1$ generation from which the DASbm1 mutation originated was created in a breeding crossing block in the summer of 2003 by using GR8207 as the male, and crossing it to female CV5123. This cross was self-pollinated in the winter nursery of 2003 and the $F_2$ ears were then bulked to generate $F_2$ seeds. The $F_2$ population was planted in the summer of 2004, and 60 self-pollinated ears were selected for advancement into grain testing. These 60 ears were sent to winter nursery in 2004 for self-pollination to create a go-forward $S_2$ ear selection. The $S_2$ ears were then planted in the 2006 summer nursery.

The discovery of a bmr mutant was made while walking the nursery looking at inbred lines. A row showing a pronounced BMR phenotype was identified. This row was ear 31 of the 60 ears selected from the CV5123/GR8207-B population, and showed very close resemblance in plant structure to the other 59 ears selected except for having the BMR trait. It could not initially be determined if the mutant was a bm3, bm1, or other mutation. $S_2$ plants were then self-pollinated, and seeds were collected and saved. In the summer of 2007, the $S_3$ seeds were planted, and all plants still showed the BMR trait. The $S_3$ plants were self-pollinated to create $S_4$ ears, and the line was noted as of possible interest for silage production. In the summer of 2008, test crosses were made to both known bm1 and bm3 inbred lines to determine the background of the bmr mutant. In the summer of 2009, the test cross seeds were grown out in a progeny test, and it was determined the mutation was a new bm1 mutation, as all plants in the progeny test with the bm1 inbred expressed the BMR trait, while the bm3 progeny showed all plants to be non-BMR. Leaf tissues were then sampled from the CV5123/GR8207 NIL, 515Dbm1 inbred, as well as heterozygous and null plants from various genetic backgrounds, and subjected to molecular genetic analysis including marker work to determine the exact nature of the DASbm1 bmr mutant.

Corn leaf samples were ground to a fine powder using the Genogrinder 2000 (SPEX CertiPrep, Metuchen, N.J.). DNA was extracted with a standard 2.5% CTAB (cetyl trimethylammonium bromide) DNA extraction protocol. Prior to PCR, DNA samples were quantified with Quant-it PicoGreen Quantification Kit (Invitrogen, Carlsbad, Calif.) according to manufacturer's instructions.

The CAD2 genomic sequence, from maize inbred line, Maize B73, was retrieved from Genbank (Genbank Accession No. AC230031). This sequence was approximately 5.9 kb in length and included a 1.7 kb promoter, four exons, three introns and a short terminator. Primers were designed based on the B73 sequence, and a PCR reaction was performed using the ABI GeneAmp PCR System 9700 (Applied Biosystems, Foster City, Calif.). Reactions contained 2.5 units of TaKaRa LA Taq (Takara Bio Inc., Shiga, Japan), 400 nM of dNTP, 200 nM of forward and reverse primer, and 30 ng of genomic DNA. The following PCR program was used: PCR started with a denaturing step of 2 minutes for 94° C.; followed by 30 cycles of 94° C. for 45 seconds, 55° C. for 45 seconds and 72° C. for 2 minutes. PCR products were visualized on a 2% E-Gel and then extracted using PURELINK™ quick gel extraction kit (Invitrogen, Carlsbad, Calif.). Purified PCR products were then sent to Eurofins MWG Operon (Huntsville, Ala.) for direct sequencing. Sequences were analyzed using Sequencher 4.8 (Ann Arbor, Mich.). Mutations were identified by comparing the CAD2 sequences amplified from bmr mutants and 6XN442 to the sequence listed for Maize B73.

Due to presence of three fairly large introns and some unusual sequence features (for example, an 82 bp TA simple repeat in intron 3), the initial attempts to amplify the CAD2 gene in one 5.9 kb fragment failed. Consequently, a series of nested PCR primers were designed (see Table 1) and used to successfully amplify seven overlapping CAD2 fragments from 515Dbm1 and the wild-type line. FIG. 1. Full-length CAD2 sequences for 515Dbm1 and the wild-type line were assembled from the seven fragments. Genomic, predicted cDNA and protein sequences for 515Dbm1 and 4XN442 are listed as SEQ ID NO: 1-6.

TABLE 1

Primer and length information for the seven overlapping genomic CAD2 PCR fragments.

| Fragment | Forward Primer | Reverse Primer | Fragment Length (bp) |
|---|---|---|---|
| F5-R5 | SEQ ID NO: 9<br>AATGCACGATGTCAACTCTCTTGCCTATAA | SEQ ID NO: 10<br>AATTTTCTCATGAAAACGCTGAAACTGC | 3327 |
| 2933F-2933R | SEQ ID NO: 11<br>TGAGCACAAACGGTTAACACAC | SEQ ID NO: 12<br>ATTGTATCAGTTCACGGTGGTG | 566 |
| 3268F-3268R | SEQ ID NO: 13<br>CACACCAACCACAATAATAAGCTAATACTC | SEQ ID NO: 14<br>AACGATCACCCCGACGCCTACC | 426 |
| 3479F-347 | SEQ ID NO: 15 | SEQ ID NO: 16 | 427 |

TABLE 1-continued

Primer and length information for the seven overlapping genomic CAD2 PCR fragments.

| Fragment | Forward Primer | Reverse Primer | Fragment Length (bp) |
|---|---|---|---|
| 9R | CCACCGTGAACTGATACAATAACAATAAAG | ACACTGCATGCAAGATAACGCTGAAAATAA | |
| 3742F-374 2R | SEQ ID NO: 17 TGCAACAAGAAGATCTGGTCAT | SEQ ID NO: 18 TCATACCGTACTTTCCACATCAA | 500 |
| 3996F-399 6R | SEQ ID NO: 19 TTTTGCGAGAAGTGGACGAGATAAGGT | SEQ ID NO: 20 AATGTTGTTGGAGGTAGGTGGTGTGGTTT | 468 |
| BM11 C1-R14 | SEQ ID NO: 21 GAGAAATGAGGATAACTTTCTCCATCGTT | SEQ ID NO: 22 CTATAGACGAGACAGAAGGGAACGGATTTG | 1364 |

A comparison of 515Dbm1 mutant cad2 with those of wild type (6XN442) and B73 revealed the presence of 15 SNPs and eight insertions/deletions. Most of these changes were located in the promoter region or introns, with the exception of an AC di-nucleotide insertion (nucleotide 3994-3995 in 515Dbm1) located in exon 3 of the bm1 mutant, and a G/A SNP (nucleotide 5410 in 515Dbm1) located in the 4th exon. See FIGS. 3 and 4. The AC insertion in 515Dbm1 creates a frame shift and a premature STOP codon 52-bp downstream of the insertion that resulted in a much shorter CAD2 protein (147 amino acids for 515Dbm1 CAD2, versus 367 amino acids for wild-type CAD2. FIG. 4. The truncated 515Dbm1 CAD2 protein is most likely nonfunctional even if it is produced, because it lacks the NADPH-binding and C-terminal catalytic domains.

The same seven primer pairs shown in Table 1 were used to attempt to amplify overlapping CAD2 fragments from DASbm1, and 6 pairs amplified the expected fragments. However, the F5/R5 pair failed to amply the expected 3327-bp fragment, or even any specific PCR products, even after multiple attempts. Therefore, additional nested PCR primers were designed (see Table 2), and used to successfully amplify the 5' end 2757 bp of the missing 3327-bp fragment. However, the 3' end (approximately 570 bp) were unable to be amplified using many pairs of primers and PCR conditions. With the exception the missing 570-bp gap, the amplified 5346-bp cad2 genomic sequence from DASbm1 is identical to that of B73. This was suspected to be the region that contained molecular changes for bmr phenotype.

Primers encompassing predicted exon 1 and exon 3 were designed (CVF: GTCCGAGAGGAAGGTGGTC (SEQ ID NO:36); and CVR: GGCCGTCCATCAGTGTAGA (SEQ ID NO:37)), and then used to amplify a CAD2 cDNA fragment from DASbm1, 515Dbm1 and 6XN442. As expected, a fragment of 375-bp was amplified from 515Dbm1 and 6XN442. On the other hand, the PCR product from DASbm1 was found to be significantly larger. Sequencing results revealed that cad2 cDNA from DASbm1 contains an extra 409-bp insertion between endogenous exon 1 and exon 2. FIG. 4. A BLAST search against the B73 genome suggested that the 409-bp cDNA insertion in DASbm1 is most likely the result of RNA splicing from part of a putative transposon/repetitive gene (GRMZM2G017736) located on chromosome 1 that contains several introns.

Based on the 409-bp cDNA insertion observed in DASbm1 and its likely genomic source, additional PCR primers were designed (see Table 3), and used to amplify the chimeric genomic region of CAD2 from DASbm1. FIG. 1. Sequencing results reveal that the genomic insertion is 3444-bp in length, and the total genomic cad2 amplified from DASbm1 is 9360 bp. The alignment of genomic CAD2 from DASbm1, B73, 515Dbm1, and 6XN442 is shown in FIG. 3. With the exception of the 3444-bp insertion, the remaining cad2 sequence from DASbm1 is identical to that of B73. The 3444-bp DASbm1 transposon insertion is set forth herein as SEQ ID NO:41.

TABLE 2

Primers for 5' end of a missing DASbm1 genomic CAD2 PCR fragment.

| Fragment | Forward Primer | Reverse Primer | Fragment Length (bp) |
|---|---|---|---|
| F5-149R | SEQ ID NO: 26 AATGCACGATGTCAACTCTCTTGCCTATAA | SEQ ID NO: 27 TGGGTTGAGAAATTGGGTAAGTGC | 837 |
| 547F-547 R | SEQ ID NO: 28 TGCCCGGTCCAATCTTTCTTA | SEQ ID NO: 29 CGTCTTTCGAGGAGGTCTAC | 657 |
| 1022F-102 2R | SEQ ID NO: 30 CGTTTGGTATCGTCCGAGTTGTGT | SEQ ID NO: 31 GCCGGGTAGTGCGATCTTTCTGG | 626 |
| 1501F-150 1R | SEQ ID NO: 32 AGATCATGCTGGAAAGGTAGTAGG | SEQ ID NO: 33 TGATCGAAAATATGCCCCAAGTC | 600 |
| 1955F-195 5R | SEQ ID NO: 34 ACGCGCCTCCTCCAGTAGTTCTCC | SEQ ID NO: 35 CAAGTTCACACGCTGCTGGGTCTG | 763 |

TABLE 3

PCR primers for chimeric genomic region of DASbm1 CAD2.

| Fragment | Forward Primer | Reverse Primer | Fragment Length (bp) |
|---|---|---|---|
| 2687F-2643R | SEQ ID NO: 38 TATGGGTACTGCTCCTGCAC | SEQ ID NO: 39 CCTTGCAGCAGAACCACTG | 2725 |
| 2132F-R5 | SEQ ID NO: 40 AGAATATCATTAGCAGCCAGA | SEQ ID NO: 10 AATTTTCTCATGAAAACGCTGAAACTGC | 1890 |

Genomic Nature of the Insertion in DASbm1.

As shown in FIG. 2, the site of insertion in DASbm1 is located in the endogenous intron 1 of cad2. A closer examination of the 3444-bp insertion sequence revealed that the last 11 bases, with the sequence TACTGATATCT (SEQ ID NO:42) was a direct duplication of an 1'-bp sequence from intron 1 of cad2 located immediately upstream of the insertion. FIG. 2. These direct repeats indicate that the insertion is likely due to DNA transposon activities.

BLAST search results using the 3433-bp insertion (without the 11-bp direct repeat) against B73 genome sequences show numerous homologous hits on different chromosomes, indicating the repetitive nature of the sequence. However, only one hit on chromosome 1 (Maize B73 RefGen_v1, nucleotide positions 148086176-148089850) is 100% identical over the entire length, with the exception of a 242-bp missing gap in the DASbm1 insert. FIG. 4. Other hits are less than 100% identical, and only match part of the insert. Since CAD2 is located on chromosome 5, the insert in DASbm1 is most likely excised from its original location in chromosome 1 and re-inserted into CAD2 via transposon activities. The 242-bp missing gap may reflect the difference between B73 and DASbm1 (CV5123/GR8207) genomes, or it may be due to deletion during the transposition.

A predicted gene (GRMZM2G017736) is located within the 3433-bp insertion sequence and is apparently transcribed in normal corn plants, since quite a few corresponding full-length ESTs (e.g., EU976746 and EU976335) are found in the database. The predicted ORF in GRMZM2G017736 encodes a small protein of 167 amino acids that show high degrees of homology with many hAT (after hobo from *Drosophila*, Ac from maize, and Tam3 from snapdragon) family of transposases that are usually larger proteins. Because the truncated 167 amino acid protein lacks the BED zinc finger DNA binding domain (Pfam02892) normally found in the full-length transposases, the 3433-bp fragment is more likely a Ds element that requires the presence of an Ac element elsewhere for transposition.

Once in the CAD2 locus on chromosome 5, the insertion and cad2 is a chimeric gene. The insertion is spliced into 3 exons of 409-bp and forms a chimeric mRNA with endogenous cad2 exons. FIGS. 2 and 4. The first 1158-bp fragment of the insertion are spliced together with the 5' end 927 bp of the first intron of cad2 as a chimeric intron, the entire predicted ORF of GRMZM2G017736 is spliced as a part of a 1204-bp intron, and the last 463-bp fragment of the insertion is spliced together with the 3' end 231 bp of the first intron of cad2 as a chimeric intron. FIG. 2.

The transposon insertion creates a premature STOP in DASbm1 cad2

As described above, the transposon insertion in DASbm1 creates a chimeric gene that is transcribed as a chimeric mRNA with an extra 409 bp between endogenous cad2 exon1 and exon 2. FIG. 4. This extra 409-bp sequence is predicted to create a frame shift and a premature STOP codon which results in a much shorter CAD2 protein of only 48 amino acids (vs. 367 amino acids for the wild-type protein). FIG. 5. Similar to the truncated CAD2 protein of 515Dbm1, the 48 amino acid DASbm1 CAD2 is most likely nonfunctional even if it is produced, because it lacks the NADPH-binding and C-terminal catalytic domains.

Example 2

CAD2 Allele Specific PCR-Based High-Throughput Assay Design and Validation

A KASPar™ assay was designed based on the AC insertion in exon 3 of 515Dbm1 cad2 to distinguish the mutant allele from the wild-type allele. Thirty-two wild type inbred lines, without the bm1 mutation, as well as segregating populations containing the bm1 mutation, were tested following a protocol obtained from the manufacturer (KBioSciences, Hoddesdon, Hertfordshire, UK).

Figure 8:
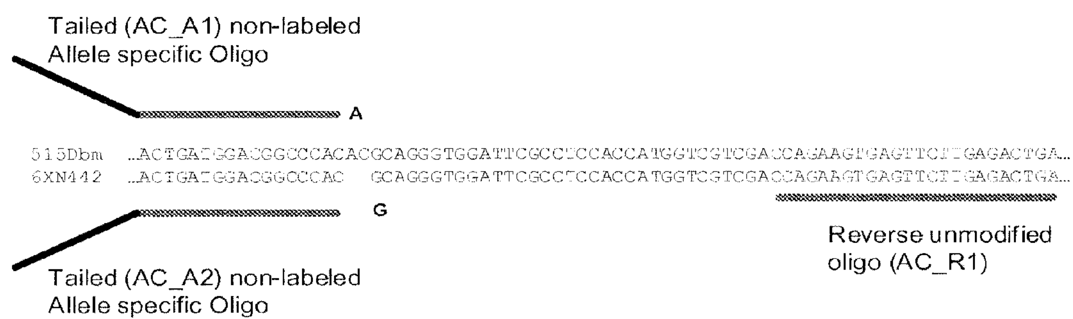
FIG. 8 includes a diagram of a KASPar assay system with primer and template sequences. Template sequences for 515Dbm1 (SEQ ID NO:46) and 6XN442 (SEQ ID NO:47) are shown.

Based on the sequences surrounding the AC insertion, three oligos were designed (SEQ ID NO:43 (AC_R1); TCAGTCTCAAGAACTCACTTCTGG, SEQ ID NO:44 (AC_A1); GAAGGTGACCAAGTTCA TGCTACTGATGGACGGCCCACA and SEQ ID NO:45 (AC_A2); GAAGGTCGGAGTCAACGGATTACTGATGGACGGCCCACG) for a high-throughput KASPar™ marker assay that can be used to differentiate the 515Dbm1 cad2 allele from other bm1 and wild-type CAD2 alleles. FIG. 8.

Figure 9:
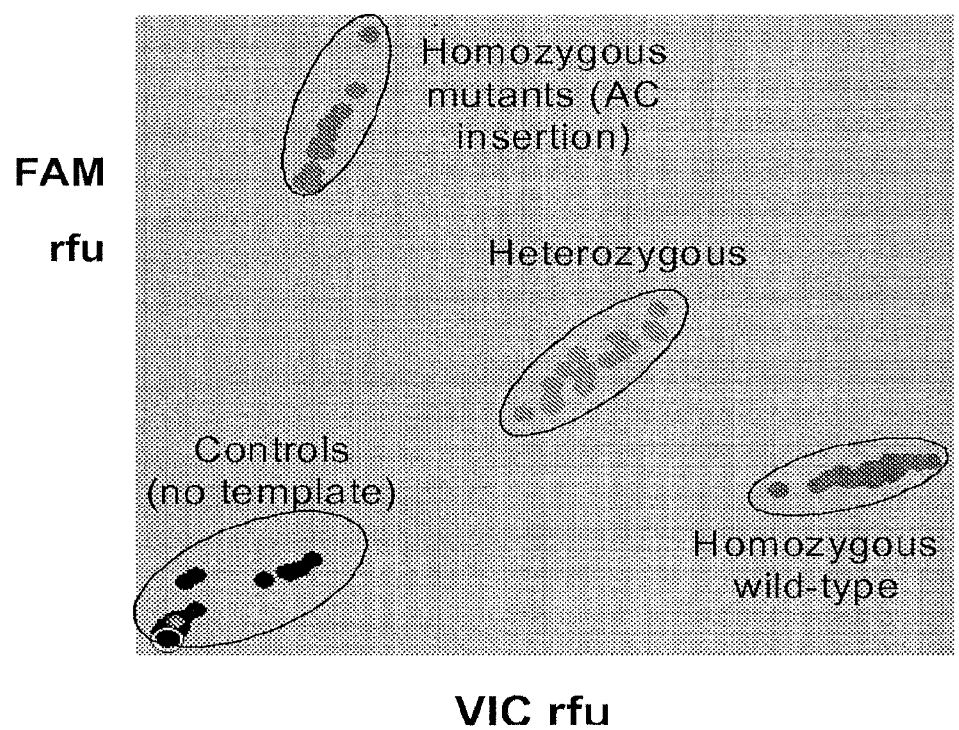
FIG. 9 includes data showing KASPar assay bm1 allele determination. Raw fluorescence intensity data from the plate reader was analyzed using the KBioscience Laboratory Information Management System (KLIMS). A graph showing the RFU of FAM plotted against the RFU from VIC was generated, also using KLIMS. Genotype determination was performed based on the cluster separation as displayed in the cluster view.

The KASPar™ assay was first validated with a panel of 32 wild type inbreds and the bm1 mutant line, 515Dbm1. This analysis indicated that the non-bm1 lines did not contain the AC insertion. The assay was then validated in segregating populations of bm1 maize lines which possessed one of three genotypes: homozygous wild-type; homozygous bm1 (containing the 515Dbm1 AC insertion); and heterozygous. FIG. 9. The KASPar marker detected the bm1 AC insertion within the homozygous bm1 and heterozygous populations. Moreover, this high-throughput assay distinguished the homozygous bm1, heterozygous, and homozygous wild-type populations from one another. As such, markers such as these can be used to rapidly provide an accurate identification of zygosity for the bm1 genotype in plants suspected of containing bm1 from 515Dbm1. The assay can therefore be used for the identification of bm1 germplasm, accelerating introgression of the bm1 trait and molecular breeding using bm1 to improve digestibility of silage or increase ethanol yield.

New TaqMan™ assays were developed to discriminate between all of DASbm1, 515Dbm1, and wild-type CAD2 alleles. Primers and probes that were used for DASbm1 and 515Dbm1 are listed in Table 4 and Table 5, respectively. Because DASbm1 has a large transposon insertion, separate forward primers for DASbm1 (DASbm1_F) and wild-type (Wt CAD2_F) were designed so that appropriate PCR products are amplified under standard TaqMan™ assay conditions. Based on the transposon insertion in DASbm1, AC insertion in 515Dbm1, and wild-type CAD2 sequence, primers and probes for TaqMan™ assays were designed using Primer Express 3.0. Primers and dual-labeled probes with FAM or VIC and Minor Grove Binding Non Fluorescence Quencher™ I (MGBNFQ) dyes were synthesized by Applied Biosystems (Foster City, Calif.). Oligos were dissolved in 1× Tris-EDTA to 100 μM. TaqMan™ genotyping master mix (Applied Biosystems, Foster City, Calif., Catalog #4371355) was used for all PCR reactions. Real time PCR reactions in 25 μl volume were set up using a 96-well plate on an iCycler™ optical system (BioRad, Hercules, Calif.) starting with 15 minutes of denaturing at 95° C. as recommended, followed by 50 cycles of 92° C. for 15 seconds, and 60° C. for 1 minute. Fluorescence signals were recorded at the end of each cycle.

TABLE 4

Primers and probes for TaqMan™ assays to discriminate DASbm1 and wild-type.

| Oligonucleotide | Sequence |
|---|---|
| DASbm1_probe | 6FAM-AGGCTTACTGATATCTG (SEQ ID NO: 48)-MGBNFQ |
| Wt CAD2_probe | VIC-CTGCAGATATCAGTAGTTACG (SEQ ID NO: 49)-MGBNFQ |
| DASbm1_F | GCCGGATTGTGACCCATTAT (SEQ ID NO: 50) |
| DASbm1_R | CGCGACAGGCGGTAGGTA (SEQ ID NO: 51) |
| Wt CAD2_F | GCAGCGTGTGAACTTGTAGGTAA (SEQ ID NO: 55) |

TABLE 5

Primers and probes for TaqMan™ assays to discriminate 515Dbm1 and wild-type.

| Oligonucleotide | Sequence |
|---|---|
| 515Dbm1_probe | 6FAM-ACGGCCCACACGC (SEQ ID NO: 53)-MGBNFQ |
| Wt CAD2_probe | VIC-ACGGCCCACGCAGG (SEQ ID NO: 54)-MGBNFQ |
| bm1_F | GGTCATACAACGACGTCTACACTGA (SEQ ID NO: 55) |
| bm1_R | ATGGTGGAGGCGAATCCA (SEQ ID NO: 56) |

Figure 10:
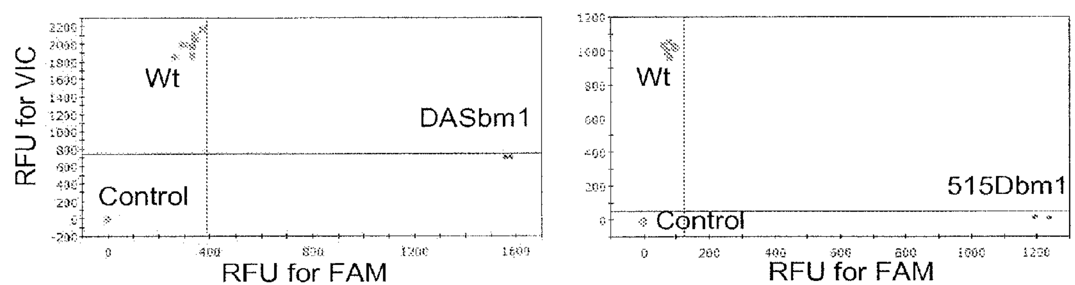
FIG. 10 includes data showing TaqMan CAD2 allele determination. Allelic discrimination was calculated using iCycler optical system software with relative fluorescence units (RFU) of VIC displayed on the y-axis and RFU of FAM displayed on the x-axis.

Results of allelic discrimination assays using the primers set forth in Tables 4 and 5 are shown in FIG. 10. Because these assays and KASPar™ markers are based directly on bm1 mutations in cad2, they will provide more accurate genotyping than available indirect bm1 markers.

Example 3

Characteristics of bm1 Maize with Truncating CAD2 Mutations

Because DASbm1 represents a novel bm1 mutation, nothing is known about DASbm1, except that is has a bmr phenotype. The RNA expression levels and lignin contents in DASbm1 plants were investigated, and then compared to those of 515Dbm1 and wild-type (6XN442) plants. It was expected that 515Dbm1 and DASbm1 plants have significantly reduced CAD activities due to the mutations in the cad2 genes of these two maize lines, and the consequent premature termination of CAD2. In addition, 515Dbm1 and DASbm1 plants were hypothesized to have reduced cad2 transcript abundance.

DASbm1, 515Dbm1, and 6XN442 plants were grown in a greenhouse. Leaf tissues were harvested from four-week-old plants and midrib tissues were separated. Samples were grounded to fine powder in liquid nitrogen and extracted with Qiagen's RNeasy™ plant mini kit. SuperScript™ III One-Step RT-PCR kit from Invitrogen and BioRad's iCycler™ were used for quantitative RT-PCR to determine RNA expression levels. CAD2-specific oligos were designed based on the fourth exon of CAD2, and corn invertase was used as a control for the Delta-Delta CT calculation.

To compare the CAD2 RNA expression levels, the following primers/probes based on the fourth exon of CAD2 and corn invertase were designed for quantitative RT-PCR. Table 6.

TABLE 6

Primers and probes for CAD2 qRT-PCR.

| Oligonucleotide | Sequence |
|---|---|
| CAD2_F | CCACATGGGCGTGAAGGTA (SEQ ID NO: 57) |
| CAD2_R | TTCTTGGACGACGAGCTGATC (SEQ ID NO: 58) |
| CAD2_Eprobe | 6FAM-ATGGGCCACCACGTGA (SEQ ID NO: 59)-MGBNFQ |
| INV59F | ATGGTGGAGGCGAATCCA (SEQ ID NO: 60) |
| INV59R | TGCCGTCCGTGCCCT (SEQ ID NO: 61) |
| INV_probe | VIC-CCGTGTACTTCTACCTGC (SEQ ID NO: 62)-MGBNFQ |

Figure 6:
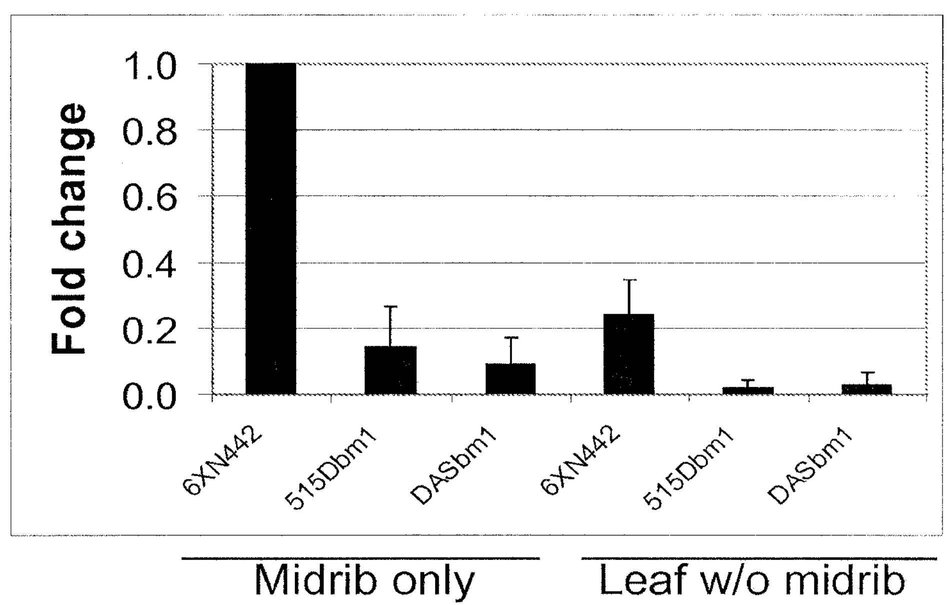
FIG. 6 includes data showing the relative expression levels of CAD2 RNA in wild-type, 515Dbm1, and DASbm1 corn midribs and leaves. Data is normalized to the RNA level in the midrib of wild-type corn 6XN442. Data represent the mean value of 3 plants, and error bars indicate standard deviation.

As shown in FIG. 6, midribs have much higher level of CAD2 expression than the rest of the leaf tissues without midribs regardless of genotypes The differences are 4.1, 8.0, and 3.4 fold for 6XN442, 515Dbm1, and DASbm1, respectively. Both DASbm1 and 515Dbm1 lines have significantly less cad2 expression, with an average reduction of 91% in the midrib, and 89% in the leaf, for DASbm1; and 87% in the midrib, and 93% in the leaf for 515Dbm1, when compared with wt 6XN442. However, there is no significant difference between the two bm1 mutants. FIG. 6. These results are consistent with what have been reported in the literature for maize bm1 (Halpin et al. (1998), supra), as well as sorghum mutant, bmr6 (Saballos et al. (2009), supra). The reduction in RNA expression is mostly likely due to RNA degradation mediated by nonsense mutations that create premature CAD2 proteins in the 515Dbm1 and DASbm1 mutants, a mechanism previously observed in plants and other species. Conti and Izaurralde (2005) Curr Opin Cell Biol. 17:316-25.

To compare the relative lignin contents of mutant and wild-type plants, ground leaves and internodes were subjected to FTIR spectroscopy analysis.

Fourier Transform Infrared measurements were carried out using Bruker Vertex spectrometer (Bruker Optics Inc, 19 Fortune Drive, Maiming Park, Billerica Mass. 01821), with an Attenuated Total Reflectance (ATR) Miracle sampling accessory with diamond crystal (Pike Technologies, Madison, Wis.). The spectrometer is equipped with a deuterated triglycine sulfate (DTGS) detector, operating at 4 $cm^{-1}$ resolution and 0.32 cm/s mirror velocity. Two hundred and fifty-six interferograms were co-added before Fourier transformation. The instrument was allowed to purge for 5 min. with nitrogen gas (grade 1) prior to acquisition of the spectra to minimize the spectral contribution due to atmospheric carbon dioxide and water vapor. The ATR Miracle cell sampling accessory has a single-bounce diamond designed for use in the FTIR spectrometer. The depth of penetration of the infrared beam is 1.46 microns. A major advantage of this accessory is that it requires smaller sample volumes compared to the multiple-bounce HATR accessory.

Leaves (7th and 8th, 9th and 10th) and internodes (1st and 2nd, 7th and 8th, 9th and 10th) were collected from greenhouse grown corn plants just after silking, lyophilized, and ground into fine powders. A small portion of the samples were placed directly on the diamond crystal of ATR for the data acquisition. Spectra were collected in finger print region from 800-1800 $cm^{-1}$. Single-beam spectra of all the samples were obtained, and spectral data are presented as the ratio of the background spectrum of air in absorbance units. After every measurement, ATR crystal was thoroughly cleaned and dried, and its spectrum was examined to ensure that sample residues from the previous acquisition were not retained on the crystal surface. All the spectra were baseline corrected and area normalized to eliminate any spectral artifacts.

Figure 7:
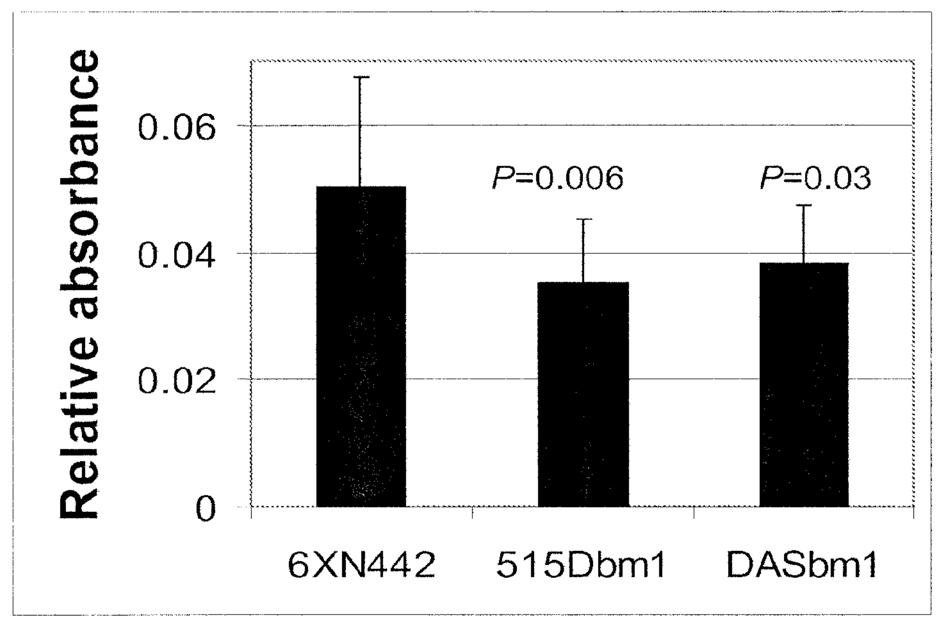
FIG. 7 includes data showing the relative amounts of total lignin in wild-type, 515Dbm1, and DASbm1 corn. Data represent the mean value of 3 plants, with five samples per plant obtained from both leaves and internodes. Error bars indicate standard deviation, and P values were generated by student's T test.

The lignin contents in the samples are directly proportional to FTIR relative absorbance. As expected, the reduction in CAD2 RNA expression in both mutants results in significant reduced lignin contents. FIG. 7. On average, the total lignin content reduction was approximately 24% in DASbm1 (P=0.03) and 30% in 515Dbm1 (P=0.006) when compared to wild-type 6XN442. There was no significant difference between the two bm1 mutants (P=0.4).

bm1 mutations in maize exhibit a reddish brown pigmentation of the leaf midrib associated with significantly reduced lignin content and altered lignin composition. This phenotype is visible from V6 through later stages in newly-developed leaves and other tissues. The molecular bases of two independent bm1 mutants (DASbm1 and 515Dbm1) were identified. Based on the specific mutations, high throughput PCR assays for detecting different alleles were developed. The foregoing results demonstrate that ZmCAD2 is the underlying gene for the bm1 mutation in 515Dbm1 and DASbm1, and provide a molecular basis for the observed phenotype. Because bmr mutations are common among many monocot species, the above-described mutations and markers can also be used in other crops; for example, sorghum, sugarcane, millet, rice, and bioenergy species such as switchgrass.

Example 4

Brown Midrib1 (bm1) as a Visual Selectable Marker for Transgenes

EXZACT Precision Technology is a zinc-finger engineering technology that has been shown to precisely target any DNA sequence and accurately modify the genome through gene disruption, editing or gene addition. Based upon EXZACT Precision Technology and recent bm1 discoveries, two alternative approaches can be implemented to create a visual selectable marker to differentiate transgenic plants from their null segregants. A visual marker will enable breeders and scientists in the field to quickly identify transgenic individuals in a segregating population (T1 for example) and compare them to the nulls without detail molecular work and speed up transgenic pipeline screening process. High throughput assays are also available and can be used to confirm the visual observation if needed.

In the first representative approach, mutant bm1 maize (DASbm1 or 515Dbm1) can be used as the target germplasm for transformation. Through molecular breeding, bm1 mutation can be introduced into current transformation germplasm (B104) using CAD2-based markers. A Wt CAD2 and a gene of interest (GOI) in the same construct are targeted to the endogenous mutant cad2 locus by EXZACT Precision Technology. Because bm1 mutation is recessive, plants homozygous for GOI-WtCAD2 or heterozygous have normal pigmentation whereas null segregants have brown midrib phenotype. This also works without EXZACT Precision Technology, but transgene insertion site in the genome is random. An alternative embodiment includes engineering of one or more zinc finger protein(s) that deletes the transposon insertion in DASbm1 or the AC insertion in 515Dbm1 in the endogenous mutant cad2 locus and at the same time inserts the GOI into a nearby locus (to prevent significant segregation of GOI and bm1 marker). This eliminates the need for a Wt CAD2 in the transgenic construct.

In a second representative approach, Wt plants are used as the target germplasm for transformation. The GOI can be targeted to the endogenous Wt CAD2 locus using EXZACT Precision Technology. Site of insertion can be the same as the transposon insertion in DASbm1, AC insertion in 515Dbm1 or any position within the CAD2 locus that renders the protein nonfunctional (functional domains of CAD2 well known). In this case, plants homozygous for transgene have brown midrib phenotype whereas heterozygotes and nulls have normal pigmentation. Brown midrib and associated phenotypes are beneficial and EXZACT Precision Technology can be used to target BM1 (CAD2) and/or BM3 (Caffeic Acid O-Methyltransferase) loci.

What may be claimed is:

1. A method for creating a genetically modified plant comprising a gene of interest, the method comprising:

providing a nucleic acid molecule comprising a wild-type CAD2 gene and the gene of interest;

introducing the nucleic acid molecule into a bm1 plant;

screening the plant or its progeny for normal pigmentation; and selecting a plant having normal pigmentation, wherein the plant comprises the gene of interest.

2. The method of claim 1, wherein a zinc finger nuclease is utilized to integrate the nucleic acid molecule into the genome of the bm1 plant at the CAD2 locus.

3. A method for creating a genetically modified plant comprising a gene of interest, the method comprising:

providing a nucleic acid molecule comprising a gene of interest;

introducing the nucleic acid molecule into a plant homozygous for the wild-type CAD2 allele;

utilizing a zinc finger nuclease to integrate the nucleic acid molecule into the genome of the plant, such that the CAD2 gene is inactivated;

screening the plant or its progeny for a brown midrib phenotype; and selecting a plant having a brown midrib phenotype, wherein the selected plant comprises the gene of interest.

* * * * *

SEQUENCE LISTING

```
<160> NUMBER OF SEQ ID NOS: 65

<210> SEQ ID NO 1
<211> LENGTH: 5924
<212> TYPE: DNA
<213> ORGANISM: Zea mays

<400> SEQUENCE: 1

aatgcacgat gtcaactctc ttgcctataa ttatgttcaa actctcgtca ataatagtag     60

ctagtgctgt tattgtaaag tatcgctaaa atatgcatat atacttataa cttatccatg    120
```

```
ttaaagaaaa tcgaatatgc tagcaaagac atatgggccc gttgaggaga gctacgttac     180
atttgatttc taggagaaag cagagtgaag agctggtgaa aatcgattct ctattatctt     240
cactagaata taaatgaagc acatttttag ctccagctct tagtgcaaat agagaaactc     300
tcctaattgt agcatgaatg agatgacatt ataaaagcct ttgatgagat tttcttccga     360
gaagctgaag ctcctcagat agcccaatga tatgtatgta agtgtatttt tttttaaaaa     420
aagcgggcaa atgaaactaa atcatcctat cccctttaat atactgagat gccaattagt     480
tggttgccag ccggagtatg gtggatggga tcctcctatt ggttaaatta tgaatgaatt     540
gtttggttgc ccggtccaat ctttcttatg tctgtttcgt ttagatcgtg tacaccactt     600
cttattgttt aaatggccaa tttaatcggg gcctaaacga catatgtgcc tcaatttacc     660
ataccaatga tgccgcttac gtgaatagtt gaataccgat actactacta ccgcacgcgt     720
catggtttaa cctttcaaca gttggattga aacatcagcg gccactcggc acttgggtga     780
caatttgtca cacacctcgt agtcgagtgg aaatgcactt acccaatttc tcaacccata     840
agactatttc cagcatctcg attaatcccc atatttaaaa tcaactttca tagtttatat     900
tgtgaagtgt tttatgtgac gacattagtg gatttatgga cacggtctaa ggacccgtga     960
cttgtatttt tcttcattga cctagctagc tagctagcta gcatcgtgaa gccacgccca    1020
tgcgtttggt atcgtccgag ttgtgtacaa tttccagcca gtggaatcac agttattgga    1080
tcattttggt acgtataacg tattcttttt gtatttcctg tctaaagaca ttaatttcag    1140
agaagccggg tctattttag aagggcttgg cttcttcccg tttggtagac ctcctcgaaa    1200
gacgaaagtc ttacttcctc tggtttccta ttagttatcg ttttgaataa agttcgagtc    1260
aaacttataa aattttgact acaaataact attttgttat ttagttttgg aacctaatat    1320
ttatatgcac caatttgtta taaaaagtac ttttataaaa gtataaatgt attaagagtt    1380
catttgtatt ttaacaaaaa atattggtta aagttatatt ttggagaccg tgtcgttgtc    1440
ctaaacgaca actaatagga aaccggaggg agtactgatt ttctcctgca gcgggcacag    1500
aagatcatgc tggaaaggta gtaggtacag gtagcctgga gcggaggagt tgccactttg    1560
cacagtgccg atcgagctcg cagccactat atagcacgca ccctgctcaa gcatcttttc    1620
cttacccaga aagatcgcac tacccggcgc tcgcgcggct ttctttccca actccgacga    1680
aggctagcta caccacctgg tgcgggctcg tctccatcgc ccgccacccg ctccgtcgtc    1740
gtcgtccccg ccgcgccgat cccgaatcga atggggagcc tggcgtccga gaggaaggtg    1800
gtcgggtggg ccgccaggga cgccaccgga cacctctccc cctactccta caccctcagg    1860
tactacgccg cgccggcgcc ctcgtgtttg tcctctcctc cagtccctcc cgtctgtata    1920
tgtccgactg tctccgccct tttgcaaaca cgcaaatgga tggatccagg aggacgagag    1980
acggttagtt tctgcacgcg cctcctccag tagttctccg agttctcggg aagaacagaa    2040
aatttgattg atgttttttt tgatgaaaaa taaaaaggga cttggggcat attttcgatc    2100
aacttgcaac ggaagatgac taggagtacg tacgtagcgt agcggcggcg ggttttaatt    2160
tgggggagca ctctgttagt ctgttgcata tatgggagta cctgattcgt tgcagttatt    2220
attatctata cgcgtacgat atgttttagg gggtgtttgg ttgctcctgt taaagtttag    2280
tccgggtcac atcaagcgtt ttacttttaa ataggagtat gaaatataga cccaaccaac    2340
tagactagat tcgtctcgtc ttttaatctt cggctgacaa attagtttta taatccgact    2400
acatttaata cccggaacag aggttcaaac attcgatggg acagagacta aattttagca    2460
```

-continued

```
gggtgtaacc aaacaccccc ttagtccaca acaagagcat tatgcgctgt gttgcatcat   2520
gcatatatga tacgtcttca acttcttgcg gtccaactct agatagtgca catgcatatg   2580
ccaaatacgg atactggaca agatagcaca caagcagagc aggttgggcg agcgtacact   2640
gcacgtatgc ttctcttcta catggcattt tgtttcgaac attaatatat gggtactgct   2700
cctgcacagc actgcacgtg cttgacgtct cgtacagacc cagcagcgtg tgaacttgta   2760
ggtaagatac gtaactactg atatctgcag ctacctaccg cctgtcgcga tcaccatcca   2820
tttgtactcg cagtaataat accgattacc cttttattat tatttctcat gccatcgacg   2880
actactagca ctatccaacg tacaactgtg gcgcgattca tatatgcata attctacatg   2940
gtgctagtct tcggcaagaa aaaaaactaa cacttgtctc tttttcatat gggatgtgtt   3000
gtggtggtga caacaggaac acaggccctg aagatgtggt ggtgaaggtg ctctactgcg   3060
ggatctgcca cacggacatc caccaggcca agaaccacct cggggcttca aagtatccta   3120
tggtccctgg gtgagcacaa acggttaaca cacacacgca cccagcgatt tttcaggacc   3180
cttggggatc cagtatatat atatatgctc cgtgtacggt ccagaatata cgtactgaat   3240
ttccaagtgt cctattattc aatttgtctc aaaactataa aggatatata tagtgacatg   3300
cagtttcagc gttttcatga gaaaattaca catgcagaca aattcaggta taattatttg   3360
attcatgacg accagcatat agattggtag atagagtgca catttgtcaa ccacaaacgt   3420
tagcatccca gtccggagct atcccctggg ttacaggtgg caaatacaca ccaaccacaa   3480
taataagcta atactcttac gtctgtagtt ggttgccaat tactgatcag attacttgaa   3540
tcacaagagc ttgttgtgtc taatttgtac aggctattta tatcatgata gctaaagagc   3600
tgctgaaatg agtagcaagg aaacctcacc ggccgtccta tacttttctc tgacatgacg   3660
acaggacaac cactccacca ccgtgaactg atacaataac aataaagtcc tttagtccaa   3720
gtaaattaga ataggctaga aactaaaatc caacagagag acgaaatcat ggctttggtt   3780
tggtaataac tgatactgtc gcaggcacga ggtggtcggc gaggtggtgg aggtcgggcc   3840
cgaggtggcc aagtacggcg tcggcgacgt ggtaggcgtc ggggtgatcg ttgggtgctg   3900
ccgcgagtgc agcccctgca aggccaacgt tgagcagtac tgcaacaaga agatctggtc   3960
atacaacgac gtctacactg atggacggcc cacacgcagg gtggattcgc ctccaccatg   4020
gtcgtcgacc agaagtgagt tcttgagact gaaaactaat cttttcactg gtttaattat   4080
tttcagcgtt atcttgcatg cagtgttgta gagataataa tctctttttt tattaaaaaa   4140
atgtttggtc tgaaaaaagc tagaaatata tagttgaact tcaattatat ttcaactttt   4200
gcgagaagtg gacgagataa ggtccaatcc ttctagaaaa ggtgcaggaa agtatatata   4260
tatatatata tatatatata tatatatata tatatatata tatatatata tatatatata   4320
tatatatata tatatgggta tggggataaa atatgatcga gaaagtccat catcatctag   4380
ctgcaagtcg ttgtatggat gtcttatggt gaccaggcaa gagtgttgat gtggaaagta   4440
cggtatgatt tggtgtgctt tacttgcttg actttgtgag gttgaaccac caccacagaa   4500
gccgaatcct cacctactct tgattgaaga ttggccaccc aaaccatcac cggttgttgg   4560
gagaaatgag gataactttc tccatcgttc gctccaaaac ctgtctacac tttagtgtac   4620
tgtctttttc agtcagtgcg caaaccacac cacctacctc caacaacatt ttgagatagc   4680
gatttctttt ttcttttttt aaaggcactc cgtgtgtgaa ttatgataga acagtaactt   4740
ttcaagcaat tttctttgct gccagtcaat tttggaagaa aaaaaaaggc aacctcggta   4800
acacgaattt aggttcctat tttgttcttg gtaaaaaaaa actaaatacc tagttccacg   4860
```

```
taagttgata gttaatgcat tttgtttcag gtttgtggtg aagatcccgg cgggtctggc   4920

tccggagcaa gcggcgccgc tgctgtgcgc tggcgtgacg gtgtacagcc cgctgaagca   4980

ctttgggctg acgaccccgg gcctccgtgg cggcatcctg ggcctcggcg gcgtgggcca   5040

catgggcgtg aaggtagcca aggccatggg ccaccacgtg acggtgatca gctcgtcgtc   5100

caagaagcgc gcggaggcaa tggaccacct cggcgcggac gcgtacctag tgagctcgga   5160

cgccgcggcc atggcggcgg ccgccgactc gctggactac atcatcgaca cggtgcccgt   5220

gcaccacccg ctggagccgt acctggcgct gctgaagctg gacggcaagc tcgtgctgct   5280

gggcgtcatc ggcgagcccc tgagcttcgt gtcgcccatg gtgatgctgg ggcggaaggc   5340

catcacgggg agcttcatcg gcagcatcga cgagaccgct gaggtgcttc agttctgcgt   5400

cgacaagggg ctcacctccc agatcgaggt ggtcaagatg gggtacgtga acgaggcgct   5460

ggagcggctg gagcgcaacg acgtccgcta ccgcttcgtc gtcgacgtcg ccggtagcaa   5520

cgtcgaggcg gaggcggcgg cggcggatgc ggccagcaac tgatggcacc gcgtcgtcga   5580

gtcgaaccac gtctgtgcgc cgcgtgcaac gttcgttcgg gtcgagtctg cgtgcaacgt   5640

tctgcttcct ttactagttg ttgtctttcc gccttcttgc cgttctgttc tgggctttga   5700

gatgagacga tggatggtca gtttttaatg tcagactgaa taactacgta tagtactgta   5760

gtattactcg gagtacgcca gaatgtggtg tggtgtcagt ctcaccagca atctggattt   5820

gccaagtgtt tctatttttt cttcggtttg cccgagtgtt tgtgattgtt aagaactacg   5880

ttattacgga tcgtcaaatc cgttcccttc tgtctcgtct atag                      5924
```

<210> SEQ ID NO 2
<211> LENGTH: 1512
<212> TYPE: DNA
<213> ORGANISM: Artificial
<220> FEATURE:
<223> OTHER INFORMATION: Predicted 515Dbm1 CAD2 cDNA sequence

<400> SEQUENCE: 2

```
gtgcgggctc gtctccatcg cccgccaccc gctccgtcgt cgtcgtcccc gccgcgccga     60

tcccgaatcg aatggggagc ctggcgtccg agaggaaggt ggtcgggtgg gccgccaggg    120

acgccaccgg acacctctcc ccctactcct acaccctcag gaacacaggc cctgaagatg    180

tggtggtgaa ggtgctctac tgcgggatct gccacacgga catccaccag gccaagaacc    240

acctcggggc ttcaaagtat cctatggtcc ctgggcacga ggtggtcggc gaggtggtgg    300

aggtcgggcc cgaggtggcc aagtacggcg tcggcgacgt ggtaggcgtc ggggtgatcg    360

ttgggtgctg ccgcgagtgc agcccctgca aggccaacgt tgagcagtac tgcaacaaga    420

agatctggtc atacaacgac gtctacactg atggacggcc cacacgcagg gtggattcgc    480

ctccaccatg gtcgtcgacc agaagtttgt ggtgaagatc ccggcgggtc tggctccgga    540

gcaagcggcg ccgctgctgt gcgctggcgt gacggtgtac agcccgctga agcactttgg    600

gctgacgacc ccgggcctcc gtggcggcat cctgggcctc ggcggcgtgg gccacatggg    660

cgtgaaggta gccaaggcca tgggccacca cgtgacggtg atcagctcgt cgtccaagaa    720

gcgcgcggag gcaatggacc acctcggcgc ggacgcgtac ctagtgagct cggacgccgc    780

ggccatggcg gcggccgccg actcgctgga ctacatcatc gacacggtgc ccgtgcacca    840

cccgctggag ccgtacctgg cgctgctgaa gctggacggc aagctcgtgc tgctgggcgt    900

catcggcgag cccctgagct tcgtgtcgcc catggtgatg ctggggcgga aggccatcac    960
```

```
ggggagcttc atcggcagca tcgacgagac cgctgaggtg cttcagttct gcgtcgacaa   1020

ggggctcacc tcccagatcg aggtggtcaa gatggggtac gtgaacgagg cgctggagcg   1080

gctggagcgc aacgacgtcc gctaccgctt cgtcgtcgac gtcgccggta gcaacgtcga   1140

ggcggaggcg gcggcggcgg atgcggccag caactgatgg caccgcgtcg tcgagtcgaa   1200

ccacgtctgt gcgccgcgtg caacgttcgt tcgggtcgag tctgcgtgca acgttctgct   1260

tcctttacta gttgttgtct ttccgccttc ttgccgttct gttctgggct ttgagatgag   1320

acgatggatg gtcagttttt aatgtcagac tgaataacta cgtatagtac tgtagtatta   1380

ctcggagtac gccagaatgt ggtgtggtgt cagtctcacc agcaatctgg atttgccaag   1440

tgtttctatt ttttcttcgg tttgcccgag tgtttgtgat tgttaagaac tacgttatta   1500

cggatcgtca aa                                                       1512
```

```
<210> SEQ ID NO 3
<211> LENGTH: 147
<212> TYPE: PRT
<213> ORGANISM: Artificial
<220> FEATURE:
<223> OTHER INFORMATION: Predicted amino acid sequence of 515Dbm1 CAD2

<400> SEQUENCE: 3

Met Gly Ser Leu Ala Ser Glu Arg Lys Val Val Gly Trp Ala Ala Arg
1               5                   10                  15

Asp Ala Thr Gly His Leu Ser Pro Tyr Ser Tyr Thr Leu Arg Asn Thr
            20                  25                  30

Gly Pro Glu Asp Val Val Val Lys Val Leu Tyr Cys Gly Ile Cys His
        35                  40                  45

Thr Asp Ile His Gln Ala Lys Asn His Leu Gly Ala Ser Lys Tyr Pro
    50                  55                  60

Met Val Pro Gly His Glu Val Val Gly Glu Val Val Glu Val Gly Pro
65                  70                  75                  80

Glu Val Ala Lys Tyr Gly Val Gly Asp Val Val Gly Val Gly Val Ile
                85                  90                  95

Val Gly Cys Cys Arg Glu Cys Ser Pro Cys Lys Ala Asn Val Glu Gln
            100                 105                 110

Tyr Cys Asn Lys Lys Ile Trp Ser Tyr Asn Asp Val Tyr Thr Asp Gly
        115                 120                 125

Arg Pro Thr Arg Arg Val Asp Ser Pro Pro Pro Trp Ser Ser Thr Arg
    130                 135                 140

Ser Leu Trp
145
```

```
<210> SEQ ID NO 4
<211> LENGTH: 5898
<212> TYPE: DNA
<213> ORGANISM: Zea mays

<400> SEQUENCE: 4

aatgcacgat gtcaactctc ttgcctataa ttatgttcaa actctcgtca ataatagtag     60

ctagtactgt tattgtaaag tatcgctaaa atatgcatat atacttataa cttatccatg    120

ttaaagaaaa tcgaatatgc tagcaaagac atatgggccc gttgaggaga gctacgttac    180

atttgatttc taggagaaag cagagtgaag agctggtgaa aatcgattct ctattatctt    240

cactagaata taaatgaagc acatttttag ctccagctct tagtgcaaat agagaaactc    300

tcctaattgt agcatgaatg agatgacatt ataaaagcct ttgatgagat tttcttccga    360
```

```
gaagctgaag ctcctcagat agcccaatga tatgtatgta agtgtatttt ttttaaaaaa    420
agcgggcaaa tgaaactaaa tcgtcctatc ccctttaata tactgagatg ccaattagtt    480
ggttgccagc cggagtatgg tggatgggat cctcctattg gttaaattat gaatgaattg    540
tttggttgcc cggtccaatc tttcttatgt ctgtttcgtt tagatcgtgt acaccacttc    600
ttattgttta aatggccaat ttaatcgggg cctaaacgac atatgtgcct caatttacca    660
taccaatgat gccgcttacg tgaatagttg aataccgata ctactactac cgcacgcgtc    720
atggtttaac cttttaacag ttggattgaa acatcagcga ccactcggca cttgggtgac    780
aatttgtcac acacctcgta gtcgagtgga aatgcactta cccaatttct caacccataa    840
gactatttcc agcatctcga ttaatcccca tatttaaaat caactttcat agtttatatt    900
gtgaagtgtt ttatgtgacg acattagtgg atttatggac acggtctaag gacccgtgac    960
ttgtattttt cttcattgac ctagctagct agctagctag catcgtgaag ccacgcccat   1020
gcgtttggta tcgtccgagt tgtgtacaat ttccagccag tggaatcaca gttattggat   1080
cattttggta cgtataacgt attctttttg tatttcctgt ctaaagacat taatttcaga   1140
gaagccgggt ctattttaga agggcttggc ttcttcccgt ttggtagacc tcctcgaaag   1200
acgaaagtct tacttcctct ggtttcctat tagttatcgt tttgaataaa gttcgagtca   1260
aacttataaa attttgacta caaataacta ttttgttatt tagttttgga acctaatatt   1320
tatatgcacc aatttgttat aaaaagtact tttataaaag tataaatgta ttaagagttc   1380
atttgtattt taacaaaaaa tattggtcaa agttatattt tggagaccgt gtcgttgtcc   1440
taaacgacaa ctaataggaa accggaggga gtactgattt tctcctgcag cgggcacaga   1500
agatcatgct ggaaaggtag taggtacagg tagcctggag cggaggagtt gccactttgc   1560
acagtgccga tcgagctcgc agcccctata tagcacgcac cctgctcaag catcttttcc   1620
ttaccctata tagctcgcgc ggctttcttt cccaactccg acgaaggcta gctacaccac   1680
ctggtgcggg ctcgtctcca tcgcccgcca cccgctccgt cgtcgtcgtc cccgccgcgc   1740
cgatcccgaa tcgaatgggg agcctggcgt ccgagaggaa ggtggtcggg tgggccgcca   1800
gggacgccac cggacacctc tccccctact cctacaccct caggtactac gccgcgccgg   1860
cgccctcgtg tttgtcctct cctccagtcc ctcccgtctg tatatgtccg actgtctccg   1920
cccttttgca aacacgcaaa tggatggatc caggaggacg agagacggtt agtttctgca   1980
cgcgcctcct ccagtagttc tccgagttct cgggaagaac agaaaatttg attgatgttt   2040
tttttgatga aaaataaaaa gggacttggg gcatattttc gatcaacttg caacggaaga   2100
tgactaggag tacgtacgta gcgtagcggc ggcgggtttt aatttggggg agcactctgt   2160
tagtctgttg catatatggg agtacctgat tcgttgcagt tattattatc tatacgcgta   2220
cgatatgttt taggggtgtt tggttgctcc tgctaaagtt tagtccgggt cacatcaagc   2280
gttttacttt taaataggag tatgaaatat agacccaacc aactagacta gattcgtctc   2340
gtcttttaat cttcggctga caaattagtt ttataatccg actacattta atacccggaa   2400
cagaggttca aacattcgat gggacagaga ctaaatttta gcagggtgta accaaacacc   2460
cccttagtcc acaacaagag cattatgcgc tgtgttgcat catgcatata tgatacgtct   2520
tcaacttctt gcggtccaac tctagatagt gcacatgcat atgccaaata cggatactgg   2580
acaagatagc acacaagcag agcaggttgg gcgagcgtac actgcacgta tgcttctctt   2640
ctacatggca ttttgtttcg aacattaata tatgggtact gctcctgcac agcactgcac   2700
```

-continued

```
gtgcttgacg tctcgtacag acccagcagc gtgtgaactt gtaggtaaga tacgtaacta   2760
ctgatatctg cagctaccta ccgcctgtcg cgatcaccat ccatttgtac tcgcagtaat   2820
aataccgatt accctttat tattatttct catgccatcg acgactacta gcactatcca   2880
acgtacaact gtggcgcgat tcatatatgc ataattctac atggtgctag tcttcggcaa   2940
gaaaaaaaac taacacttgt ctctttttca tatgggatgt gttgtggtgg tgacaacagg   3000
aacacaggcc ctgaagatgt ggtggtgaag gtgctctact gcgggatctg ccacacggac   3060
atccaccagg ccaagaacca cctcggggct tcaaagtatc ctatggtccc tgggtgagca   3120
caaacggtta acacacacac gcacccagcg atttttcagg acccttgggg atccagtata   3180
tatatatgct ccgtgtacgg tccagaatat acgtactgaa tttccaagtg tcctattatt   3240
caatttgtct caaaactata aaggatatat atagtgacat gcagtttcag cgttttcatg   3300
agaaaattac acatgcagac aaattcaggt ataattattt gattcatgac gaccagcata   3360
tagattggta gatagagtgc acatttgtca accacaaacg ttagcatccc agtccggagc   3420
tatcccctgg gttacaggtg gcaaatacac accaaccaca ataataagct aatactctta   3480
cgtctgtagt tggttgccaa ttactgatca gattacttga atcacaagag cttgttgtgt   3540
ctaatttgta caggctattt atatcatgat agctaaagag ctgctgaaat gagtagcaag   3600
gaaacctcac cggccgtcct atacttttct ctgacatgac gacaggacaa ccactccacc   3660
accgtgaact gatacaataa caataaagtc ctttagtcca agtaaattag aataggctag   3720
aaactaaaat ccaacagaga gacgaaatca tggctttggt ttggtaataa ctgatactgt   3780
cgcaggcacg aggtggtcgg cgaggtggtg gaggtcgggc ccgaggtggc caagtacggc   3840
gtcggcgacg tggtaggcgt cggggtgatc gttgggtgct gccgcgagtg cagcccctgc   3900
aaggccaacg ttgagcagta ctgcaacaag aagatctggt catacaacga cgtctacact   3960
gatggacggc ccacgcaggg tggattcgcc tccaccatgg tcgtcgacca gaagtgagtt   4020
cttgagactg aaaactaatc ttttcactgg tttaattatt ttcagcgtta tcttgcatgc   4080
agtgttgtag agataataat ctcttttttt attaaaaaaa atgtttggtc tgaaaaaagc   4140
tagaaatata tagttgaact tcaattatat ttcaactttt gcgagaagtg gacgagataa   4200
ggtccaatcc ttctagaaaa ggtgcaggaa agtatatata tatatatata tatatatata   4260
tatatatata tatatatata tatatatata tatatatata tatatatata tatatgggga   4320
taaaatatga tcgagaaagt ccatcatcat ctagctgcaa gtcgttgtat ggatgtctta   4380
tggtgaccag gcaagagtgt tgatgtggaa agtacggtat gatttggtgt gctttacttg   4440
cttgactttg tgaggttgaa ccaccaccac agaagccgaa tcctcaccta ctcttgattg   4500
aagattggcc acccaaacca tcaccggttg ttgggagaaa tgaggataac tttctccatc   4560
gtttgctcca aaacctgtct acactttagt gtactgtctt tttcagtcag tgcgcaaacc   4620
acaccaccta cctccaacaa cattttgaga tagcgatttc ttttttcttt ttttaaaggc   4680
actccgtgtg tgaattatga tagaacagta acttttcaag caattttctt tgctgccagt   4740
caattttgga agaaaaaaaa aggcaacctc ggtaacacga atttaggttc ctattttgtt   4800
cttggtaaaa aaaaactaaa tacctagttc cacgtaagtt gatagttaat gcattttgtt   4860
tcaggtttgt ggtgaagatc ccggcgggtc tggctccgga gcaagcggcg ccgctgctgt   4920
gcgctggcgt gacggtgtac agcccgctga agcactttgg gctgacgacc ccgggcctcc   4980
gtggcggcat cctgggcctc ggcggcgtgg gccacatggg cgtgaaggta gccaaggcca   5040
tgggccacca cgtgacggtg atcagctcgt cgtccaagaa gcgcgcggag gcaatggacc   5100
```

acctcggcgc ggacgcgtac ctagtgagct cggacgccgc ggccatggcg gcggccgccg 5160
actcgctgga ctacatcatc gacacggtgc ccgtgcacca cccgctggag ccgtacctgg 5220
cgctgctgaa gctggacggc aagctcgtgc tgctgggcgt catcggcgag cccctgagct 5280
tcgtgtcgcc catggtgatg ctggggcgga aggccatcac ggggagcttc atcggcagca 5340
tcgacgagac cgctgaggtg cttcagttct gcgtcgacaa ggggctcacc tcccagatcg 5400
aggtggtcaa gatggggtac gtgaacgagg cgctggagcg gctggagcgc aacgacgtcc 5460
gctaccgctt cgtcgtcgac gtcgccggta gcaacgtcga ggcggaggcg gcggcggcgg 5520
atgcggccag caactgatgg caccgcgtcg tcgagtcgaa ccacgtctgt gcgccgcgtg 5580
caacgttcgt tcgggtcgag tctgcgtgca acgttctgct tcctttacta gttgttgtct 5640
ttccgccttc ttgccgttct gttctgggct ttgagatgag acgatggatg gtcagttttt 5700
aatgtcagac tgaataacta cgtatagtac tgtagtatta ctcggagtac gccagaatgt 5760
ggtgtggtgt cagtctcacc agcaatctgg atttgccaag tgtttctatt ttttcttcgg 5820
tttgcccgag tgtttgtgat tgttaagaac tacgttatta cggatcgtca aatccgttcc 5880
cttctgtctc gtctatag 5898

<210> SEQ ID NO 5
<211> LENGTH: 1510
<212> TYPE: DNA
<213> ORGANISM: Artificial
<220> FEATURE:
<223> OTHER INFORMATION: Predicted cDNA sequence of 6XN442 CAD2

<400> SEQUENCE: 5
gtgcgggctc gtctccatcg cccgccaccc gctccgtcgt cgtcgtcccc gccgcgccga 60
tcccgaatcg aatggggagc ctggcgtccg agaggaaggt ggtcgggtgg gccgccaggg 120
acgccaccgg acacctctcc ccctactcct acaccctcag gaacacaggc cctgaagatg 180
tggtggtgaa ggtgctctac tgcgggatct gccacacgga catccaccag gccaagaacc 240
acctcggggc ttcaaagtat cctatggtcc ctgggcacga ggtggtcggc gaggtggtgg 300
aggtcgggcc cgaggtggcc aagtacggcg tcggcgacgt ggtaggcgtc ggggtgatcg 360
ttgggtgctg ccgcgagtgc agcccctgca aggccaacgt tgagcagtac tgcaacaaga 420
agatctggtc atacaacgac gtctacactg atggacggcc cacgcagggt ggattcgcct 480
ccaccatggt cgtcgaccag aagtttgtgg tgaagatccc ggcgggtctg gctccggagc 540
aagcggcgcc gctgctgtgc gctggcgtga cggtgtacag cccgctgaag cactttgggc 600
tgacgacccc gggcctccgt ggcggcatcc tgggcctcgg cggcgtgggc cacatgggcg 660
tgaaggtagc caaggccatg ggccaccacg tgacggtgat cagctcgtcg tccaagaagc 720
gcgcggaggc aatggaccac ctcggcgcgg acgcgtacct agtgagctcg gacgccgcgg 780
ccatggcggc ggccgccgac tcgctggact acatcatcga cacggtgccc gtgcaccacc 840
cgctggagcc gtacctggcg ctgctgaagc tggacggcaa gctcgtgctg ctgggcgtca 900
tcggcgagcc cctgagcttc gtgtcgccca tggtgatgct ggggcggaag gccatcacgg 960
ggagcttcat cggcagcatc gacgagaccg ctgaggtgct tcagttctgc gtcgacaagg 1020
ggctcacctc ccagatcgag gtggtcaaga tggggtacgt gaacgaggcg ctggagcggc 1080
tggagcgcaa cgacgtccgc taccgcttcg tcgtcgacgt cgccggtagc aacgtcgagg 1140
cggaggcggc ggcggcggat gcggccagca actgatggca ccgcgtcgtc gagtcgaacc 1200

```
acgtctgtgc gccgcgtgca acgttcgttc gggtcgagtc tgcgtgcaac gttctgcttc   1260

ctttactagt tgttgtcttt ccgccttctt gccgttctgt tctgggcttt gagatgagac   1320

gatggatggt cagtttttaa tgtcagactg aataactacg tatagtactg tagtattact   1380

cggagtacgc cagaatgtgg tgtggtgtca gtctcaccag caatctggat ttgccaagtg   1440

tttctatttt ttcttcggtt tgcccgagtg tttgtgattg ttaagaacta cgttattacg   1500

gatcgtcaaa                                                          1510
```

<210> SEQ ID NO 6
<211> LENGTH: 367
<212> TYPE: PRT
<213> ORGANISM: Artificial
<220> FEATURE:
<223> OTHER INFORMATION: Predicted protein sequence of 6XN442 CAD2

<400> SEQUENCE: 6

```
Met Gly Ser Leu Ala Ser Glu Arg Lys Val Val Gly Trp Ala Ala Arg
1               5                   10                  15

Asp Ala Thr Gly His Leu Ser Pro Tyr Ser Tyr Thr Leu Arg Asn Thr
            20                  25                  30

Gly Pro Glu Asp Val Val Val Lys Val Leu Tyr Cys Gly Ile Cys His
        35                  40                  45

Thr Asp Ile His Gln Ala Lys Asn His Leu Gly Ala Ser Lys Tyr Pro
    50                  55                  60

Met Val Pro Gly His Glu Val Val Gly Glu Val Val Glu Val Gly Pro
65                  70                  75                  80

Glu Val Ala Lys Tyr Gly Val Gly Asp Val Val Gly Val Gly Val Ile
                85                  90                  95

Val Gly Cys Cys Arg Glu Cys Ser Pro Cys Lys Ala Asn Val Glu Gln
            100                 105                 110

Tyr Cys Asn Lys Lys Ile Trp Ser Tyr Asn Asp Val Tyr Thr Asp Gly
        115                 120                 125

Arg Pro Thr Gln Gly Gly Phe Ala Ser Thr Met Val Val Asp Gln Lys
    130                 135                 140

Phe Val Val Lys Ile Pro Ala Gly Leu Ala Pro Glu Gln Ala Ala Pro
145                 150                 155                 160

Leu Leu Cys Ala Gly Val Thr Val Tyr Ser Pro Leu Lys His Phe Gly
                165                 170                 175

Leu Thr Thr Pro Gly Leu Arg Gly Gly Ile Leu Gly Leu Gly Gly Val
            180                 185                 190

Gly His Met Gly Val Lys Val Ala Lys Ala Met Gly His His Val Thr
        195                 200                 205

Val Ile Ser Ser Ser Ser Lys Lys Arg Ala Glu Ala Met Asp His Leu
    210                 215                 220

Gly Ala Asp Ala Tyr Leu Val Ser Ser Asp Ala Ala Ala Met Ala Ala
225                 230                 235                 240

Ala Ala Asp Ser Leu Asp Tyr Ile Ile Asp Thr Val Pro Val His His
                245                 250                 255

Pro Leu Glu Pro Tyr Leu Ala Leu Leu Lys Leu Asp Gly Lys Leu Val
            260                 265                 270

Leu Leu Gly Val Ile Gly Glu Pro Leu Ser Phe Val Ser Pro Met Val
        275                 280                 285

Met Leu Gly Arg Lys Ala Ile Thr Gly Ser Phe Ile Gly Ser Ile Asp
    290                 295                 300
```

```
Glu Thr Ala Glu Val Leu Gln Phe Cys Val Asp Lys Gly Leu Thr Ser
305                 310                 315                 320

Gln Ile Glu Val Val Lys Met Gly Tyr Val Asn Glu Ala Leu Glu Arg
                325                 330                 335

Leu Glu Arg Asn Asp Val Arg Tyr Arg Phe Val Val Asp Val Ala Gly
            340                 345                 350

Ser Asn Val Glu Ala Glu Ala Ala Ala Ala Asp Ala Ala Ser Asn
        355                 360                 365


<210> SEQ ID NO 7
<211> LENGTH: 5916
<212> TYPE: DNA
<213> ORGANISM: Zea mays

<400> SEQUENCE: 7

aatgcacgat gtcaactctc ttgcctataa ttatgttcaa actctcgtca ataatagtag     60

ctagtactgt tattgtaaag tatcgctaaa atatgcatat atacttataa cttatccatg    120

ttaaagaaaa tcgaatatgc tagcaaagac atatgggccc gttgaggaga gctacgttac    180

atttgatttc taggagaaag cagagtgaag agctggtgaa aatcgattct ctattatctt    240

cactagaata taaatgaagc acatttttag ctccagctct tagcgcaaat agagaaactc    300

tcctaattgt agcatgaatg agatgacatt ataaaagcct ttgatgagat tttcttccga    360

gaagctgaag ctcctcagat agcccaatga tatgtatgta agtgtatttt ttttaaaaaa    420

agcgggcaaa tgaaactaaa tcatcctatc ccctttaata tactgagatg ccaattagtt    480

ggttgccagc cggagtatgg tggatgggat cctcctattg gttaaattat gaatgaattg    540

tttggttgcc cggtccaatc tttcttatgt ctgtttcgtt tagatcgtgt acaccacttc    600

ttattgttta aatggccaat ttaatcgggg cctaaacgac atatgtgcct caatttacca    660

taccaatgat gccgcttacg tgaatagttg aataccgata ctactactac cgcacgcgtc    720

atggtttaac cttttaacag ttggattgaa acatcagcga ccactcggca cttgggtgac    780

aatttgtcac acacctcgta gtcgagtgga aatgcactta cccaatttct caacccataa    840

gactatttcc agcatctcga ttaatcccca tatttaaaat caactttcat agtttatatt    900

gtgaagtgtt ttatgtgacg acattagtgg atttatggac acggtctaag gacccgtgac    960

ttgtattttt cttcattgac ctagctagct agctagctag catcgtgaag ccacgcccat   1020

gcgtttggta tcgtccgagt tgtgtacaat ttccagccag tggaatcaca gttattggat   1080

cattttggta cgtataacgt attctttttg tatttcctgt ctaaagacat taatttcaga   1140

gaagccgggt ctattttaga agggcttggc ttcttcccgt ttggtagacc tcctcgaaag   1200

acgaaagtct tacttcctct ggtttcctat tagttatcgt tttgaataaa gttcgagtca   1260

aacttataaa attttgacta caaataacta ttttgttatt tagttttgga acctaatatt   1320

tatatgcacc aatttgttat aaaacgtact tttataaaag tataaatgta ttaagagttc   1380

atttgtattt taacaaaaaa tattggtcaa agttatattt tggagaccgt gtcgttgtcc   1440

taaacgacaa ctaataggaa accggaggga gtactgattt tctcctgcag cgggcacaga   1500

agatcatgct ggaaaggtag taggtacagg tagcctggag cggaggagtt gccactttgc   1560

acagtgccga tcgagctcgc agccactata tagcacgcac cctgctcaag catcttttcc   1620

ttacccagaa agatcgcact acccggcgct cgcgcggctt tctttcccaa ctccgacgaa   1680

ggctagctac accacctggt gcgggctcgt ctccatcgcc cgccacccgc tccgtcgtcg   1740

tcgtccccgc cgcgccgatc ccgaatcgaa tggggagcct ggcgtccgag aggaaggtgg   1800
```

```
tcgggtgggc cgccagggac gccaccggac acctctcccc ctactcctac accctcaggt   1860
actacgccgc gccggcgccc tcgtgtttgt cctctcctcc agtccctccc gtctgtatat   1920
gtccgactgt ctccgccctt ttgcaaacac gcaaatggat ggatccagga ggacgagaga   1980
cggttagttt ctgcacgcgc ctcctccagt agttctccga gttctcggga agaacagaaa   2040
atttgattga tgtttttttt gatgaaaaat aaaaagggac ttggggcata ttttcgatca   2100
acttgcaacg gaagatgact aggagtacgt acgtagcgta gcggcggcgg gttttaattt   2160
gggggagcac tctgttagtc tgttgcatat atgggagtac ctgattcgtt gcagttatta   2220
ttatctatac gcgtacgata tgttttaggg ggtgtttggt tgctcctgct aaagtttagt   2280
ccgggtcaca tcaagcgttt tacttttaaa taggagtatg aaatatagac ccaaccaact   2340
agactagatt cgtctcgtct tttaatcttc ggctgacaaa ttagttttat aatccgacta   2400
catttaatac ccggaacaga ggttcaaaca ttcgatggga cagagactaa attttagcag   2460
ggtgtaacca aacacccccct tagtccacaa caagagcatt atgcgctgtg ttgcatcatg   2520
catatatgat acgtcttcaa cttcttgcgg tccaactcta gatagtgcac atgcatatgc   2580
caaatacgga tactggacaa gatagcacac aagcagagca ggttgggcga gcgtacactg   2640
cacgtatgct tctcttctac atggcatttt gtttcgaaca ttaatatatg ggtactgctc   2700
ctgcacagca ctgcacgtgc ttgacgtctc gtacagaccc agcagcgtgt gaacttgtag   2760
gtaagatacg taactactga tatctgcagc tacctaccgc ctgtcgcgat caccatccat   2820
ttgtactcgc agtaataata ccgattaccc ttttattatt atttctcatg ccatcgacga   2880
ctactagcac tatccaacgt acaactgtgg cgcgattcat atatgcataa ttctacatgg   2940
tgctagtctt cggcaagaaa aaaaaactaa cacttgtctc tttttcatat gggatgtgtt   3000
gtggtggtga caacaggaac acaggccctg aagatgtggt ggtgaaggtg ctctactgcg   3060
ggatctgcca cacggacatc caccaggcca agaaccacct cggggcttca aagtatccta   3120
tggtccctgg gtgagcacaa acggttaaca cacacacgca cccagcgatt tttcaggacc   3180
cttggggatc cagtatatat atatatgctc cgtgtacggt ccagaatata cgtactgaat   3240
ttccaagtgt cctattattc aatttgtctc aaaactataa aggatatata tagtgacatg   3300
cagtttcagc gttttcatga gaaaattaca catgcagaca aattcaggta taattatttg   3360
attcatgacg accagcatat agattggtag atagagtgca catttgtcaa ccacaaacgt   3420
tagcatccca gtccggagct atcccctggg ttacaggtgg caaatacaca ccaaccacaa   3480
taataagcta atactcttac gtctgtagtt ggttgccaat tactgatcag attacttgaa   3540
tcacaagagc ttgttgtgtc taatttgtac aggctattta tatcatgata gctaaagagc   3600
tgctgaaatg agtagcaagg aaacctcacc ggccgtccta tacttttctc tgacatgacg   3660
acaggacaac cactccacca ccgtgaactg atacaataac aataaagtcc tttagtccca   3720
gtaaattaga ataggctaga aactaaaatc caacagagag acgaaatcat ggctttggtt   3780
tgataataac tgatactttt gcaggcacga ggtggtcggc gaggtggtgg aggtcgggcc   3840
cgaggtggcc aagtacggcg tcggcgacgt ggtaggcgtc ggggtgatcg ttgggtgctg   3900
ccgcgagtgc agcccctgca aggccaacgt tgagcagtac tgcaacaaga agatctggtc   3960
atacaacgac gtctacactg atggacggcc cacgcagggt ggattcgcct ccaccatggt   4020
cgtcgaccag aagtgagttc ttgagactga aaactaatct tttcactggt ttaattattt   4080
tcagcgttat cttgcatgca gtgttgtaga gataataatc tcttttttta ttaaaaaaat   4140
```

```
gtttggtctg aaaaaagcta gaaatatata gttgaacttc aattatattt caacttttgc   4200
gagaagtgga cgagataagg tccaatcctt ctagaaaagg tgcaggaaag tatatatata   4260
tatatatata tatatatata tatatatata tatatatata tatatatata tatatatata   4320
tatatatata tatggggata aaatatgatc gagaaagtcc atcatcatct agctgcaagt   4380
cgttgtatgg atgtcttatg gtgaccaggc aagagtgttg atgtggaaag tacggtatga   4440
tttggtgtgc tttacttgct tgactttgtg aggttgaacc accaccacag aagccgaatc   4500
ctcacctact cttgattgaa gattggccac ccaaaccatc accggttgtt gggagaaatg   4560
aggataactt tctccatcgt tcgctccaaa acctgtctac actttagtgt actgtctttt   4620
tcagtcagtg cgcaaaccac accacctacc tccaacaaca ttttgagata gcgatttctt   4680
ttttcttttt ttaaaggcac tccgtgtgtg aattatgata gaacagtaac ttttcaagca   4740
attttctttg ctgccagtca attttggaag aaaaaaaaag gcaacctcgg taacacgaat   4800
ttaggttcct attttgttct tggtaaaaaa aaactaaata cctagttcca cgtaagttga   4860
tagttaatgc attttgtttc aggtttgtgg tgaagatccc ggcgggtctg gctccggagc   4920
aagcggcgcc gctgctgtgc gctggcgtga cggtgtacag cccgctgaag cactttgggc   4980
tgacgacccc gggcctccgt ggcggcatcc tgggcctcgg cggcgtgggc cacatgggcg   5040
tgaaggtagc caaggccatg ggccaccacg tgacggtgat cagctcgtcg tccaagaagc   5100
gcgcggaggc aatggaccac ctcggcgcgg acgcgtacct agtgagctcg gacgccgcgg   5160
ccatggcggc ggccgccgac tcgctggact acatcatcga cacggtgccc gtgcaccacc   5220
cgctggagcc gtacctggcg ctgctgaagc tggacggcaa gctcgtgctg ctgggcgtca   5280
tcggcgagcc cctgagcttc gtgtcgccca tggtgatgct ggggcggaag gccatcacgg   5340
ggagcttcat cggcagcatc gacgagaccg ctgaggtgct tcagttctgc gtcgacaagg   5400
gactcacctc ccagatcgag gtggtcaaga tggggtacgt gaacgaggcg ctggagcggc   5460
tggagcgcaa cgacgtccgc taccgcttcg tcgtcgacgt cgccggtagc aacgtcgagg   5520
cggaggcggc ggcggcggat gcggccagca actgatggca ccgcgtcgtc gagtcgaacc   5580
acgtctgtgc gccgcgtgca acgttcgttc gggtcgagtc tgcgtgcaac gttctgcttc   5640
ctttactagt tgttgtcttt ccgccttctt gccgttctgt tctgggcttt gagatgagac   5700
gatggatggt cagtttttaa tgtcagactg aataactacg tatagtactg tagtattact   5760
cggagtacgc cagaatgtgg tgtggtgtca gtctcaccag caatctggat ttgccaagtg   5820
tttctatttt ttcttcggtt tgcccgagtg tttgtgattg ttaagaacta cgttattacg   5880
gatcgtcaaa tccgttccct tctgtctcgt ctatag                             5916
```

```
<210> SEQ ID NO 8
<211> LENGTH: 1510
<212> TYPE: DNA
<213> ORGANISM: Artificial
<220> FEATURE:
<223> OTHER INFORMATION: Predicted cDNA sequence of B73 CAD2

<400> SEQUENCE: 8

gtgcgggctc gtctccatcg cccgccaccc gctccgtcgt cgtcgtcccc gccgcgccga     60
tcccgaatcg aatggggagc ctggcgtccg agaggaaggt ggtcgggtgg gccgccaggg    120
acgccaccgg acacctctcc ccctactcct acaccctcag gaacacaggc cctgaagatg    180
tggtggtgaa ggtgctctac tgcgggatct gccacacgga catccaccag gccaagaacc    240
acctcggggc ttcaaagtat cctatggtcc ctgggcacga ggtggtcggc gaggtggtgg    300
```

```
aggtcgggcc cgaggtggcc aagtacggcg tcggcgacgt ggtaggcgtc ggggtgatcg    360

ttgggtgctg ccgcgagtgc agcccctgca aggccaacgt tgagcagtac tgcaacaaga    420

agatctggtc atacaacgac gtctacactg atggacggcc cacgcagggt ggattcgcct    480

ccaccatggt cgtcgaccag aagtttgtgg tgaagatccc ggcgggtctg gctccggagc    540

aagcggcgcc gctgctgtgc gctggcgtga cggtgtacag cccgctgaag cactttgggc    600

tgacgacccc gggcctccgt ggcggcatcc tgggcctcgg cggcgtgggc cacatgggcg    660

tgaaggtagc caaggccatg ggccaccacg tgacggtgat cagctcgtcg tccaagaagc    720

gcgcggaggc aatggaccac ctcggcgcgg acgcgtacct agtgagctcg gacgccgcgg    780

ccatggcggc ggccgccgac tcgctggact acatcatcga cacggtgccc gtgcaccacc    840

cgctggagcc gtacctggcg ctgctgaagc tggacggcaa gctcgtgctg ctgggcgtca    900

tcggcgagcc cctgagcttc gtgtcgccca tggtgatgct ggggcggaag gccatcacgg    960

ggagcttcat cggcagcatc gacgagaccg ctgaggtgct tcagttctgc gtcgacaagg   1020

gactcacctc ccagatcgag gtggtcaaga tggggtacgt gaacgaggcg ctggagcggc   1080

tggagcgcaa cgacgtccgc taccgcttcg tcgtcgacgt cgccggtagc aacgtcgagg   1140

cggaggcggc ggcggcggat gcggccagca actgatggca ccgcgtcgtc gagtcgaacc   1200

acgtctgtgc gccgcgtgca acgttcgttc gggtcgagtc tgcgtgcaac gttctgcttc   1260

ctttactagt tgttgtcttt ccgccttctt gccgttctgt tctgggcttt gagatgagac   1320

gatggatggt cagtttttaa tgtcagactg aataactacg tatagtactg tagtattact   1380

cggagtacgc cagaatgtgg tgtggtgtca gtctcaccag caatctggat ttgccaagtg   1440

tttctatttt ttcttcggtt tgcccgagtg tttgtgattg ttaagaacta cgttattacg   1500

gatcgtcaaa                                                          1510


<210> SEQ ID NO 9
<211> LENGTH: 30
<212> TYPE: DNA
<213> ORGANISM: Artificial
<220> FEATURE:
<223> OTHER INFORMATION: Forward primer F5

<400> SEQUENCE: 9

aatgcacgat gtcaactctc ttgcctataa                                      30


<210> SEQ ID NO 10
<211> LENGTH: 28
<212> TYPE: DNA
<213> ORGANISM: Artificial
<220> FEATURE:
<223> OTHER INFORMATION: Reverse primer R5

<400> SEQUENCE: 10

aattttctca tgaaaacgct gaaactgc                                        28


<210> SEQ ID NO 11
<211> LENGTH: 22
<212> TYPE: DNA
<213> ORGANISM: Artificial
<220> FEATURE:
<223> OTHER INFORMATION: Forward primer 2933F

<400> SEQUENCE: 11

tgagcacaaa cggttaacac ac                                              22
```

<210> SEQ ID NO 12
<211> LENGTH: 22
<212> TYPE: DNA
<213> ORGANISM: Artificial
<220> FEATURE:
<223> OTHER INFORMATION: Reverse primer 2933R

<400> SEQUENCE: 12
attgtatcag ttcacggtgg tg 22

<210> SEQ ID NO 13
<211> LENGTH: 30
<212> TYPE: DNA
<213> ORGANISM: Artificial
<220> FEATURE:
<223> OTHER INFORMATION: Forward primer 3268F

<400> SEQUENCE: 13
cacaccaacc acaataataa gctaatactc 30

<210> SEQ ID NO 14
<211> LENGTH: 22
<212> TYPE: DNA
<213> ORGANISM: Artificial
<220> FEATURE:
<223> OTHER INFORMATION: Reverse primer 3268R

<400> SEQUENCE: 14
aacgatcacc ccgacgccta cc 22

<210> SEQ ID NO 15
<211> LENGTH: 30
<212> TYPE: DNA
<213> ORGANISM: Artificial
<220> FEATURE:
<223> OTHER INFORMATION: Forward primer 3479F

<400> SEQUENCE: 15
ccaccgtgaa ctgatacaat aacaataaag 30

<210> SEQ ID NO 16
<211> LENGTH: 30
<212> TYPE: DNA
<213> ORGANISM: Artificial
<220> FEATURE:
<223> OTHER INFORMATION: Reverse primer 3479R

<400> SEQUENCE: 16
acactgcatg caagataacg ctgaaaataa 30

<210> SEQ ID NO 17
<211> LENGTH: 22
<212> TYPE: DNA
<213> ORGANISM: Artificial
<220> FEATURE:
<223> OTHER INFORMATION: Forward primer 3742F

<400> SEQUENCE: 17
tgcaacaaga agatctggtc at 22

<210> SEQ ID NO 18
<211> LENGTH: 23
<212> TYPE: DNA
<213> ORGANISM: Artificial
<220> FEATURE:
<223> OTHER INFORMATION: Reverse primer 3742R

<400> SEQUENCE: 18
tcataccgta ctttccacat caa 23

<210> SEQ ID NO 19
<211> LENGTH: 27
<212> TYPE: DNA
<213> ORGANISM: Artificial
<220> FEATURE:
<223> OTHER INFORMATION: Forward primer 3996F

<400> SEQUENCE: 19
ttttgcgaga agtggacgag ataaggt 27

<210> SEQ ID NO 20
<211> LENGTH: 29
<212> TYPE: DNA
<213> ORGANISM: Artificial
<220> FEATURE:
<223> OTHER INFORMATION: Reverse primer 3996R

<400> SEQUENCE: 20
aatgttgttg gaggtaggtg gtgtggttt 29

<210> SEQ ID NO 21
<211> LENGTH: 29
<212> TYPE: DNA
<213> ORGANISM: Artificial
<220> FEATURE:
<223> OTHER INFORMATION: Forward primer BM11 C1

<400> SEQUENCE: 21
gagaaatgag gataactttc tccatcgtt 29

<210> SEQ ID NO 22
<211> LENGTH: 30
<212> TYPE: DNA
<213> ORGANISM: Artificial
<220> FEATURE:
<223> OTHER INFORMATION: Reverse primer BM11 R14

<400> SEQUENCE: 22
ctatagacga gacagaaggg aacggatttg 30

<210> SEQ ID NO 23
<211> LENGTH: 9360
<212> TYPE: DNA
<213> ORGANISM: Zea mays

<400> SEQUENCE: 23
aatgcacgat gtcaactctc ttgcctataa ttatgttcaa actctcgtca ataatagtag 60
ctagtactgt tattgtaaag tatcgctaaa atatgcatat atacttataa cttatccatg 120
ttaaagaaaa tcgaatatgc tagcaaagac atatgggccc gttgaggaga gctacgttac 180
atttgatttc taggagaaag cagagtgaag agctggtgaa aatcgattct ctattatctt 240
cactagaata taaatgaagc acatttttag ctccagctct tagcgcaaat agagaaactc 300
tcctaattgt agcatgaatg agatgacatt ataaaagcct ttgatgagat tttcttccga 360
gaagctgaag ctcctcagat agcccaatga tatgtatgta agtgtatttt ttttaaaaaa 420
agcgggcaaa tgaaactaaa tcatcctatc ccctttaata tactgagatg ccaattagtt 480
ggttgccagc cggagtatgg tggatgggat cctcctattg gttaaattat gaatgaattg 540

```
tttggttgcc cggtccaatc tttcttatgt ctgtttcgtt tagatcgtgt acaccacttc    600
ttattgttta aatggccaat ttaatcgggg cctaaacgac atatgtgcct caatttacca    660
taccaatgat gccgcttacg tgaatagttg aataccgata ctactactac cgcacgcgtc    720
atggtttaac cttttaacag ttggattgaa acatcagcga ccactcggca cttgggtgac    780
aatttgtcac acacctcgta gtcgagtgga aatgcactta cccaatttct caacccataa    840
gactatttcc agcatctcga ttaatcccca tatttaaaat caactttcat agtttatatt    900
gtgaagtgtt ttatgtgacg acattagtgg atttatggac acggtctaag gacccgtgac    960
ttgtattttt cttcattgac ctagctagct agctagctag catcgtgaag ccacgcccat   1020
gcgtttggta tcgtccgagt tgtgtacaat ttccagccag tggaatcaca gttattggat   1080
cattttggta cgtataacgt attctttttg tatttcctgt ctaaagacat taatttcaga   1140
gaagccgggt ctattttaga agggcttggc ttcttcccgt ttggtagacc tcctcgaaag   1200
acgaaagtct tacttcctct ggtttcctat tagttatcgt tttgaataaa gttcgagtca   1260
aacttataaa attttgacta caaataacta ttttgttatt tagttttgga acctaatatt   1320
tatatgcacc aatttgttat aaaacgtact tttataaaag tataaatgta ttaagagttc   1380
atttgtattt taacaaaaaa tattggtcaa agttatattt tggagaccgt gtcgttgtcc   1440
taaacgacaa ctaataggaa accggaggga gtactgattt tctcctgcag cgggcacaga   1500
agatcatgct ggaaaggtag taggtacagg tagcctggag cggaggagtt gccactttgc   1560
acagtgccga tcgagctcgc agccactata tagcacgcac cctgctcaag catcttttcc   1620
ttacccagaa agatcgcact acccggcgct cgcgcggctt tctttcccaa ctccgacgaa   1680
ggctagctac accacctggt gcgggctcgt ctccatcgcc cgccacccgc tccgtcgtcg   1740
tcgtccccgc cgcgccgatc ccgaatcgaa tggggagcct ggcgtccgag aggaaggtgg   1800
tcgggtgggc cgccagggac gccaccggac acctctcccc ctactcctac accctcaggt   1860
actacgccgc gccggcgccc tcgtgtttgt cctctcctcc agtccctccc gtctgtatat   1920
gtccgactgt ctccgccctt ttgcaaacac gcaaatggat ggatccagga ggacgagaga   1980
cggttagttt ctgcacgcgc ctcctccagt agttctccga gttctcggga agaacagaaa   2040
atttgattga tgtttttttt gatgaaaaat aaaaagggac ttggggcata ttttcgatca   2100
acttgcaacg gaagatgact aggagtacgt acgtagcgta gcggcggcgg gttttaattt   2160
gggggagcac tctgttagtc tgttgcatat atgggagtac ctgattcgtt gcagttatta   2220
ttatctatac gcgtacgata tgttttaggg ggtgtttggt tgctcctgct aaagtttagt   2280
ccgggtcaca tcaagcgttt tacttttaaa taggagtatg aaatatagac ccaaccaact   2340
agactagatt cgtctcgtct tttaatcttc ggctgacaaa ttagttttat aatccgacta   2400
catttaatac ccggaacaga ggttcaaaca ttcgatggga cagagactaa attttagcag   2460
ggtgtaacca aacacccccct tagtccacaa caagagcatt atgcgctgtg ttgcatcatg   2520
catatatgat acgtcttcaa cttcttgcgg tccaactcta gatagtgcac atgcatatgc   2580
caaatacgga tactggacaa gatagcacac aagcagagca ggttgggcga gcgtacactg   2640
cacgtatgct tctcttctac atggcatttt gtttcgaaca ttaatatatg ggtactgctc   2700
ctgcacagca ctgcacgtgc ttgacgtctc gtacagaccc agcagcgtgt gaacttgtag   2760
gtaagatacg taactactga tatctaggcc tgggaatggg ccatataaac tcatgggcag   2820
aaaggggctc caaacttgtg ggctaacaaa tttgagtttt tttgggcttt ccactgatta   2880
gggcaggcgg cgtcaggctg atcggggtgg cgcgcggcgc cggggagcgc cccatcgtat   2940
```

```
tcgtgcctct caaggtcaca ccgcctcgcg ctcgtctcct ctccttgtcg cttcgattcg   3000
ttcccctccc gctcccgctc gccctcgcca tgaatgatgt cgcctgaatc tggttctggg   3060
ggtttcggta gctactactt ggccggcttg ccgcctcttc ttctttgcgt tgctgctctg   3120
ccattttcct attgtagtag cggcgccatg cgagaacgag atgagccaac tgcagaggtt   3180
ggcttggctt ctgccatttt cttctttgct gcagaggttc gcggacgcag gtcggaccac   3240
tgccgcgccc ttcctcttcc tgccggccgc cgcactcccg ccagcgccgt actacttact   3300
acctgcatac tgtattctgt agtagtatga aaaggtaaag gcggcgtact gctatagtat   3360
ctctgcagaa tgttcggagg aggagtacac caactgaaag aggtttagga aagttgcacc   3420
gtggatctag aattctagat gcattagtgt agcctacagt agccctgtac acacataaag   3480
gcatttttct tataaaattg tctcgcaaaa tgggattttt ttgtgctaat tatagggtgc   3540
tttagcgcca cctgggattt ttttgtgcta attatatgca gcttccatag accaccacag   3600
gcattcccgc atgcagttcg ctctgaatgc ctcctttcat tctattacta tccctgaacg   3660
acgacccatc tcagggaaat agccattaaa tgatagcagc ctttttttaaa gtatggcttg   3720
gtttgcgatg ttattatggt tcgaaaagtt gctctatttt agtctcattt attttataaa   3780
ttgcagtact aaactgtttt agtctatagt tcctttttag atgactaaaa gggattaaac   3840
aaaaaagaca cccgtaaatt aatcagtcgt taaacagtgc tagtactatg catttcatcg   3900
cgtaaattaa tcaattgaat ggtttcaatt ggtgattttg cagcctaggc catggagggg   3960
gtatcatcag ctccagaaat ggacgaggct atctcaactg accaatcaag cagatcaaca   4020
aaaagaaggg ctaaagtgtg ggatcatgtt gattcagagc taatagatgg gaaagagaag   4080
gcggtttgca aatactgtaa ggcccactta tcttctgctg cgggtaaagg tacaactcat   4140
ctaaataggc atatttctgt gtattgccat gcaattccac cagaagagag acaaaggttc   4200
ttagcgaccc aaaaaacaaa gcctgatgtt gctcatgttt tcgacccagt agtctttcgt   4260
ggtctaatag ccaagtactt ccttagcgca gagatttcat tttgaaagtg tgaagatcca   4320
tcctggaaag aaatgataag ttattgtcaa ccatcttttc gattagtcgg tcgacagact   4380
gtccgttcag attgtatgtt gttgtatgaa gaggagaagt tgcagttaat tgagcagttt   4440
acaaagttga aatctcatgt tagtttgact gctgatcttt ggtcctctaa ccaaaacctt   4500
ggatatcttg gtgtaacagc acatttcatt agtgaagatt ttgagttgca caaaaagatt   4560
attgcattca agaagatttc cttcccacat acatcttatg ctgtgcaaga tggtattacc   4620
tcttgtttgc tagagtgggg attggttggt gatttgttta ccctgacttt ggataatgct   4680
agtgtaaaca atagagcaat gaaagatatg cgagatgctt tgggcagcca gatgtttttc   4740
agtggtgaac acctccatgt gaggtgttct tctcatgtgc tcaacatcat ggttcaagct   4800
ggactaaagg tcgttccaaa tgcagaatat cattagcatt atatagttta tcttttgtct   4860
taatcaccaa agatgttttt cagaatatca ttagcagcca gatgtttttg tcttaatctc   4920
aacatcattt tcttaatcac caaagtttta tcttttgtct gttcttctct aatatccatg   4980
catctaaata agccctaata gtatctctca ttctcttgtt actattagta tttaaactta   5040
ttactattag tatttaagcg tgaataatta tcattagcat ttaagttaca ttttataaac   5100
caaacgacac ctaaagtgct ccgtcatagt tggctacttg ccagccgatt atttagcacg   5160
caagccatgc tcgatggata caatagtata tgaccaatat agatgaccta cgtacatgtg   5220
ttctatgctt cagcaagcat aatatgtttc ttgccttcgc atcaactcaa gtgtgtgatg   5280
```

```
atatgttgct gtctagtact aactctgaat caattaactc tgaatttgtc caggctaagg   5340
agttccttgg tgcttccggt gacaagcgaa aggaagtcaa ttaactctga atcagtggtt   5400
ctgctgcaag gtaaattgcc tgtatataat tatccatgtc agaaccaact ttatctacca   5460
ggattaattt ttagtctccc aattttatgc cccagttata ttttatccta gtgaagtttt   5520
actgctctca tatacttaga tgaactaaag ttgatcattt tgtgctcgga acaactctgt   5580
ataacagtct atatagttta acagtctata tagtttgcat gcaggttaca cacaacattt   5640
tattgaatgg aaagaggaca ctcggtgacc acaagatcat cagatgatca tttgttgagc   5700
tctggaacta aatcctctcc gcaggtggta accaggcggg ttcccatccg agttccgagg   5760
tcactgtaat gctaaattgt caagttcagt tatctgaatt cagtttgagt tataattctc   5820
atcaagcatc aatgtcacca actgtgtaga aatactgaat tttagcatgg agcgtcttta   5880
taaacatttt agcatggagc agtttctcat cgatcatggc tgtcaagttc tatttctcta   5940
cacagttgca ctttgtggtt gttttctatc atttgtttgt gagcccatgg atttactaa    6000
tttattagct tgtggtggtg cttgcttgta tatgaaggcc cttggattgg cccgtggatt   6060
tttaaaagga tcgaggcgga ttaggatgtc ggggcattaa aaaacggatt gaattgagtt   6120
gtatcaaatc aatttggatt taagtagggc tgggttcact ttttaaactt ataggattgg   6180
agtggggttg gggccggatt gtgacccatt atcaggctta ctgatatctg cagctaccta   6240
ccgcctgtcg cgatcaccat ccatttgtac tcgcagtaat aataccgatt accctttat    6300
tattatttct catgccatcg acgactacta gcactatcca acgtacaact gtggcgcgat   6360
tcatatatgc ataattctac atggtgctag tcttcggcaa gaaaaaaaaa ctaacacttg   6420
tctcttttc atatgggatg tgttgtggtg gtgacaacag gaacacaggc cctgaagatg    6480
tggtggtgaa ggtgctctac tgcgggatct gccacacgga catccaccag gccaagaacc   6540
acctcggggc ttcaaagtat cctatggtcc ctgggtgagc acaaacggtt aacacacaca   6600
cgcacccagc gatttttcag gacccttggg gatccagtat atatatatat gctccgtgta   6660
cggtccagaa tatacgtact gaatttccaa gtgtcctatt attcaatttg tctcaaaact   6720
ataaaggata tatatagtga catgcagttt cagcgttttc atgagaaaat tacacatgca   6780
gacaaattca ggtataatta tttgattcat gacgaccagc atatagattg gtagatagag   6840
tgcacatttg tcaaccacaa acgttagcat cccagtccgg agctatcccc tgggttacag   6900
gtggcaaata cacaccaacc acaataataa gctaatactc ttacgtctgt agttggttgc   6960
caattactga tcagattact tgaatcacaa gagcttgttg tgtctaattt gtacaggcta   7020
tttatatcat gatagctaaa gagctgctga aatgagtagc aaggaaacct caccggccgt   7080
cctatacttt tctctgacat gacgacagga caaccactcc accaccgtga actgatacaa   7140
taacaataaa gtcctttagt cccagtaaat tagaataggc tagaaactaa aatccaacag   7200
agagacgaaa tcatggcttt ggtttgataa taactgatac ttttgcaggc acgaggtggt   7260
cggcgaggtg gtggaggtcg ggcccgaggt ggccaagtac ggcgtcggcg acgtggtagg   7320
cgtcggggtg atcgttgggt gctgccgcga gtgcagcccc tgcaaggcca acgttgagca   7380
gtactgcaac aagaagatct ggtcatacaa cgacgtctac actgatggac ggcccacgca   7440
gggtggattc gcctccacca tggtcgtcga ccagaagtga gttcttgaga ctgaaaacta   7500
atcttttcac tggtttaatt attttcagcg ttatcttgca tgcagtgttg tagagataat   7560
aatctctttt tttattaaaa aaatgtttgg tctgaaaaaa gctagaaata tatagttgaa   7620
cttcaattat atttcaactt ttgcgagaag tggacgagat aaggtccaat ccttctagaa   7680
```

```
aaggtgcagg aaagtatata tatatatata tatatatata tatatatata tatatatata   7740

tatatatata tatatatata tatatatata tatatatggg gataaaatat gatcgagaaa   7800

gtccatcatc atctagctgc aagtcgttgt atggatgtct tatggtgacc aggcaagagt   7860

gttgatgtgg aaagtacggt atgatttggt gtgctttact tgcttgactt tgtgaggttg   7920

aaccaccacc acagaagccg aatcctcacc tactcttgat tgaagattgg ccacccaaac   7980

catcaccggt tgttgggaga aatgaggata actttctcca tcgttcgctc caaaacctgt   8040

ctacacttta gtgtactgtc tttttcagtc agtgcgcaaa ccacaccacc tacctccaac   8100

aacattttga gatagcgatt tctttttct ttttttaaag gcactccgtg tgtgaattat   8160

gatagaacag taacttttca agcaattttc tttgctgcca gtcaattttg gaagaaaaaa   8220

aaaggcaacc tcggtaacac gaatttaggt tcctattttg ttcttggtaa aaaaaaacta   8280

aatacctagt tccacgtaag ttgatagtta atgcattttg tttcaggttt gtggtgaaga   8340

tcccggcggg tctggctccg gagcaagcgg cgccgctgct gtgcgctggc gtgacggtgt   8400

acagcccgct gaagcacttt gggctgacga ccccgggcct ccgtggcggc atcctgggcc   8460

tcggcggcgt gggccacatg ggcgtgaagg tagccaaggc catgggccac cacgtgacgg   8520

tgatcagctc gtcgtccaag aagcgcgcgg aggcaatgga ccacctcggc gcggacgcgt   8580

acctagtgag ctcggacgcc gcggccatgg cggcggccgc cgactcgctg gactacatca   8640

tcgacacggt gcccgtgcac cacccgctgg agccgtacct ggcgctgctg aagctggacg   8700

gcaagctcgt gctgctgggc gtcatcggcg agcccctgag cttcgtgtcg cccatggtga   8760

tgctggggcg gaaggccatc acggggagct tcatcggcag catcgacgag accgctgagg   8820

tgcttcagtt ctgcgtcgac aagggactca cctcccagat cgaggtggtc aagatggggt   8880

acgtgaacga ggcgctggag cggctggagc gcaacgacgt ccgctaccgc ttcgtcgtcg   8940

acgtcgccgg tagcaacgtc gaggcggagg cggcggcggc ggatgcggcc agcaactgat   9000

ggcaccgcgt cgtcgagtcg aaccacgtct gtgcgccgcg tgcaacgttc gttcgggtcg   9060

agtctgcgtg caacgttctg cttcctttac tagttgttgt ctttccgcct tcttgccgtt   9120

ctgttctggg ctttgagatg agacgatgga tggtcagttt ttaatgtcag actgaataac   9180

tacgtatagt actgtagtat tactcggagt acgccagaat gtggtgtggt gtcagtctca   9240

ccagcaatct ggatttgcca agtgtttcta ttttttcttc ggtttgcccg agtgtttgtg   9300

attgttaaga actacgttat tacggatcgt caaatccgtt cccttctgtc tcgtctatag   9360
```

<210> SEQ ID NO 24
<211> LENGTH: 784
<212> TYPE: DNA
<213> ORGANISM: Artificial
<220> FEATURE:
<223> OTHER INFORMATION: partial DASbm1 CAD2 cDNA amplified by primer pair CVF/CVR

<400> SEQUENCE: 24

```
gtccgagagg aaggtggtcg ggtgggccgc cagggacgcc accggacacc tctcccccta     60

ctcctacacc ctcagcctag gccatggagg gggtatcatc agctccagaa atggacgagg    120

ctatctcaac tgaccaatca agcagatcaa caaaaagaag ggctaaagtg tgggatcatg    180

ttgattcaga gctaatagat gggaaagaga aggcggtttg caaatactgt aaggcccact    240

tatcttctgc tgcgggtaaa ggctaaggag ttccttggtg cttccggtga caagcgaaag    300

gaagtcaatt aactctgaat cagtggttct gctgcaaggt tgcatgcagg ttacacacaa    360
```

```
cattttattg aatggaaaga ggacactcgg tgaccacaag atcatcagat gatcatttgt    420

tgagctctgg aactaaatcc tctccgcagg tggtaaccag gcgggttccc atccgagttc    480

cgaggaacac aggccctgaa gatgtggtgg tgaaggtgct ctactgcggg atctgccaca    540

cggacatcca ccaggccaag aaccacctcg ggcttcaaa gtatcctatg gtccctgggc     600

acgaggtggt cggcgaggtg gtggaggtcg ggcccgaggt ggccaagtac ggcgtcggcg    660

acgtggtagg cgtcggggtg atcgttgggt gctgccgcga gtgcagcccc tgcaaggcca    720

acgttgagca gtactgcaac aagaagatct ggtcatacaa cgacgtctac actgatggac    780

ggcc                                                                 784


<210> SEQ ID NO 25
<211> LENGTH: 48
<212> TYPE: PRT
<213> ORGANISM: Artificial
<220> FEATURE:
<223> OTHER INFORMATION: Predicted truncated protein sequence of DASbm1
      CAD2

<400> SEQUENCE: 25

Met Gly Ser Leu Ala Ser Glu Arg Lys Val Val Gly Trp Ala Ala Arg
1               5                   10                  15

Asp Ala Thr Gly His Leu Ser Pro Tyr Ser Tyr Thr Leu Ser Leu Gly
            20                  25                  30

His Gly Gly Gly Ile Ile Ser Ser Arg Asn Gly Arg Gly Tyr Leu Asn
        35                  40                  45


<210> SEQ ID NO 26
<211> LENGTH: 30
<212> TYPE: DNA
<213> ORGANISM: Artificial
<220> FEATURE:
<223> OTHER INFORMATION: Forward primer 149F

<400> SEQUENCE: 26

aatgcacgat gtcaactctc ttgcctataa                                      30


<210> SEQ ID NO 27
<211> LENGTH: 24
<212> TYPE: DNA
<213> ORGANISM: Artificial
<220> FEATURE:
<223> OTHER INFORMATION: Reverse primer 149R

<400> SEQUENCE: 27

tgggttgaga aattgggtaa gtgc                                            24


<210> SEQ ID NO 28
<211> LENGTH: 21
<212> TYPE: DNA
<213> ORGANISM: Artificial
<220> FEATURE:
<223> OTHER INFORMATION: Forward primer 547F

<400> SEQUENCE: 28

tgcccggtcc aatctttctt a                                               21


<210> SEQ ID NO 29
<211> LENGTH: 20
<212> TYPE: DNA
<213> ORGANISM: Artificial
<220> FEATURE:
```

<223> OTHER INFORMATION: Reverse primer 547R

<400> SEQUENCE: 29
cgtctttcga ggaggtctac 20

<210> SEQ ID NO 30
<211> LENGTH: 24
<212> TYPE: DNA
<213> ORGANISM: Artificial
<220> FEATURE:
<223> OTHER INFORMATION: Forward primer 1022F

<400> SEQUENCE: 30
cgtttggtat cgtccgagtt gtgt 24

<210> SEQ ID NO 31
<211> LENGTH: 23
<212> TYPE: DNA
<213> ORGANISM: Artificial
<220> FEATURE:
<223> OTHER INFORMATION: Reverse primer 1022R

<400> SEQUENCE: 31
gccgggtagt gcgatctttc tgg 23

<210> SEQ ID NO 32
<211> LENGTH: 24
<212> TYPE: DNA
<213> ORGANISM: Artificial
<220> FEATURE:
<223> OTHER INFORMATION: Forward primer 1501F

<400> SEQUENCE: 32
agatcatgct ggaaaggtag tagg 24

<210> SEQ ID NO 33
<211> LENGTH: 23
<212> TYPE: DNA
<213> ORGANISM: Artificial
<220> FEATURE:
<223> OTHER INFORMATION: Reverse primer 1501R

<400> SEQUENCE: 33
tgatcgaaaa tatgccccaa gtc 23

<210> SEQ ID NO 34
<211> LENGTH: 24
<212> TYPE: DNA
<213> ORGANISM: Artificial
<220> FEATURE:
<223> OTHER INFORMATION: Forward primer 1955F

<400> SEQUENCE: 34
acgcgcctcc tccagtagtt ctcc 24

<210> SEQ ID NO 35
<211> LENGTH: 24
<212> TYPE: DNA
<213> ORGANISM: Artificial
<220> FEATURE:
<223> OTHER INFORMATION: Reverse primer 1955R

<400> SEQUENCE: 35
caagttcaca cgctgctggg tctg 24

<210> SEQ ID NO 36
<211> LENGTH: 19
<212> TYPE: DNA
<213> ORGANISM: Artificial
<220> FEATURE:
<223> OTHER INFORMATION: Forward primer CVF

<400> SEQUENCE: 36
gtccgagagg aaggtggtc 19

<210> SEQ ID NO 37
<211> LENGTH: 19
<212> TYPE: DNA
<213> ORGANISM: Artificial
<220> FEATURE:
<223> OTHER INFORMATION: Reverse primer CVR

<400> SEQUENCE: 37
ggccgtccat cagtgtaga 19

<210> SEQ ID NO 38
<211> LENGTH: 20
<212> TYPE: DNA
<213> ORGANISM: Artificial
<220> FEATURE:
<223> OTHER INFORMATION: Forward primer 2687F

<400> SEQUENCE: 38
tatgggtact gctcctgcac 20

<210> SEQ ID NO 39
<211> LENGTH: 19
<212> TYPE: DNA
<213> ORGANISM: Artificial
<220> FEATURE:
<223> OTHER INFORMATION: Reverse primer 2643R

<400> SEQUENCE: 39
ccttgcagca gaaccactg 19

<210> SEQ ID NO 40
<211> LENGTH: 21
<212> TYPE: DNA
<213> ORGANISM: Artificial
<220> FEATURE:
<223> OTHER INFORMATION: Forward primer 2132F

<400> SEQUENCE: 40
agaatatcat tagcagccag a 21

<210> SEQ ID NO 41
<211> LENGTH: 3444
<212> TYPE: DNA
<213> ORGANISM: Zea mays

<400> SEQUENCE: 41
aggcctggga atgggccata taaactcatg ggcagaaagg ggctccaaac ttgtgggcta 60
acaaatttga gttttttttgg gctttccact gattagggca ggcggcgtca ggctgatcgg 120
ggtggcgcgc ggcgccgggg agcgccccat cgtattcgtg cctctcaagg tcacaccgcc 180
tcgcgctcgt ctcctctcct tgtcgcttcg attcgttccc ctcccgctcc cgctcgccct 240
cgccatgaat gatgtcgcct gaatctggtt ctgggggttt cggtagctac tacttggccg 300
gcttgccgcc tcttcttctt tgcgttgctg ctctgccatt ttcctattgt agtagcggcg 360

```
ccatgcgaga acgagatgag ccaactgcag aggttggctt ggcttctgcc attttcttct    420
ttgctgcaga ggttcgcgga cgcaggtcgg accactgccg cgcccttcct cttcctgccg    480
gccgccgcac tcccgccagc gccgtactac ttactacctg catactgtat tctgtagtag    540
tatgaaaagg taaaggcggc gtactgctat agtatctctg cagaatgttc ggaggaggag    600
tacaccaact gaaagaggtt taggaaagtt gcaccgtgga tctagaattc tagatgcatt    660
agtgtagcct acagtagccc tgtacacaca taaaggcatt tttcttataa aattgtctcg    720
caaaatggga tttttttgtg ctaattatag ggtgctttag cgccacctgg gatttttttg    780
tgctaattat atgcagcttc catagaccac cacaggcatt cccgcatgca gttcgctctg    840
aatgcctcct ttcattctat tactatccct gaacgacgac ccatctcagg gaaatagcca    900
ttaaatgata gcagcctttt ttaaagtatg gcttggtttg cgatgttatt atggttcgaa    960
aagttgctct attttagtct catttatttt ataaattgca gtactaaact gttttagtct   1020
atagttcctt tttagatgac taaaagggat taaacaaaaa agacacccgt aaattaatca   1080
gtcgttaaac agtgctagta ctatgcattt catcgcgtaa attaatcaat tgaatggttt   1140
caattggtga ttttgcagcc taggccatgg agggggtatc atcagctcca gaaatggacg   1200
aggctatctc aactgaccaa tcaagcagat caacaaaaag aagggctaaa gtgtgggatc   1260
atgttgattc agagctaata gatgggaaag agaaggcggt ttgcaaatac tgtaaggccc   1320
acttatcttc tgctgcgggt aaaggtacaa ctcatctaaa taggcatatt tctgtgtatt   1380
gccatgcaat tccaccagaa gagagacaaa ggttcttagc gacccaaaaa acaaagcctg   1440
atgttgctca tgttttcgac ccagtagtct ttcgtggtct aatagccaag tacttcctta   1500
gcgcagagat ttcattttga aagtgtgaag atccatcctg gaaagaaatg ataagttatt   1560
gtcaaccatc ttttcgatta gtcggtcgac agactgtccg ttcagattgt atgttgttgt   1620
atgaagagga gaagttgcag ttaattgagc agtttacaaa gttgaaatct catgttagtt   1680
tgactgctga tctttggtcc tctaaccaaa accttggata tcttggtgta acagcacatt   1740
tcattagtga agattttgag ttgcacaaaa agattattgc attcaagaag atttccttcc   1800
cacatacatc ttatgctgtg caagatggta ttacctcttg tttgctagag tggggattgg   1860
ttggtgattt gtttaccctg actttggata atgctagtgt aaacaataga gcaatgaaag   1920
atatgcgaga tgctttgggc agccagatgt ttttcagtgg tgaacacctc catgtgaggt   1980
gttcttctca tgtgctcaac atcatggttc aagctggact aaaggtcgtt ccaaatgcag   2040
aatatcatta gcattatata gtttatcttt tgtcttaatc accaaagatg tttttcagaa   2100
tatcattagc agccagatgt tttgtcttta atctcaacat cattttctta atcaccaaag   2160
ttttatcttt tgtctgttct tctctaatat ccatgcatct aaataagccc taatagtatc   2220
tctcattctc ttgttactat tagtatttaa acttattact attagtattt aagcgtgaat   2280
aattatcatt agcatttaag ttacatttta taaaccaaac gacacctaaa gtgctccgtc   2340
atagttggct acttgccagc cgattattta gcacgcaagc catgctcgat ggatacaata   2400
gtatatgacc aatatagatg acctacgtac atgtgttcta tgcttcagca agcataatat   2460
gtttcttgcc ttcgcatcaa ctcaagtgtg tgatgatatg ttgctgtcta gtactaactc   2520
tgaatcaatt aactctgaat ttgtccaggc taaggagttc cttggtgctt ccggtgacaa   2580
gcgaaaggaa gtcaattaac tctgaatcag tggttctgct gcaaggtaaa ttgcctgtat   2640
ataattatcc atgtcagaac caactttatc taccaggatt aatttttagt ctcccaattt   2700
tatgccccag ttatatttta tcctagtgaa gttttactgc tctcatatac ttagatgaac   2760
```

```
taaagttgat cattttgtgc tcggaacaac tctgtataac agtctatata gtttaacagt   2820

ctatatagtt tgcatgcagg ttacacacaa cattttattg aatggaaaga ggacactcgg   2880

tgaccacaag atcatcagat gatcatttgt tgagctctgg aactaaatcc tctccgcagg   2940

tggtaaccag gcgggttccc atccgagttc cgaggtcact gtaatgctaa attgtcaagt   3000

tcagttatct gaattcagtt tgagttataa ttctcatcaa gcatcaatgt caccaactgt   3060

gtagaaatac tgaattttag catggagcgt ctttataaac attttagcat ggagcagttt   3120

ctcatcgatc atggctgtca agttctattt ctctacacag ttgcactttg tggttgtttt   3180

ctatcatttg tttgtgagcc catggatttt actaatttat tagcttgtgg tggtgcttgc   3240

ttgtatatga aggcccttgg attggcccgt ggatttttaa aaggatcgag gcggattagg   3300

atgtcggggc attaaaaaac ggattgaatt gagttgtatc aaatcaattt ggatttaagt   3360

agggctgggt tcacttttta aacttatagg attggagtgg ggttggggcc ggattgtgac   3420

ccattatcag gcttactgat atct                                          3444
```

```
<210> SEQ ID NO 42
<211> LENGTH: 11
<212> TYPE: DNA
<213> ORGANISM: Artificial
<220> FEATURE:
<223> OTHER INFORMATION: Duplicated region of transposon insertion
      sequence

<400> SEQUENCE: 42

tactgatatc t                                                          11


<210> SEQ ID NO 43
<211> LENGTH: 24
<212> TYPE: DNA
<213> ORGANISM: Artificial
<220> FEATURE:
<223> OTHER INFORMATION: Oligonucleotide AC_R1

<400> SEQUENCE: 43

tcagtctcaa gaactcactt ctgg                                            24


<210> SEQ ID NO 44
<211> LENGTH: 39
<212> TYPE: DNA
<213> ORGANISM: Artificial
<220> FEATURE:
<223> OTHER INFORMATION: Oligonucleotide AC_A1

<400> SEQUENCE: 44

gaaggtgacc aagttcatgc tactgatgga cggcccaca                            39


<210> SEQ ID NO 45
<211> LENGTH: 39
<212> TYPE: DNA
<213> ORGANISM: Artificial
<220> FEATURE:
<223> OTHER INFORMATION: Oligonucleotide AC_A2

<400> SEQUENCE: 45

gaaggtcgga gtcaacggat tactgatgga cggcccacg                            39


<210> SEQ ID NO 46
<211> LENGTH: 76
<212> TYPE: DNA
<213> ORGANISM: Zea mays
```

<400> SEQUENCE: 46
actgatggac ggcccacacg cagggtggat tcgcctccac catggtcgtc gaccagaagt 60
gagttcttga gactga 76

<210> SEQ ID NO 47
<211> LENGTH: 74
<212> TYPE: DNA
<213> ORGANISM: Zea mays

<400> SEQUENCE: 47
actgatggac ggcccacgca gggtggattc gcctccacca tggtcgtcga ccagaagtga 60
gttcttgaga ctga 74

<210> SEQ ID NO 48
<211> LENGTH: 17
<212> TYPE: DNA
<213> ORGANISM: Artificial
<220> FEATURE:
<223> OTHER INFORMATION: DASbm1-specific probe

<400> SEQUENCE: 48
aggcttactg atatctg 17

<210> SEQ ID NO 49
<211> LENGTH: 21
<212> TYPE: DNA
<213> ORGANISM: Artificial
<220> FEATURE:
<223> OTHER INFORMATION: Wild-type CAD2 specific probe

<400> SEQUENCE: 49
ctgcagatat cagtagttac g 21

<210> SEQ ID NO 50
<211> LENGTH: 20
<212> TYPE: DNA
<213> ORGANISM: Artificial
<220> FEATURE:
<223> OTHER INFORMATION: Forward primer DASbm1_F

<400> SEQUENCE: 50
gccggattgt gacccattat 20

<210> SEQ ID NO 51
<211> LENGTH: 18
<212> TYPE: DNA
<213> ORGANISM: Artificial
<220> FEATURE:
<223> OTHER INFORMATION: Reverse primer DASbm1_R

<400> SEQUENCE: 51
cgcgacaggc ggtaggta 18

<210> SEQ ID NO 52
<211> LENGTH: 23
<212> TYPE: DNA
<213> ORGANISM: Artificial
<220> FEATURE:
<223> OTHER INFORMATION: Forward primer Wt CAD2_F

<400> SEQUENCE: 52
gcagcgtgtg aacttgtagg taa 23

<210> SEQ ID NO 53
<211> LENGTH: 13
<212> TYPE: DNA
<213> ORGANISM: Artificial
<220> FEATURE:
<223> OTHER INFORMATION: 515Dbm1-specific probe

<400> SEQUENCE: 53
acggcccaca cgc 13

<210> SEQ ID NO 54
<211> LENGTH: 14
<212> TYPE: DNA
<213> ORGANISM: Artificial
<220> FEATURE:
<223> OTHER INFORMATION: Wt CAD2-specific probe

<400> SEQUENCE: 54
acggcccacg cagg 14

<210> SEQ ID NO 55
<211> LENGTH: 25
<212> TYPE: DNA
<213> ORGANISM: Artificial
<220> FEATURE:
<223> OTHER INFORMATION: Forward primer bm1_F

<400> SEQUENCE: 55
ggtcatacaa cgacgtctac actga 25

<210> SEQ ID NO 56
<211> LENGTH: 18
<212> TYPE: DNA
<213> ORGANISM: Artificial
<220> FEATURE:
<223> OTHER INFORMATION: Reverse primer bm1_R

<400> SEQUENCE: 56
atggtggagg cgaatcca 18

<210> SEQ ID NO 57
<211> LENGTH: 19
<212> TYPE: DNA
<213> ORGANISM: Artificial
<220> FEATURE:
<223> OTHER INFORMATION: Forward primer CAD2_F

<400> SEQUENCE: 57
ccacatgggc gtgaaggta 19

<210> SEQ ID NO 58
<211> LENGTH: 21
<212> TYPE: DNA
<213> ORGANISM: Artificial
<220> FEATURE:
<223> OTHER INFORMATION: Reverse primer CAD2_R

<400> SEQUENCE: 58
ttcttggacg acgagctgat c 21

<210> SEQ ID NO 59
<211> LENGTH: 16
<212> TYPE: DNA
<213> ORGANISM: Artificial
<220> FEATURE:
<223> OTHER INFORMATION: Probe CAD2_Eprobe

<400> SEQUENCE: 59
atgggccacc acgtga 16

<210> SEQ ID NO 60
<211> LENGTH: 18
<212> TYPE: DNA
<213> ORGANISM: Artificial
<220> FEATURE:
<223> OTHER INFORMATION: Forward primer INV59F

<400> SEQUENCE: 60
atggtggagg cgaatcca 18

<210> SEQ ID NO 61
<211> LENGTH: 15
<212> TYPE: DNA
<213> ORGANISM: Artificial
<220> FEATURE:
<223> OTHER INFORMATION: Reverse primer INV59R

<400> SEQUENCE: 61
tgccgtccgt gccct 15

<210> SEQ ID NO 62
<211> LENGTH: 18
<212> TYPE: DNA
<213> ORGANISM: Artificial
<220> FEATURE:
<223> OTHER INFORMATION: Probe INV_probe

<400> SEQUENCE: 62
ccgtgtactt ctacctgc 18

<210> SEQ ID NO 63
<211> LENGTH: 160
<212> TYPE: DNA
<213> ORGANISM: Zea mays

<400> SEQUENCE: 63
gtgcgggctc gtctccatcg cccgccaccc gctccgtcgt cgtcgtcccc gccgcgccga 60
tcccgaatcg aatggggagc ctggcgtccg agaggaaggt ggtcgggtgg gccgccaggg 120
acgccaccgg acacctctcc ccctactcct acaccctcag 160

<210> SEQ ID NO 64
<211> LENGTH: 114
<212> TYPE: DNA
<213> ORGANISM: Zea mays

<400> SEQUENCE: 64
gaacacaggc cctgaagatg tggtggtgaa ggtgctctac tgcgggatct gccacacgga 60
catccaccag gccaagaacc acctcggggc ttcaaagtat cctatggtcc ctgg 114

<210> SEQ ID NO 65
<211> LENGTH: 228
<212> TYPE: DNA
<213> ORGANISM: Zea mays

<400> SEQUENCE: 65
gcacgaggtg gtcggcgagg tggtggaggt cgggcccgag gtggccaagt acggcgtcgg 60
cgacgtggta ggcgtcgggg tgatcgttgg gtgctgccgc gagtgcagcc cctgcaaggc 120

-continued

```
caacgttgag cagtactgca acaagaagat ctggtcatac aacgacgtct acactgatgg    180

acggcccacg cagggtggat tcgcctccac catggtcgtc gaccagaa                 228
```